(12) United States Patent
Marks et al.

(10) Patent No.: US 7,718,644 B2
(45) Date of Patent: May 18, 2010

(54) ANTI-ARRHYTHMIC AND HEART FAILURE DRUGS THAT TARGET THE LEAK IN THE RYANODINE RECEPTOR (RYR2) AND USES THEREOF

(75) Inventors: Andrew Robert Marks, Larchmont, NY (US); Donald W. Landry, New York, NY (US); Shixian Deng, White Plains, NY (US); Zhen Zhuang Cheng, Elmhurst, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1428 days.

(21) Appl. No.: 10/809,089

(22) Filed: Mar. 25, 2004

(65) Prior Publication Data
US 2005/0215540 A1 Sep. 29, 2005

Related U.S. Application Data

(63) Continuation-in-part of application No. 10/763,498, filed on Jan. 22, 2004, now abandoned.

(51) Int. Cl.
*A01N 43/00* (2006.01)
*A61K 31/00* (2006.01)

(52) U.S. Cl. .................................. 514/211.05; 540/552

(58) Field of Classification Search ........................ None
See application file for complete search history.

(56) References Cited

U.S. PATENT DOCUMENTS

| 3,367,930 A | 2/1968 | Schmutz et al. |
| 3,519,647 A | 7/1970 | Krapcho |
| 4,567,254 A | 1/1986 | Kataoka et al. |
| 4,658,055 A | 4/1987 | Onuki et al. |

(Continued)

FOREIGN PATENT DOCUMENTS

DE 3837575 5/1990

(Continued)

OTHER PUBLICATIONS

Loughrey et al, Cardiovascular Research 76 (2007) 236-246.*

(Continued)

*Primary Examiner*—Frederick Krass
*Assistant Examiner*—Benjamin Packard
(74) *Attorney, Agent, or Firm*—Winston & Strawn LLP

(57) ABSTRACT

The present invention provides methods for limiting or preventing a decrease in the level of RyR2-bound FKBP12.6 in a subject. The present invention further provides methods for treating and preventing atrial and ventricular cardiac arrhythmias, heart failure, and exercise-induced sudden cardiac death in a subject. Additionally, the present invention provides use of JTV-519 in a method for limiting or preventing a decrease in the level of RyR2-bound FKBP12.6 in a subject who has, or is a candidate for, atrial fibrillation. Also provided are uses of 1,4-benzothiazepine derivatives in methods for treating and preventing atrial and ventricular cardiac arrhythmias and heart failure in a subject, and for preventing exercise-induced sudden cardiac death. The present invention also provides methods for identifying agents for use in treating and preventing atrial fibrillation and heart failure, and agents identified by these methods.

29 Claims, 18 Drawing Sheets

U.S. PATENT DOCUMENTS

| | | |
|---|---|---|
| 4,723,012 A | 2/1988 | Matsumoto et al. |
| 4,841,055 A | 6/1989 | Matsumoto et al. |
| 4,845,065 A | 7/1989 | Sugimori et al. |
| 4,849,535 A | 7/1989 | Naora et al. |
| 4,888,418 A | 12/1989 | Kawai et al. |
| 4,963,671 A | 10/1990 | Krapcho |
| 4,990,707 A | 2/1991 | Mais et al. |
| 5,064,810 A | 11/1991 | Askanazi et al. |
| 5,075,293 A | 12/1991 | Reifschneider et al. |
| 5,142,647 A | 8/1992 | Nakagawa et al. |
| 5,153,184 A | 10/1992 | Reifschneider et al. |
| 5,166,347 A | 11/1992 | Izawa et al. |
| 5,179,125 A | 1/1993 | Mimura et al. |
| 5,180,720 A | 1/1993 | Husa et al. |
| 5,182,272 A | 1/1993 | Hallinan et al. |
| 5,204,462 A | 4/1993 | Kobayashi et al. |
| 5,210,266 A | 5/1993 | Mimura et al. |
| 5,214,056 A | 5/1993 | Haruta et al. |
| 5,221,681 A | 6/1993 | Kabbe et al. |
| 5,223,508 A | 6/1993 | Izawa et al. |
| 5,260,286 A | 11/1993 | Lawson et al. |
| 5,272,164 A | 12/1993 | Izawa et al. |
| 5,304,380 A | 4/1994 | Miyajima et al. |
| 5,304,558 A | 4/1994 | Kaneko et al. |
| 5,304,644 A | 4/1994 | Husa et al. |
| 5,324,722 A | 6/1994 | Hagen et al. |
| 5,332,734 A | 7/1994 | Kobayashi et al. |
| 5,354,747 A | 10/1994 | Hansen, Jr. et al. |
| 5,354,758 A | 10/1994 | Lawson et al. |
| 5,387,684 A | 2/1995 | Inoue et al. |
| 5,413,929 A | 5/1995 | Ishizaki et al. |
| 5,416,066 A | 5/1995 | Kaneko et al. |
| 5,449,675 A | 9/1995 | Chandrakumar et al. |
| 5,453,282 A | 9/1995 | Kanauchi et al. |
| 5,457,182 A | 10/1995 | Wiederrecht et al. |
| 5,461,047 A | 10/1995 | Hansen, Jr. et al. |
| 5,476,780 A | 12/1995 | Watanabe et al. |
| 5,478,832 A | 12/1995 | Inoue et al. |
| 5,508,293 A | 4/1996 | Okawara et al. |
| 5,523,410 A | 6/1996 | Kagara et al. |
| 5,580,866 A * | 12/1996 | Housley et al. ........ 514/211.09 |
| 5,593,988 A | 1/1997 | Tahara et al. |
| 5,624,961 A | 4/1997 | Ban et al. |
| 5,654,001 A | 8/1997 | Kanauchi et al. |
| 5,665,881 A | 9/1997 | Inoue et al. |
| 5,719,155 A | 2/1998 | Cho et al. |
| 5,723,458 A | 3/1998 | Brieaddy et al. |
| 5,750,696 A | 5/1998 | Shibata et al. |
| 5,753,649 A | 5/1998 | Tahara et al. |
| 5,767,247 A | 6/1998 | Kaneko et al. |
| 5,780,441 A | 7/1998 | Higa et al. |
| 5,792,655 A | 8/1998 | Watanabe et al. |
| 5,807,850 A | 9/1998 | Nakamura et al. |
| 5,817,652 A | 10/1998 | Brieaddy et al. |
| 5,824,862 A | 10/1998 | Hiyoshi et al. |
| 5,859,240 A | 1/1999 | Brieaddy |
| 5,866,341 A | 2/1999 | Spinella et al. |
| 5,906,819 A | 5/1999 | Kaibuchi et al. |
| 5,910,494 A | 6/1999 | Brieaddy |
| 6,013,499 A | 1/2000 | Narumiya et al. |
| 6,111,072 A | 8/2000 | Narumiya et al. |
| 6,130,060 A | 10/2000 | Nakamura et al. |
| 6,143,784 A | 11/2000 | Greenhaff et al. |
| 6,184,352 B1 | 2/2001 | Nakamura et al. |
| 6,235,730 B1 | 5/2001 | Sato et al. |
| 6,255,472 B1 | 7/2001 | Tokino et al. |
| 6,271,353 B1 | 8/2001 | Nakamura et al. |
| 6,313,113 B1 | 11/2001 | Lohray et al. |
| 6,316,485 B1 | 11/2001 | Nakamura et al. |
| 6,338,955 B2 | 1/2002 | Oguri et al. |
| 6,348,334 B1 | 2/2002 | Nagata et al. |
| 6,362,231 B1 | 3/2002 | Sakai et al. |
| 6,391,595 B1 | 5/2002 | Kato et al. |
| 6,403,830 B2 | 6/2002 | Webber et al. |
| 6,410,561 B1 | 6/2002 | Shinkai et al. |
| 6,426,365 B1 | 7/2002 | Shinkai et al. |
| 6,465,518 B2 | 10/2002 | Hansen, Jr. et al. |
| 6,465,686 B2 | 10/2002 | Grapperhaus et al. |
| 6,489,125 B1 | 12/2002 | Marks et al. |
| 6,495,544 B2 | 12/2002 | Hansen, Jr. et al. |
| 6,500,816 B1 | 12/2002 | Ekimoto et al. |
| 6,506,745 B1 | 1/2003 | Aisaka et al. |
| 6,545,170 B2 | 4/2003 | Pitzele et al. |
| 6,562,618 B1 | 5/2003 | Tamatani et al. |
| 6,562,828 B1 | 5/2003 | Katoh et al. |
| 6,583,157 B2 | 6/2003 | McGee et al. |
| 6,586,474 B2 | 7/2003 | Webber et al. |
| 6,632,976 B1 | 10/2003 | Tomizuka et al. |
| 6,649,366 B2 | 11/2003 | Chubinskaya et al. |
| 6,660,837 B1 | 12/2003 | Kaibuchi et al. |
| 6,673,904 B2 | 1/2004 | Nishikawa et al. |
| 6,683,083 B1 | 1/2004 | Kaneko et al. |
| 6,750,255 B2 | 6/2004 | Sakai et al. |
| 6,753,346 B2 | 6/2004 | Shinkai et al. |
| 6,756,406 B2 | 6/2004 | Durley et al. |
| 6,780,608 B1 | 8/2004 | Hakamata et al. |
| 6,787,668 B2 | 9/2004 | Pitzele et al. |
| 6,803,039 B2 | 10/2004 | Tsuji et al. |
| 6,808,873 B2 | 10/2004 | Murphy et al. |
| 6,812,252 B2 | 11/2004 | Ikawa et al. |
| 6,821,987 B2 | 11/2004 | Kubo et al. |
| 6,824,973 B2 | 11/2004 | Tang et al. |
| 6,828,456 B2 | 12/2004 | Hansen, Jr. et al. |
| 6,830,896 B2 | 12/2004 | Kaneko et al. |
| 6,852,753 B2 | 2/2005 | Koeller et al. |
| 6,869,975 B2 | 3/2005 | Abe et al. |
| 6,890,531 B1 | 5/2005 | Horie et al. |
| 6,897,295 B1 | 5/2005 | Nagata et al. |
| 6,906,072 B1 | 6/2005 | Yamamoto et al. |
| 6,914,158 B2 | 7/2005 | Webber et al. |
| 6,939,895 B2 | 9/2005 | Sakai et al. |
| 6,951,889 B2 | 10/2005 | Hansen, Jr. et al. |
| 6,962,926 B2 | 11/2005 | Laborde et al. |
| 6,964,975 B2 | 11/2005 | Ueno et al. |
| 6,977,252 B1 | 12/2005 | Kaneko et al. |
| 6,989,275 B2 | 1/2006 | Waggoner |
| 6,998,469 B2 | 2/2006 | Tandon et al. |
| 7,005,450 B2 | 2/2006 | Durley et al. |
| 7,029,671 B1 | 4/2006 | Koezuka et al. |
| 7,030,225 B1 | 4/2006 | Tamatani et al. |
| 7,041,870 B2 | 5/2006 | Tomizuka et al. |
| 7,045,615 B2 | 5/2006 | Tamatani et al. |
| 7,064,194 B2 | 6/2006 | Misawa et al. |
| 7,102,013 B2 | 9/2006 | Webber et al. |
| 7,112,655 B1 | 9/2006 | Tamatani et al. |
| 7,135,466 B2 | 11/2006 | Sakai et al. |
| 7,163,952 B2 | 1/2007 | Inaba et al. |
| 7,312,044 B2 | 12/2007 | Marks |
| 7,393,652 B2 | 7/2008 | Marks |
| 2002/0042405 A1 | 4/2002 | Schuh |
| 2002/0052358 A1 | 5/2002 | Chubinskaya et al. |
| 2002/0107406 A1 | 8/2002 | Sakai et al. |
| 2002/0115831 A1 | 8/2002 | Tamatani et al. |
| 2002/0132001 A1 | 9/2002 | Garthwaite et al. |
| 2002/0151685 A1 | 10/2002 | Tamatani et al. |
| 2002/0156242 A1 | 10/2002 | Tamatani et al. |
| 2002/0199213 A1 | 12/2002 | Tomizuka et al. |
| 2003/0022911 A1 | 1/2003 | Smith et al. |
| 2003/0044845 A1 | 3/2003 | Jenkins et al. |
| 2003/0054531 A1 | 3/2003 | Gretarsdottir et al. |
| 2003/0055027 A1 | 3/2003 | Schun |
| 2003/0055087 A1 | 3/2003 | Shinkai et al. |
| 2003/0064406 A1 | 4/2003 | Kaneko et al. |
| 2003/0083472 A1 | 5/2003 | Tamatani et al. |

| | | | |
|---|---|---|---|
| 2003/0087907 A1 | 5/2003 | Kubo et al. |
| 2003/0092708 A1 | 5/2003 | Shinkai et al. |
| 2003/0124637 A1 | 7/2003 | Kaneko et al. |
| 2003/0134331 A1 | 7/2003 | Marks |
| 2003/0144526 A1 | 7/2003 | Sakai et al. |
| 2003/0176485 A1 | 9/2003 | Sakai et al. |
| 2003/0181764 A1 | 9/2003 | Ikawa et al. |
| 2003/0186885 A1 | 10/2003 | Tandon et al. |
| 2003/0191323 A1 | 10/2003 | Ikawa et al. |
| 2003/0195218 A1 | 10/2003 | Koeller et al. |
| 2003/0199482 A1 | 10/2003 | Seibert et al. |
| 2003/0199701 A1 | 10/2003 | Webber et al. |
| 2003/0220310 A1 | 11/2003 | Schuh |
| 2003/0220312 A1 | 11/2003 | Schuh |
| 2003/0232855 A1 | 12/2003 | Iwamura et al. |
| 2004/0006099 A1 | 1/2004 | Katoh et al. |
| 2004/0017409 A1 | 1/2004 | Mizutani et al. |
| 2004/0048780 A1 | 3/2004 | Marks |
| 2004/0053919 A1 | 3/2004 | Chubinskaya et al. |
| 2004/0073012 A1 | 4/2004 | Tamatani et al. |
| 2004/0073957 A1 | 4/2004 | Tomizuka et al. |
| 2004/0082653 A1 | 4/2004 | Nonaka et al. |
| 2004/0120945 A1 | 6/2004 | Tamatani et al. |
| 2004/0132658 A1 | 7/2004 | Tamatani et al. |
| 2004/0132727 A1 | 7/2004 | Sakai et al. |
| 2004/0146506 A1 | 7/2004 | Tamatani et al. |
| 2004/0146991 A1 | 7/2004 | Tsuji et al. |
| 2004/0151669 A1 | 8/2004 | Tamatani et al. |
| 2004/0151718 A1 | 8/2004 | Tamatani et al. |
| 2004/0151720 A1 | 8/2004 | Tamatani et al. |
| 2004/0171613 A1 | 9/2004 | Iwamura et al. |
| 2004/0173802 A1 | 9/2004 | Yukimoto |
| 2004/0175814 A1 | 9/2004 | Kato et al. |
| 2004/0180052 A1 | 9/2004 | Tsuji et al. |
| 2004/0186178 A1 | 9/2004 | Webber et al. |
| 2004/0192584 A1 | 9/2004 | McMahon et al. |
| 2004/0198719 A1 | 10/2004 | Laborde et al. |
| 2004/0209871 A1 | 10/2004 | Fox et al. |
| 2004/0220193 A1 | 11/2004 | Yamamoto et al. |
| 2004/0224368 A1 | 11/2004 | Marks |
| 2004/0225018 A1 | 11/2004 | Sunami et al. |
| 2004/0229781 A1 | 11/2004 | Marks et al. |
| 2004/0229788 A1 | 11/2004 | Tamatani et al. |
| 2004/0229790 A1 | 11/2004 | Tezuka et al. |
| 2004/0229803 A1 | 11/2004 | Stephenson et al. |
| 2004/0229876 A1 | 11/2004 | Kubo et al. |
| 2004/0229957 A1 | 11/2004 | Shinkai et al. |
| 2004/0235162 A1 | 11/2004 | Sato |
| 2004/0242683 A1 | 12/2004 | Urata et al. |
| 2005/0009733 A1 | 1/2005 | Stephenson et al. |
| 2005/0020668 A1 | 1/2005 | Urata et al. |
| 2005/0032210 A1 | 2/2005 | Sato et al. |
| 2005/0035939 A1 | 2/2005 | Akiyama |
| 2005/0051181 A1 | 3/2005 | Okamoto |
| 2005/0059655 A1 | 3/2005 | Garvey et al. |
| 2005/0059810 A1 | 3/2005 | Maeda et al. |
| 2005/0070543 A1 | 3/2005 | Stephenson |
| 2005/0070545 A1 | 3/2005 | Fox et al. |
| 2005/0074762 A1 | 4/2005 | Nakamura et al. |
| 2005/0113451 A1 | 5/2005 | Hansen et al. |
| 2005/0159365 A1 | 7/2005 | Serizawa et al. |
| 2005/0159403 A1 | 7/2005 | Stephenson et al. |
| 2005/0165106 A1 | 7/2005 | Webber et al. |
| 2005/0171196 A1 | 8/2005 | Fujii et al. |
| 2005/0177884 A1 | 8/2005 | Tomizuka et al. |
| 2005/0186640 A1 | 8/2005 | Marks et al. |
| 2005/0187221 A1 | 8/2005 | Matsuda et al. |
| 2005/0187386 A1 | 8/2005 | Marks et al. |
| 2005/0192259 A1 | 9/2005 | Garthwaite et al. |
| 2005/0213426 A1 | 9/2005 | Midas et al. |
| 2005/0215540 A1 | 9/2005 | Marks et al. |
| 2005/0255546 A1 | 11/2005 | Nishikawa |
| 2005/0256199 A1 | 11/2005 | Durley et al. |
| 2005/0277649 A1 | 12/2005 | DeGraffenreid et al. |
| 2006/0011375 A1 | 1/2006 | Sugimoto et al. |
| 2006/0014768 A1 | 1/2006 | Kawasaki et al. |
| 2006/0026698 A1 | 2/2006 | Tomizuka et al. |
| 2006/0030565 A1 | 2/2006 | Shinkai et al. |
| 2006/0035882 A1 | 2/2006 | Koga et al. |
| 2006/0037093 A1 | 2/2006 | Tomizuka et al. |
| 2006/0041945 A1 | 2/2006 | Robl et al. |
| 2006/0059575 A1 | 3/2006 | Kusunoki et al. |
| 2006/0078992 A1 | 4/2006 | Misawa et al. |
| 2006/0084658 A1 | 4/2006 | Yamamoto et al. |
| 2006/0100195 A1 | 5/2006 | Maruyama et al. |
| 2006/0122181 A1 | 6/2006 | Ikemoto et al. |
| 2006/0123490 A1 | 6/2006 | Kakitani et al. |
| 2006/0135506 A1 | 6/2006 | Stephenson et al. |
| 2006/0167043 A1 | 7/2006 | Iwakubo et al. |
| 2006/0185025 A1 | 8/2006 | Oshimura et al. |
| 2006/0189603 A1 | 8/2006 | Garvey et al. |
| 2006/0194767 A1 | 8/2006 | Marks et al. |
| 2006/0205731 A1 | 9/2006 | Kodama et al. |
| 2006/0211717 A1 | 9/2006 | Sakai et al. |
| 2006/0217426 A1 | 9/2006 | Eto et al. |
| 2006/0223133 A1 | 10/2006 | Tamatani et al. |
| 2006/0233902 A1 | 10/2006 | Yajima et al. |
| 2006/0258701 A1 | 11/2006 | Mitsuya et al. |
| 2006/0270705 A1 | 11/2006 | Yonemori et al. |
| 2006/0293266 A1 | 12/2006 | Marks |
| 2007/0010571 A1 | 1/2007 | Garvey et al. |
| 2007/0010670 A1 | 1/2007 | Hirata et al. |
| 2007/0049572 A1 | 3/2007 | Marks et al. |
| 2007/0173482 A1 | 7/2007 | Marks et al. |

FOREIGN PATENT DOCUMENTS

| | | | |
|---|---|---|---|
| EP | 0467325 | | 1/1992 |
| EP | 0565721 | | 10/1993 |
| EP | 0718261 | | 6/1996 |
| EP | 1147772 | | 10/2001 |
| EP | 1369129 | | 12/2003 |
| EP | 1439221 | A1 | 7/2004 |
| EP | 1447096 | | 8/2004 |
| EP | 1743895 | | 1/2007 |
| FR | 2709753 | | 3/1995 |
| JP | 3093419 | | 4/1991 |
| JP | 4230681 | | 8/1992 |
| JP | 05/271208 | | 10/1993 |
| JP | 10045706 | | 2/1998 |
| JP | 11199574 | | 7/1999 |
| WO | WO-91/04328 | | 4/1991 |
| WO | WO92/12148 | | 7/1992 |
| WO | WO-92/19617 | | 11/1992 |
| WO | WO-93/13082 | | 11/1992 |
| WO | 9300095 | | 1/1993 |
| WO | WO 93/04053 | | 3/1993 |
| WO | WO 93/09104 | | 5/1993 |
| WO | WO-94/11360 | | 5/1994 |
| WO | WO 94/18183 | | 8/1994 |
| WO | WO-94/29286 | | 12/1994 |
| WO | WO-96/08228 | | 3/1996 |
| WO | WO 96/18629 | | 6/1996 |
| WO | WO-97/03986 | | 2/1997 |
| WO | WO-97/17344 | | 5/1997 |
| WO | WO-98/01417 | | 1/1998 |
| WO | WO-98/05657 | | 2/1998 |
| WO | WO-98/45291 | | 10/1998 |
| WO | WO-99/16758 | | 4/1999 |
| WO | WO-99/26921 | | 6/1999 |
| WO | WO-99/32115 | | 7/1999 |
| WO | WO-01/00185 | | 1/2001 |
| WO | WO-01/47510 | | 7/2001 |
| WO | WO-02/08211 | | 1/2002 |
| WO | WO-02/14245 | | 2/2002 |
| WO | WO-02/14246 | | 2/2002 |

| | | |
|---|---|---|
| WO | WO-02/051232 | 7/2002 |
| WO | WO-02/051838 | 7/2002 |
| WO | WO-02/053548 | 7/2002 |
| WO | WO-02056790 | 7/2002 |
| WO | WO-02/072145 | 9/2002 |
| WO | WO-03/034980 | 5/2003 |
| WO | WO-03/043655 | 5/2003 |
| WO | WO-2004/022057 | 3/2004 |
| WO | WO-2004/023030 | 3/2004 |
| WO | WO-2004/042389 A2 | 5/2004 |
| WO | WO-2004/080283 | 9/2004 |
| WO | WO 2004/104895 | 12/2004 |
| WO | WO-2005/002518 | 1/2005 |
| WO | WO 2005/026177 | 3/2005 |
| WO | WO-2005/037195 | 4/2005 |
| WO | WO-2005/094457 | 10/2005 |
| WO | WO-2005/105793 | 11/2005 |
| WO | WO-2006/071603 | 7/2006 |
| WO | WO-2006/101496 | 9/2006 |
| WO | WO-2006/101497 | 9/2006 |
| WO | WO-2007/024717 | 3/2007 |
| WO | WO-2007/127145 | 11/2007 |
| WO | WO-2007/143112 | 12/2007 |
| WO | WO-2008/021432 | 2/2008 |
| WO | WO-2008/021439 | 2/2008 |
| WO | WO-2008/060332 | 5/2008 |
| WO | WO-2008/140592 | 11/2008 |

OTHER PUBLICATIONS

Xin et al, Oestrogen protects FKBP12.6 null mice from hypertrophy, Nature, v 416 issue 6878, 2002, pp. 334-337.*
Tomaselli and Zipes, Circulation Research 95 (8) 754 (2004).*
Salama et al, The houral of Physiology, vol. 578 Iss 1 (2006) pp. 43-53.*
Pfmmatter et al (Acta Paediatr 84 (1995) 569-572).*
Hain, Jurgen et al. "Phosphorylation Modulates the Function of the Calcium Release Channel of Sarcoplasmic Reticulum from Cardiac Muscle." The Journal of Biological Chemistry, vol. 270, No. 5, pp. 2074-2081. (Feb. 3, 1995).
Isselbacher, Kurt J. et al. "Harrison's Principles of Internal Medicine." 13th Edition, vol. 1, pp. 1022-1024. (1994).
Kohno et al., "A New Cardioprotective Agent, JTV-519, Improves Defective Channel Gating of Ryanodine Receptor in Heart Failure." Am. J. Physiol Heart Circ. Physiol., vol. 284, No. 3, pp. H1035-H1042. First published Nov. 14, 2002. (Mar. 2003).
Kumagai et al. "Antiarrhythmic Effects of JTV-519, a novel Cardioprotective Drug, on Atrial Fibrillation/Flutter in a Canine Sterile Pericarditis Model." J. Cardiovasc. Electrophysiol. vol. 14, No. 8, pp. 880-884. (2003).
Szabo et al. "Synthesis and Transformations of 4,5-Dihydro-1,4-benzothiazepin-3(2H)-one Derivatives1,2)." Chemische Berichte., vol. 119, No. 9, pp. 2904-2913. (1986).
Szabo, Janos et al., "Synthesis and Spectroscopic Investigations of 1,4-benzothiazepine derivatives." Can. J. Chem, vol. 65, pp. 175-181. (1987).
Yano et al., "RyR-Bound FKBP12.6 and the Modulation." Journal Clinical Calcium, vol. 11, No. 6, pp. 743-748. (Jun. 2001).
Haut, Donahue, et al., "Annexin V Disruption Impairs Mechanically Induced Calcium Signaling in Osteoblastic Cells," Bone, vol. 35, No. 3) pp. 656-663, (2004).
Ackerman, MJ, "Cardiac channelopathies: it's in the genes," Nat. Med., vol. 10, pp. 463-464 (2004).
Bangur, et al., "Mutational analysis of the D1/E1 core helices and the conserved N-terminal region of yeast transcription factor IIB (TFIIB): identification of an N-terminal mutant that stabilizes TATA-binding protein-TFIIB-DNA complexes," Mol. Cell Biol., vol. 17, pp. 6784-6793 (1997).
Brillantes, et al., "Developmental and tissue-specific regulation of rabbit skeletal and cardiac muscle calcium channels involved in excitation-contraction coupline, " Circ. Res., vol. 75, pp. 503-510 (1994).

Brillantes, et al., "Differences in cardiac calcium release channel (ryanodine receptor) expression in myocardium from patients with end-state heart failure caused by ischemic versus dilated cardiomyopathy," Circ. Res., vol. 71, pp. 18-26 (1992).
Chatrath, et al., "Beta-blocker therapy failures in symptomatic probands with genotyped long-QT syndrome," Pediatr. Cardiol., vol. 25, pp. 459-465 (2004).
Che, et al., "Reversal of P-glycoprotein mediated multidrug resistance by a newly synthesized 1,4-benzothiazipine derivative, JTV-519," Cancer Lett., vol. 187, pp. 111-119 (2002).
Choi, et al., "Spectrum and frequency of cardiac channel defects in swimming-triggered arrhythmia syndromes," Circulation, vol. 110, pp. 2119-2124 (2004).
Choi, et al., "Sudden cardiac death and channelopathies: a review of implantable defibrillator therapy," Pediatr. Clin. North Am., vol. 51, pp. 1289-1303 (2004).
Farr, et al., "Sparking the failing heart," N. Engl. J. Med., vol. 351, pp. 185-187 (2004).
Fitzgerald, et al., "Reduced ryanodine receptor content in isolated neonatal cardiomyocytes compared with the intact tissue," J. Mol. Cell, Cardiol., vol. 26, pp. 1261-1265 (1994).
Gillian, et al., "Analysis of expression of the human ryanodine receptor gene in malignant hyperthermia skeletal muscle tissue," Biochem. Soc. Trans., vol. 19, pp. 46S (1991).
Ikemoto, et al., "Regulation of calcium release by interdomain interaction within ryanodine receptors," Front Biosci., vol. 7, pp. d671-683 (2002).
Kirsch, et al., "The roles of annexins and types ll and X collagen in matrix vesicle-mediated mineralization of growth plate cartilage," J. Biol. Chem., vol. 275, pp. 35577-35583 (2000).
Kobrinsky, et al., "Expressed ryanodine receptor can substitute for the inositol 1,4,5-trisphosphate receptor in *Xenopus laevis* oocytes during progesterone-induced maturation," Dev. Biol., vol. 172, pp. 531-540 (1995).
Lehnart, et al., "Immunophilins and coupled gating of ryanodine receptors," Curr. Top. Med. Chem., vol. 3, pp. 1383-1391 (2003).
Lehnart, et al., "Calstabin deficiency, ryanodine receptors, and sudden cardiac death," Biochem. Biophys. Res. Commun., vol. 322, pp. 1267-1279 (2004).
Lesh, et al., "Anti-ryanodine receptor antibody binding sites in vascular and endocardial endothelium," Cir., Res., vol. 72, pp. 481-488 (1993).
Marks, AR, "Calcium channels expressed in vascular smooth muscle," Circulation, vol. 86, pp. III61-III67 (1992).
Marks, AR, "Immunophilin modulation of calcium channel gating," Methods., vol. 9, pp. 177-187 (1996).
Marks, AR, "Intracellular calcium-release channels: regulators of cell life and death," Am. J. Phsiol., vol. 272, pp. H597-H605 (1997).
Marks, et al., "Molecular cloning and characterization of the Ryanodine receptor/junctional channel complex cDNA from skeletal muscle sarcoplasmic reticulum," Proc. Natl. Acad. Sci. U.S.A., vol. 86, pp. 8683-8687 (1989).
Marks, et al., "Regulation of ryanodine receptors via macromolecular complexes: a novel role for leucine/isoleucine zippers," Tends Cardiovasc. Med., vol. 12, pp. 166-170 (2002).
Marks, et al., "Surface topography analysis of the ryanodine receptor/junctional channel complex based on proteolysis sensitivity mapping," J. Biol. Chem., vol. 265, pp. 13143-13149 (1990).
Marks, et al., "The ryanodine receptor/junctional channel complex is regulated by growth factors in a myogenic cell line," J. Cell. Biol., vol. 114, pp. 303-312, (1991).
Maron, et al., "Recommendations for physical activity and recreational sports participation for young patients with genetic cardiovascular diseases," Circulation, vol., 109, pp. 2807-2816 (2004).
McPhie, et al., "Structure of the hormone binding domain of human beta 1 thyroid hormone nuclear receptor: is is an alpha/beta barrel?" Biochemistry, vol. 32, pp. 7460-7465 (1993).
Nakamura, et al., "Reversal of cisplatin resistance by the 1,4-benzothiazepine derivative, JTV-519," Jpn. J. Cancer Res., vol. 92, pp. 597-602 (2001).
Ondrias, et al., "FKBP12 modulates gating of the ryanodine receptor/calcium release channel," Ann. N.Y. Acad. Sci., vol. 853, pp. 149-156 (1998).

Ondrias, et al., Single channel properties and calcium conductance of the cloned expressed ryanodine receptor/calcium-release channel, Soc. Gen. Physiol. Serv., vol. 51, pp. 29-45 (1996).

Paul-Pletzer, et al., "Identification of a dantrolene-binding sequence on the skeletal muscle ryanodine receptor," J. Biol. Chem., vol. 277, pp. 34918-34923 (2002).

Rosemblit, et al., "Intracellular calcium release channel expression during embryogenesis," Dev. Biol., vol. 206, pp. 163-177 (1999).

Shtifman, et al., "Interdomain interactions within ryanodine receptors regulate Ca2+ spark frequency in skeletal muscle," J. Gen. Physiol., vol. 119, pp. 15-31 (2002).

Tester, et al., "Compendium of cardiac channel mutations in 541 consecutive unrelated patients referred for long QT syndrome genetic testing," Heart Rhythm. vol. 2, pp. 507-517 (2005).

Tester, et al., "Targeted mutational analysis of the RyR2-encoded cardiac ryanodine receptor in sudden unexplained death: a molecular authopsy of 40 medical examiner/coroner's cases," May Clin. Proc., vol. 79, pp. 1380-1384 (2004).

Timerman, et al., "The ryanodine receptor from canine heart sarcoplasmic reticulum is associated with a novel FK-506 binding protein," Biochem. Biophys. Res. Commun., vol. 198, pp. 701-706 (1994).

Tipton, et al., "My child just fainted: no big deal or sudden-death warning?" Emerg. Med. Serv., vol. 33, pp. 41-45 (2004).

Wang, et al., "Retinoic acid stimulates annexin-mediated growth plate chondrocyte mineralization," J. Cell Biol., vol. 157, pp. 1061-1069 (2002).

Wang, W., et al., "Annexin-mediated Ca2+ influx regulates growth plate chondrocyte maturation and apoptosis," J. Biol Chem, vol. 278, pp. 3762-3769 (2003).

Ward, et al., "Defects in ryanodine receptor calcium release in skeletal muscle from post-myocardial infarct rats," Faseb J., vol, 17, pp. 1517-1519 (2003).

Wehrens, et al., "Altered function and regulation of cardiac ryanodine receptors in cardiac disease," Trends Biochem. Sci., vol. 28, pp. 671-678 (2003).

Wehrens, et al., "Myocardial disease in failing hearts: defective excitation-contraction coupling," Cold Spring Harb. Symp. Quant. Biol., vol. 67, pp. 533-541 (2002).

Yamamoto, et al., "Ca2+-dependent dual function of peptice C. The peptide corresponding to the Glu724-Pro760 region (the so-called determinant of excitation-contraction coupling) of the dihydropyridine receptor alpha 1 subunit II-III loop," J. Biol. Chem., vol. 277, pp. 993-1001 (2002).

Yamamoto, et al., "Peptide probe study of the critical regulatory domain of the cardiac ryanodine receptor," Biochem, Biophys. Res. Commun., vol. 291, pp. 1102-1108 (2002).

Yamamoto, et al., "Spectroscopic monitoring of local conformational changes during the intramolecular domain-domain interaction of the ryanodine receptor," Biochemistry, vol. 41, pp. 1492-1501 (2002).

Marks, AR, "Arrhythmias of the heart: beyond ion channels," Nat. Medicine, vol. 9, pp. 263-264, (2003).

Marks, AR, "Calcium and the heart: a question of life and death," J. Clin. Investigation, vol. 111, pp. 597-600, (2003).

Manzur, et al., "A severe clinical and pathological variant of central core disease with possible autosomal recessive inheritance," Neur. Disorders, vol. 8, pp. 467-473 (1998).

Swan, et al., "Calcium channel antagonism reduces exercise-induced ventricular arrhythmias in catecholaminergic polymorphic ventricular tachycardia patients with RyR2 mutations," J. of Card. Electrophysiology, vol. 16, No. 2, pp. 162-166, (2005).

Culligan, et al., "Drastic reduction of calsequestrin-like proteins and impaired calcium binding in dystrophic mdx muscle," J. Appl. Physiol., vol. 92, pp. 435-445 (2002).

Dorian, P., "Antiarrhythmic action of beta-blockers: potential mechanisms," J. Cardiovasc. Pharmacol. Therapeut., vol. 10, pp. S15-S22 (2005).

Morita, et al., "Ca channel blocking activity of JTV-519, a novel protective drug to cytotoxicity," Neuroscience Research, vol. 31, Supp. 1, p. S65 (1998).

Ishii, et al., "JTV-519, a new cardioprotective drug, and cariporide, synergistically improved post-ischemic contractile recovery in rat," Journal of Molecular and Cellular Cardiology, vol. 35, Issue 6, p. A29 (2002).

Lee, et al., "Sudden unexplained death: evaluation of those left behind," The Lancet, vol. 362, pp. 1429-1431 (2003).

Behr, et al., "Cardiological assessment of first-degree relatives in sudden arrhythmic death syndrome," The Lancet, vol. 362, 1457-1459 (2003).

Yamamoto, et al., "T-tubule depolarization-induced local events in the ryanodine receptor, as monitored with the fluorescent conformational probe incorporated by mediation of peptide A," J. Biol. Chem. vol. 277, pp. 984-992 (2002).

Wang, ZG et al., "Effects of Flecainide and Quinidine on Human Atrial Action Potentials. Role of rate-dependence and comparison with guinea pig, rabbit, and dog tissues," Circulation, Journal of the American Heart Association, vol. 82, pp. 274-283. 1990.

Echt et al., "Mortality and morbidity in patients receiving encainide, flecainide, or placebo," The Cardiac Arrhythmia Suppression Trial, N. Engl. J. Med., vol. 324, pp. 781-788. (1991).

Schotten et al., "Electrical and contractile remodeling during the first days of atrial fibrillation go hand in hand," Circulation, vol. 107, pp. 1433-1439. (2003).

Shiroshita-Takeshita et al., "Atrial fibrillation: basic mechanisms, remodeling and triggers," J. Interv. Card. Electrophysiol, vol. 13, pp. 181-193. (2005).

Stevenson, W.G. et al., "Sudden death prevention in patients with advanced ventricular dysfunction," Circulation, vol. 88, pp. 2953-2961. 1993.

Wilde et al., "Ion Channels, the QT interval, and arrhythmias," Pacing Clin Electrophysiol, vol. 20, pp. 2048-2051. 1997.

Harrison's Principles of Internal Medicine, 13th edition, vol. 1, published 1994 by McGraw-Hill, Inc. (NY), pp. 1022-1024.

U.S. Appl. No. 10/763,498, filed Jan. 22, 2004, Marks et al.

Ahern et al., "Intramembrane Charge Movements and Excitation-Contraction Coupling Expressed by Two-Domain Fragments of the Ca2+ Channel." Proc Natl Acad Sci USA, vol. 98, No. 12, pp. 6935-6940. (2001).

Ahern et al., "Subconductance States in Single-Channel Activity of Skeletal Muscle Ryanodine Receptors After Removal of FKBP12." Biophys J, vol. 72, pp. 146-162. (1997).

Ahmmed, G.U. et al., "Changes in Ca(2+) Cycling Proteins Underlie Cardiac Action Potential Prolongation in a Pressure-Overloaded Guinea Pig Model with Cardiac Hypertrophy and Failure." Circ. Res., vol. 86, No. 5, pp. 558-570. (2000).

Baille, et al., "beta-Arrestin-mediated PDE4 cAMP phosphodiesterase recruitment regulates beta-adrenoceptor switching from Gs to Gi," Proc. Natl. Acada. Sci. USA 100, 940-945 (2003).

Barnes, P.J., "Theophylline: new perspectives for an old drug," Am. J. Respir. Crit. Care Med. 167, 813-8 (2003).

Basso, C. et al., "Arrhythmogenic Right Ventricular Cardiomyopathy Causing Sudden Cardiac Death in Boxer Dogs: A New Animal Model of Human Disease." Circulation, vol. 109, No. 9, pp. 1180-1185. (2004).

Bennett et al., "Synthesis of 2-methoxydibenzo [b,f](1,4)-thiazepin-11 (10H)-one 5,5-dioxide." Organic Preparations and Procedures International, vol. 6, No. 6, pp. 287-293. (1974).

Bezprozvanny, I. et al. "Bell-shaped Calcium Response Curves of Ins (1,4,5) $P_3$- and Calcium-gated Channels from Endoplasic Reticulum of Cerebellum." Nature, vol. 351, pp. 751-754. (1991).

Bittar, et al., "The arrhythmogeneicity of theophylline. A multivariate analysis of clinical determinants," Chest 99, 1415-1420 (1991).

Bohm, M. et al. "cAMP Concentrations, cAMP Dependent Protein Kinase Activity, and Phospholamban in Non-Failing and Failing Myocardium." Cardivasc. Res., vol. 28, No. 11, pp. 1713-1719. (1994).

Bolger, et al., "Characterization of five different proteins produced by alternatively spliced mRNAs from the human cAMP-specific phosphodiesterase PDE4D gene," Biochem. J. 328 (Pt 2), 539-48 (1997).

Boyden et al., "2APB- and JTV519 (K201)—Sensitive Micro $Ca^{2+}$ Waves in Arrythmogenic Purkinje Cells that Survive in Infarcted Canine Heart." Heart Rhythm, vol. 1, pp. 218-226. (2004).

Bristow et al., "Carvedilol Produces Dose-Related Improvements in left Ventricular Function and Survival in Subjects with Chronic Heart Failure." Circulation, vol. 94, pp. 2807-2816. (1996).

Bristow, et al., "Beta 1- and beta 2-adrenergic-receptor subpopulations in nonfailing and failing human ventricular myocardium: coupling of both receptor subtypes to muscle contraction and selective beta I-receptor down-regulation in heart failure," Circ. Res. 59, 297-309 (1986).

Bristow, Michael R. et al. "β-Adrenergic Neuroeffector Abnormalities in the Failing Human Heart are Produced by Local Rather Than Systemic Mechanisms." J. Clin. Invest., vol. 89, pp. 803-815 (Mar. 1982).

Callaway, C. et al., "Localization of the High and Low Affinity [$^3$H] Ryanodoine Binding Sites on the Skeletal Muscle $Ca^{2+}$ Release Channel." The Journal of Biological Chemistry, vol. 269, No. 22, pp. 15876-15884. (1994).

Carlisle Michel, et al., "PKA-phosphorylation of PDE4D3 facilitates recruitment of the mAKAP signaling complex," Biochem. J. 381, 587-592 (2004).

Catsoulacos, "Synthesis of Substituted Dihydrobenzothiazepines and Related Compounds." J Heterocyclic Chemistry, vol. 7, No. 2: pp. 409-411. (1970).

Cerrone, M. et at "Bidirectional Ventricular Tachycardia and Fibrillation Elicited in a Knock-in Mouse Model Carrier of a Mutation in the Cardiac Ryanodine Receptor." Circ. Res., vol. 96, No. 10, e77-82. (2005).

Cheng, H. et al., "Amplitude Distribution of Calcium Sparks in Confocal Images: Theory and Studies with an Automatic Detection Method." Biophys J., vol. 76, pp. 606-617. (1999).

Cohn, Cohn, J.N. et al. "Plasma Norepinephrine as a Guide to Prognosis in Patients with Chronic Congestive Heart Failure." N. Eng. J. Med., vol. 311, No. 13, pp. 819-823 (1984).

Conti, et al., "Cyclic AMP-specific PDE4 phosphodiesterases as critical components of cyclic AMP signaling," J. Biol. Chem. 278, 5493-6 (2003).

Dietz et al., "Epinephrine Regulation of Skeletal Muscle Glycogen Metabolism :Studies Utilizing the Perfused Rat Hindlimb Preparation." J. Biol. Chem., vol. 255, No. 6, pp. 2301-2307. (1980).

Dodge K.L., et al. "mAKAP Assembles a Protein Kinase A/PDE4 Phosphodiesterase cAMP Signaling Module." EMBO J. vol. 20, No. 8, pp. 1921-1930. (2001).

Doi et at "Propranolol prevents the Development of Heart Failure by Restoring FKBP12.60-Mediated Stabilization of Ryanodine Receptor." Circulation vol. 105, pp. 1374-1379. (2002).

Drexler et al. "Contrasting Peripheral Short-Term and Long-Term Effects of Coverting Enzyme Inhibition in Patients with Congestive Heart Failure. A Double-Blind, Placebo-Controlled Trial." Circulation, vol. 79, pp. 491-502. (1989).

Feldman, et al., "Deficient production of cyclic AMP: pharmacologic evidence of an important cause of contractile dysfunction in patients with end-stage heart failure," Circulation 75, 331-9 (1987).

Fisher, J.D. et al. "Familial Polymorphic Ventricular Arrhythmias: A Quarter Century of Successful Medical Treatment Based on Serial Exercise-Pharmacologic Testing." J. Am. Coll. Cardiol., vol. 34, No. 7, pp. 2015-2022. (1999).

Fodor et al. "New Convenient Synthesis of 1,4-benzothiazepines." Tetrahedron Letters, vol. 36, No. 5, pp. 753-756. (1995).

Fox, P.R., "Spontaneously Occurring Arrhythmogenic Right Ventricular Cardiomyopathy in the Domestic Cat: A New Animal Model Similar to the Human Disease." Circulation, vol. 102, No. 15, pp. 1863-1870. (2000).

Franzen, P. et al. "Cloning of a TGFβ Type I Receptor That Forms a Heteromeric Complex with the TGF beta type II receptor." Cell, vol. 75, pp. 681-692. (1993).

Franzini-Armstrong et al., "Alternate Disposition of Tetrads in Peripheral Couplings of Skeletal Muscle." Journal of Muscle Research & Cell Motility. vol. 16, pp. 319-324. (1995).

Fraser, I.D. et al. "Modulation of Ion Channels: a "current" view of AKAPs." Neuron, vol. 23, pp. 423-426. (1999).

Frazier, O.H. et al. "First Use of an Untethered, Vented Electrc Left Ventricular Assist Device for Long-Term Support." Circulation, vol. 89, pp. 2908-2914. (1994).

Gaburjakova, M. et al. "FKBP12 Binding Modulates Ryanodine Receptor Channel Gating." J. Biol. Chem., vol. 276, No. 20, pp. 16931-16935. (2001).

Giembycz, M.A., "Development status of second generation PDE4 inhibitors for asthma and COPD: the story so far," Monaldi, Arch. Chest Dis. 57, 48-64 (2002).

Go, Loewe O. et al., "Differential Regulation of Two Types of Intracellular Calcium Release Channels during End-Stage Heart Failure." J. Clin. Invest., vol. 95, pp. 888-894. (Feb. 1995).

Goette et al. "Electrical Remodeling in Atrial Fibrillation: Time Course and Mechanisms." Circulation, vol. 94, pp. 2968-2974. (1996).

Gong, et al., "Persistent improvement in synaptic and cognitive functions in an Alzheimer mouse model after rolipram treatment," J. Clin. Invest. 114, 1624-1634 (2004).

Gonzalez et al. "Involvement of Multiple Intracellular Release Channels in Calcium Sparks of Skeletal Muscle." Proc. Natl Acad Sci USA, vol. 97, No. 8, pp. 4380-4385. (2000).

Gretarsdottir, et al., "The gene encoding phosphodiesterase 4D confers risk of ischemic stroke," Nat. Genet. 35, 131-8 (2003).

Gullestad et al., "Effect of Metoprolol CR/XL on Exercise Tolerance in Chronic Heart Failure—a Substudy to the MERIT-HF Trial," Eur. J. Heart Fail, vol. 3, pp. 463-468. (2001).

Hachida et al. "Protective effect of JTV519 on Prolonged Myocardial Preservation." Transplant Proc., vol. 31, pp. 1094. (1999).

Hachida et al. "Significant Effect of 1,4-Benzothiazepine Derivative (K2) in Improving Myocardial Preservation." Transplantation Proceedings, vol. 29, pp. 1346-1348. (1997).

Hachida, et al., "Protective Effect of JTV519 (K201), a New 1, 4—Benzothiazepine Derivative, on Prolonged Myocardia Preservation." Transplantation Proceedings, vol. 31, pp. 996-1000. (1999).

Hachida, M. et al. "Protective Effect of JTV-519, a new 1, 4-Benzothiazepine Derivative, on Prolonged Myocardial Preservation." J. Card. Surg., vol. 14, pp. 187-193. (1999).

Harnick, D.J. et al. "The Human Type 1 Inositol 1,4,5-trisphosphate receptor from T Lymphocytes: Structure, Localization, and Tyrosine Phosphorylation." J. Biol. Chem., vol. 270, No. 6, pp. 2833-2840. (1995.).

Harrington, D. et al. "Mechanisms of Exercise Intolerance in Congestive Heart Failure." Current Opinion in Cardiology, vol. 12, No. 3, pp. 224-232. (1997).

Hasenfuss et al., "Treatment of Heart Failure Through Stabilization of the Cardiac Ryanodine Receptor." Circulation, vol. 107, pp. 378-380. (2003).

Houslay, et al., "PDE4 cAMP phosphodiesterases: modular enzymes that orchestrate signaling cross-talk, desensitization and compartmentalization," Biochem. J. 370, 1-8 (2003).

Huse, M. et al. "Crystal Structure of the Cytoplasmic Domain of the Type 1 TGFβ Receptor in Complex With FKBP12." Cell, vol. 96, pp. 425-436. (1999).

Inagaki et al. "Anti-ischemic Effect of a Novel Cardioprotective Agent, JTV 519, is mediated through Specific Activation of δ-lsoform of Protein Kinase C in Rat Ventricular Myocardium." Circulation, vol. 101, pp. 797-804. (2000).

Inagaki et al. "The Cardioprotective Effects of a new 1,4-benzothiazepine Derivative, JTV 519, on ischemia/reperfusion-induced Ca2+ Overload in Isolated Rat Hearts." Cardiovasc Drugs Ther., vol. 14, pp. 489-495. (2000).

Ito et al. "JTV-519, a Novel Cardioprotective Agent, Improves the Contractile Recovery after Ischaemia Reperfusion in Coronary Perfused Guinea Pig Ventricular Muscles." Br. J. Pharmacol., vol. 130, No. 4, pp. 767-776. (2000).

Jayaraman, T. et al. "Regulation of the Inositol 1,4,5-Trisphosphate Receptor By Tyrosine Phosphorylation." Science, vol. 272, pp. 1492-1494. (1996.).

Jiang et al., "Abnormal $Ca^{2+}$ Release, but Normal Ryanodine Receptors, in Canine and Human Heart Failure." Circulation Research, vol. 91, pp. 1015-1022. (Nov. 29, 2002).

Jiang, D. et al. "Enhanced Basal Activity of a Cardiac $Ca^{2+}$ Release Channel (Ryanodine Receptor) Mutant Asssociated with Ventricular Tachycardia and Sudden Death." Circ. Res., vol. 91, pp. 218-225. (2002).

Jin, S.L.C. et al.: "Impaired growth and fertility of cAMP-specific phosphodiesterase PDE4D-deficient mice," PNAS, Oct. 12, 1999, vol. 96, No. 21, 11998-12003.

Kaneko et al., "Crystal Structure of Annexin V with Its Ligand K-201 as a Calcium Channel Activity Inhibitor." Journal of Molecular Biology, vol. 274, pp. 16-20. (1997).

Kaneko et al., "Inhibition of Annexin V-dependent Ca2 Movement in Large Unilamellar Vesicles by K201, a New." Biochimica et Biophysica Acta, vol. 1330, pp. 1-7. (1997).

Kaneko, N. "New 1,4-benzothiazepine Derivative, K201, Demonstrates Cardio-Protective Effects Against Sudden Cardiac Cell Death and Intracellular Calcium Blocking Action." Drug Dev. Res., vol. 33: pp. 429-438 (1994).

Kapiloff, M.S. et al. "mAKAP:an A-kinase Anchoring Protein Targeted to the Nuclear Membrane of Differentiated Myocytes." J. Cell Sci., vol. 112, pp. 2725-2736. (1999).

Kapiloff, M.S. et al.: "mAKAP and the ryanodine receptor are part of a multi-component signaling complex on the cardiomyocyte nuclear envelope," Journal of Cell Science, 114, 3167-3176 (2001).

Katritzky, et al., "1H and 13C NMR study of tetrahydro-1, 4-benzothiazepine conformations," J. Chem. Soc. 5, 1816-1822 (2002).

Katritzky, et al., Convenient syntheses of 2, 3, 4, 5-tetrahydro-1, 4-benzothiazepines, -1, 4-benzoxazepines and -1, 4-benzodiazepines, J. Chem. Soc. 11, 592-598 (2002).

Katz et al., "Lactate Turnover at Rest and During Submaximal Excercise in Patients with Heart Failure." J. Appl. Physiol., vol. 75, No. 5, pp. 1974-1979. (1993).

Kawabata et al. "A Novel Cardioprotective Agent, JTV-519, is abolished by Nitric Oxide Synthase Inhibitor on Myocardial Metabolism in Ischemia-Reperfused Rabbit Hearts." Hypertens Res., vol. 25, pp. 303-309. (2001).

Kawabata et al. "Effect of a Novel Cardioprotective Agent, JTV-519, on Metabolism, Contraction and Relaxation in the Ischemia-Reperfused Rabbit Heart." Jpn Circ. J., vol. 64, pp. 772-776. (2000).

Kimura, J. et al. "Effects of a Novel Cardioprotective Drug, JTV-519 on Membrane Currents of Guinea Pig Ventricular Myocytes." Jpn. J. Pharmacol., vol. 79, pp. 275-281. (1999).

Kirchhefer, U. et al. "Activity of cAMP-dependent Protein Kinase and $Ca^{2+}$/calmodulin-dependent Protein Kinase in Failing and Nonfailing Human Hearts." Cardiovasc. Res., vol. 42, pp. 254-261 (1999).

Kiriyama et al. "Effects of JTV-519, a Novel Anti-Ischaemic Drug, on the Delayed Rectifier K+ Current in Guinea-Pig Ventricular Myocytes." Naunyn Schmiedebergs Arch Pharmacol. vol. 361, No. 6, pp. 646-653. (2000).

Kirsch et al., "Spark and Ember-Like Elementary $Ca^{2+}$ Release Events in Skinned Fibre of Adult Mammalian Skeletal Muscle." J. Physiol., vol. 537, No. 2, pp. 379-389. (2001).

Kiryu, K. et al. "Pathologic and Electrocardiographic Findings in Sudden Cardiac Death in Racehorses." J. Vet. Med. Sci., vol. 61, No. 8, pp. 921-928. (1999).

Kittleson, M.D. et al., "Familial Hypertrophic Cardiomyopathy in Maine Coon Cats: An Animal Model of Human Disease." Circulation, vol. 99, No. 24, pp. 3172-3180. (1999).

Klein et al., "Voltage Dependence of the Pattern and Frequency of Discrete $Ca^{2+}$ Release Events After Brief Repriming in Frog Skeletal Muscle." Proc. Natl. Acad. Sci. USA, vol. 94, pp. 11061-11066. (1997).

Kukin, M.L. et al: "Prospective, Randomized Comparison of Effect of Long-Term Treatment with Metoprolol or Carvedilol on Symptoms, Excercise, Ejection Fraction, and Oxidative Stress in Heart Failure." Circulation, vol. 99, pp. 2645-2651. (1999).

Lacampagne, A. et al., "Modulation of the Frequency of Spontaneous Sarcoplasmic Reticulum $Ca^{2+}$ Release Events ($Ca^{2+}$ Sparks) by Myoplasmic ($Mg^{2+}$) Frog Skeletal Muscle." J. Gen. Physiol. 111, pp. 207-224. (1998).

Laflamme, M.A. et al. "Gs and Adenylyl Cyclase in Transverse Tubules of Heart: Implications for cAMP-dependent signaling." Am. J. Phys., vol. 277, pp. H1841-H1848. (1999).

Lai, F.A., et al., "The Ryanodine Receptor-$Ca^{2+}$ Release Channel Complex of Skeletal Muscle Sarcoplasmic Reticulum. Evidence for a Cooperatively Coupled, Negatively Charged Homotetramer." J. Biol. Chem., vol. 264, No. 28, pp. 16776-16785. (1989).

Lamb et al., "Effects of FK506 and Rapamycin on Excitation-Contraction Coupling in Skeletal Muscle Fibres of the Rat." J Phys, vol. 494, No. 2, pp. 569-576. (1996).

Lauffenburger et al. , "Receptors." Oxford University Press, Chapter 2, pp. 9-12. (1996).

Laver et al., "Inactivation of $Ca^{2+}$ Release Channels (Ryanodine Receptors RyR1 and RyR2) with Rapid Steps in [$Ca^{2+}$] and Voltage." Biophys J., vol. 74, pp. 2352-2364. (1998).

Lehnart et al. "Cardiac Ryanodine Receptor Function and Regulation in Heart Disease." Ann NY Acad Sci., vol. 1015, pp. 144-159. (2004).

Lehnart et al. "Defective Ryanodine Receptor Interdomain Interactions May Contribute to Intracellular $Ca^{2+}$ Leak: A Novel Therapeutic Target in Heart Failure." Circulation, vol. 111, No. 25, pp. 3342-3346. (2005).

Lehnart et al., "Phosphodiesterase 4D Deficiency in the Ryanodine-Receptor Complex Promotes Heart Failure and Arrhythmias." Cell, vol. 123, No. 1, pp. 25-35. (Oct. 7, 2005).

Lehnart et al., "Sudden Death in Familial Polymorphic Ventricular Tachycardia Associated with Calcium Release Channel (Ryanodine Receptor) Leak." Circulation, vol. 109, pp. 3208-3214. (2004).

Levin, H.R. et al. "Reversal of Chronic Ventricular Dilation in Patients with End-Stage Cardiomyopathy by Prolonged Mechanical Unloading." Circulation, vol. 91, pp. 2717-2720. (1995).

Lisy et al., "New Cardioprotective Agent K201 is Natriuretic and Glomerular Filtration Rate Enhancing." Circulation, vol. 113, pp. 246-251. (2006).

Lorenz, M.C. et al. "TOR Mutations Confer Rapamycin Resistance by Preventing Interaction with FKBP12- Rapamycin." J. Biol. Chem., vol. 270, No. 46, pp. 27531-27537. (1995).

Lunde et al., "Contraction and Intracellular Ca2+ Handling in isolated Skeletal Muscle of Rats with Congestive Heart Failure." Circ. Res., vol. 88, pp. 1299-1305. (2001).

Lunde, et al. "Contractile Properties of in Situ Perfused Skeletal Muscles from Rats with Congestive Heart Failure." J. Physiol, vol. 540, pp. 571-580. (2002).

MacDougall, L.K. et al. "Identification of the Major Protein Phosphatases in Mammalian Cardiac Muscle Which Dephosphorylate Phospholamban." Eur. J. Biochem., vol. 196, pp. 725-734. (1991).

MacFarlane et al. "Cellular Basis for Contractile Dysfunction in the Diaphragm from a Rabbit Infarct Model of Heart Failure." Am. J. Physiol. Cell Physiol., vol. 278. pp. C739-C746. (2000).

Mancini et al., "Contribution of a Skeletal Muscle Atrophy to Exercise Intolerance and Altered Muscle Metabolism in Heart Failure." Circulation, vol. 85, pp. 1364-1373 (1992).

Marks et al. "Clinical Implications of Cardiac Ryanodine Receptor/Calcium Release Channel Mutation Linked to Sudden Cardiac Death." Circulation, vol. 106, p. 8-10. (Jul. 2, 2002).

Marks et al. "Involvement of the Cardiac Ryanodine Receptor/Calcium Release Channel in Catecholaminergic Polymorphic Ventricular Tachycardia." J. Cell. Physiol., vol. 190, pp. 1-6. (Jan. 2002).

Marks et al. "Ryanodine Receptors, FKBP12, and Heart Failure." Frontiers in Bioscience, vol. 7, pp. 970-977. (2002).

Marks et al., "A Guide for the Perplexed: Towards an Understanding of the Molecular Basis of Heart Failure." Circulation. vol. 107, pp. 1456-1459. (2003).

Marks, A.R. et al. "Involvement of the Cardiac Ryanodine Receptor/Calcium Release Channel in Catecholaminergic Ventricular Tachycardia (Familial Polymorphic Ventricular Tachycardia)" J. Cellular Physiology, vol. 190, pp. 1-6. (2001).

Marks, Andrew. "Ryanodine Receptors/Calcium Release Channels in Heart Failure and Sudden Cardiac Death," Journal of Molecular Cell Cardiology, vol. 33, pp. 615-624. (2001).

Marx et al. "Beta-Adrenergic Receptor Modulation of the KCNQ1/KCNE1 Potassium Channel Requires a Macromolecular Signaling Complex." Science, vol. 295, pp. 495-499. (2002).

Marx S.O et al., "Regulation of the Ryanodine Receptor in Heart Failure." Basic Res. Cardiol., vol. 97, Suppl. 1, pp. 1/49-1/51. (2002).

Marx, S.O. "Requirement of a Macromolecular Signaling Complex for β Adrenergic Receptor Modulation of the KCNQ1-KCNE1 Potassium Channel." Science, vol. 295, pp. 496-499. (2002).

Marx, S.O. et al. "Phosphorylation-dependent Regulation of Ryanodine Receptors: A Novel Role for Leucine/Isoleucine Zippers." J. Cell. Biol., vol. 153, No. 4, pp. 699-708. (2001).

Marx, Steven O. et al. "Coupled Gating Between Individual Skeletal Muscle Ca2+ Release Channels (Ryanodine Receptors)." Science, vol. 281, pp. 818-821. (Aug. 7, 1998).

Masumiya et al., "Localization of the 12.6 kDa FK506-binding Protein (FKBP12.6) Binding Site to the $NH_2$- Terminal Domain of the Cardiac $Ca^{2+}$ Release Channel. (Ryanodine Receptor)." The Journal of Biological Chemist, vol. 278, pp. 3786-3792. 2003.

McCartney, S. et al. "Cloning and Characterization of A-Kinase Anchor Protein 100 (AKAP100). A Protein That Targets A-Kinase to the Sarcoplasmic Reticulum." J. Biol. Chem., vol. 270, No. 16, pp. 9327-9333. (1995).

Meissner, G., "Ryanodine Receptor/$Ca^{2+}$ Release Channels and Their Regulation by Endogenous Effectors." Annu. Rev. Physiol., vol. 56, pp. 485-508. (1994).

Merit, H.F. "Effect of Metoprolol CR/XL in Chronic Heart Failure: Metoprolol CR/XL Randomised Intervention Trial in Congestive Heart Failure (Merit-HF)." Lancet, vol. 353, pp. 2001-2007. (1999).

Meurs, K.M. et al., "A Cardiac Myosin Binding Protein C Mutation in the Maine Coon Cat with Familial Hypertrophic Cardiomyopathy." Hum Mol Genet, vol. 14, No. 23, pp. 3587-3593. (2005).

Meurs, KM. "Boxer Dog Cardiomyopathy: An Update." Vet Clin North Am Small Anim Pract., vol. 34, pp. 1235-1244. (2004).

Miller, K.B., "Manganese Alters Mitochodrial Integrity in the Hearts of Swine Marginally Deficient in Magnesium." Biofactors, vol. 20, No. 2, pp. 85-96. (2004).

Minotti et al., "Impaired Skeletal Muscle Function in Patients with Congestive Heart Failure. Relationship to Systemic Excercise Performance." J. Clin. Invest., vol. 88, pp. 2077-2082. (1991).

Mitchell, G.F. et al. "Measurement of Heart Rate and Q-T Interval in the Conscious Mouse." Am. J. Physiol., vol. 274, pp. H747-H751. (1998).

Moghadam, H.K. "Heritability of Sudden Death Syndrome and Its Associated Correlations to Ascites and Body Weight in Broilers." Br Poult Sci, vol. 46, No. 1, pp. 54-57. (2005).

Moise, N.S., "Inherited Arrhythmias in the Dog: Potential Experimental Models of Cardiac Disease." Cardiovasc Res, vol. 44, No. 1, pp. 37-46. (1999).

Mongillo, et al., "Fluorescence resonance energy transfer-based analysis of cAMP dynamics in live neonatal rat cardiac myocytes revelas distinct functions of compartmentalized phosphodiesterases," Cir. Res., 95, 67-75 (2004).

Morgan, J. et al. "Abnormal Intracellular Calcium Handling: A Major Cause of Systolic and Diastolic Dysfunction in Ventricular Myocardium from Patients with heart failure." Circulation, vol. 81 (Suppl. 3), pp. III21-III32. (1990).

Moschella, M.C. et al. : Inositol 1,4,5-trisphosphate Receptor Expression in Cardiac Myocytes. J. Cell. Biol., vol. 120, No. 5, pp. 1137-1146. (1993).

Nair, et al., "Synthesis and reactions of 1, 4-benzothiazepine derivatives." IJOCAP. 7(9), 862-5 (1969).

Nakai, et al., "Functional Nonequality of the Cardiac and Skeletal Ryanodine Receptors," Proc. Natl. Acad. Sci. USA, vol. 94, pp. 1019-1022, Feb. 1997.

Nakamura, Y. et al., "Parasitic Females of Strongyloides Papillosus as a Pathogenetic Stage for Sudden Cardiac Death in Infected Lambs." J. Vet Med. Sci., vol. 56, No. 4, pp. 723-727. (1994).

Nakaya et al. "Inhibitory Effects of JTV-519, a Novel Cardioprotective Drug, on Potassium Currents and Experimental Atrial Fibrillation in Guinea-Pig Hearts. British Journal of Pharmacology," vol. 131, pp. 1363-1372. (2000).

Neumann, J. et al. "Increased Expression of Cardiac Phosphatases in Patients with End-Stage Heart Failure." J. Mol. Cell. Cardiol., vol. 29, pp. 265-272. (1997).

Otsu, K. et al. "Molecular Cloning of cDNA encoding the $Ca^{2+}$ release channel (Ryanodine Receptor) of Rabbit Cardiac Muscle Sarcoplasmic Reticulum." J. Biol. Chem., vol. 265, No. 23, pp. 13472-13483. (1990).

Oyama, Mark A. et al., "Genomic Expression Patterns of Cardiac Tissues from Dogs with Dilated Cardiomyopathy." AJVR, vol. 66, No. 7, pp. 1140-1155. (Jul. 2005).

Packer, et al., "Effect of oral milrinone on mortality in severe chronic heart failure. The Promise Study Research Group," N. Engl. J. Med. 325, 1468-75 (1991).

Perreault et al., "Alterations in Contractility and Intracellular $Ca^{2+}$ Transients in Isolated Bundles of Skeletal Muscle Fibers from Rats with Chronic Heart Failure." Cir. Res., vol. 73, No. 2, pp. 405-412. (1993).

Perry, et al., "Targeting of cyclic AMP degradation to beta 2-adrenergic receptors by beta-arrestins," Science 298, 834-6 (2002).

Pieske, et al., "Ca2+ handling and sarcoplasmic reticulum Ca2+ content in isolated failing and nonfailing human myocardium," Circ. Res. 85, 38-46 (1999).

Pogwidz, S.M. et al. "Mechanisms Underlying Spontaneous and Induced Ventricular Arrhythmias in Patients with Idiopathic Dilated Cardiomyopathy." Circulation, vol. 98, pp. 2404-2414. (1998).

Pogwizd, S.M. et al. "Arrhythmogenesis and Contractile Dysfunction in Heart Failure: Roles of Sodium-Calcium Exchange, Inward Rectifier Potassium Current, and Residual Beta-Adrenergic Responsiveness." Circ. Res., vol. 88, pp. 1159-1167. (2001).

Protas, L. et al., "Regional Dispersion of L-type Calcium Current in Ventricular Myocytes of German Shepherd Dogs with Lethal Cardiac Arrhythmias." Heart Rhythm, vol. 2, Issue. 2, pp. 172-176. (2005).

Regitz-Zagrosek, et al. "Myocardial Cyclic AMP and Norepinephrine Content in Human Heart Failure." Eur. Heart J, 15 Suppl. D: pp. 7-13. (1994).

Reiken et al. "PKA Phosphorylation Activates the Calcium Release Channel (Ryanodine Receptor) in Skeletal Muscle: Defective Regulation in Heart Failure." J. Cell. Biol., vol. 160, No. 6, pp. 919-928. (2003).

Reiken et al. "Protein Kinase A Phosphorylation of the Cardiac Calcium Release Channel (Ryanodine Receptor) in Normal and Failing Hearts. Role of Phosphatases and Response to Isoproterenol." J. Biol. Chem., vol. 278, No. 1, pp. 444-453. (2003).

Reiken et al., "A Novel Excitation-Contraction (EC) Coupling Myopathy in Heart Failure Involving Both Cardiac and Skeletal Muscles." Circulation, vol. 104. No. 17 Supplement. pp. II.131. (Oct. 23, 2001).

Reiken et al., "Defective Skeletal Muscle Calcium Release Channel Function during Heart Failure." Circulation, vol. 106, No. 19 Supplement, pp. II-225. (2002).

Reiken, S. et al. "PKA Phosphorylation of the Cardiac Calcium Release Channel (Ryanodine Receptor) in Normal and Failing Hearts: Role of Phosphatases and Response to Isoproterenol." J. Biol. Chem. (2002).

Reiner, G. et al., "Skeletal Muscle Sarcoplasmic Calcium Regulation and Sudden Death Syndrome in Chickens." Br Poult Sci., vol. 36, No. 4, pp. 667-675. (1995).

Richter, et al., "Splice variants of the cyclic nucleotide phosphodiesterase PDE4D are differentially expressed and regulated in rat tissue," Biochem. N. 388, 803-811 (2005).

Rios et al., "Charge Movement and the Nature of Signal Transduction in Skeletal Muscle Excitation-Contraction Coupling." Annu Rev Physiol, vol. 54, pp. 109-133. (1992).

Rios et al., "Involvement of Dihydropyridine Receptors in Excitation-Contraction Coupling in Skeletal Muscle." Nature, vol. 325, pp. 717-720. (1987).

Ruehr, et al., "Targeting the protein kinase A by muscle A kinase-anchoring protein (mAKAP) regulates phosphorylation and function of the skeletal muscle ryanodine receptor," J. Biol. Chem. 278, 24831-24836 (2003).

Schneider et al., "Voltage Dependent Charge Movement in Skeletal Muscle: A Possible Step in Excitation-Contraction Coupling." Nature, vol. 242, pp. 244-246. (1973).

Schoenmakers et al., "Chelator: An Improved Method for Computing Metal Ion Concentrations in Physiological Solutions." Biocomputing, vol. 12, pp. 870-879. (1992).

Sen, L.Y. et al. "Inotropic and Calcium Kinetic Effects of Calcium Channel Agonist and Antagonist in Isloated Cardiac Myocytes from Cardiomyopathic Hamsters." Circ Res, vol. 67, No. 3, pp. 599-608. (1990).

Sette, et al., "Phosphorylation and activation of a cAMP-specific phosphodiesterase by the cAMP-dependent protein kinase. Involvement of serine 54 in the enzyme activation," J. Biol. Chem. 271, 16526-34 (1996).

Sette, et al., "The ratPDE3/Ivd phosphodiesterase gene codes for multiple proteins differentially activated by cAMP-dependent protein kinase," J. Biol. Chem. 269, 18271-4 (1994).

Shannon, et al., "Elevated sarcoplasmic reticulum Ca2+ leak in intact ventricular myocytes from rabbits in heart failure," Circ. Res. 93, 592-4 (2003).

Shibata, "264 W94" Current Opinion in Cardiovascular, Pulmonary, and Renal Investigational Drugs., vol. 1, No. 2, pp. 276-278. (1999).

Shinohara, "A Synthesis of Mono-and Dimethoxy -1,2,3,4-Tetrahydroisoquinolines via Pummerer Reaction: Effects of Methoxyl Groups on Intramolecular Cyclization." Chemical and Pharmaceutical Bulletin, vol. 46, No. 6, pp. 918-927. (1998).

Shirokova, N. et al., "Local Calcium Release in Mammalian Skeletal Muscle." J. Physiol, vol. 512, No. 2, pp. 377-384. (1998).

Shou, W. et al. "Cardiac Defects and Altered Ryanodine Receptor Function in Mice Lacking FKBP12." Nature, vol. 391, pp. 489-492. (1998).

Sonnleitner et al., "Gating of the Skeletal Calcium Release Channel by ATP is Inhibited by Protein Phosphatase 1 but not by $Mg^{2+}$," Cell Calcium 21, No. 4, pp. 283-290. (1997).

Sorensen et al., "Excercised Blood Flow and Microvascular Distensibility in Skeletal Muscle Normalize After Heart Transplantation." Clin. Transplant, vol. 13, pp. 410-419. (1999).

Stratton et al., "Effects of Cardiac transplantation on Bioenergetic Abnormalities of Skeletal Muscle in Congestive Heart Failure." Circulation, vol. 89, pp. 1624-1631. (1994).

Suissa, et al., "Bronchodilators and acute cardiac death," Am. J. Respir. Crit. Care Med. 154, 1598-1602 (1996).

Suko et al., "Phosphorylation of Serine 2843 in Ryanodine Receptor-Calcium Release Channel of Skeletal Muscle by cAMP-, cGMP- and CaM-Dependent Protein Kinase." Bioch Biophys. Acta., vol. 1175, pp. 193-206. (1993).

Sullivan et al., "Exercise Intolerance in Patients with Chronic Heart Failure." Prog. Cardiovasc. Dis., vol. 38, No. 1, pp. 1-22. (1995).

Szabo et al. "Synthesis and Spectroscopic Investigation of 1,4-Benzothiazepine Derivatives." Magyar Kemiai Folyoirat, vol. 93, No. 6. pp. 269-276. (1987). (in Hungarian and English).

Szabo et al. "Synthesis and Transformation of 4,5-dihydro-1,4-benzothiazepin-3(2H)—one derviatives." Magyar Kemiai Folyoirat, vol. 93, No. 3, pp. 139-144. (1987). (in Hungarian and English).

Takeshima, H. et al. "Primary Structure and Expression from Complementary DNA of Skeletal Muscle Ryanodine Receptor." Nature, vol. 339, pp. 439-445. (1989).

Tanabe, T. et al., "Regions of the Skeletal Muscle Dihydropyridine Receptor Critical for Excitation-Contraction Coupling." Nature, vol. 346, pp. 567-569. (1990).

Tasken, et al., "Phosphodiesterase 4D and protein kinase a type li constitute a signaling unit in the centrosomal area," J. Biol. Chem. 276, 21999-2002 (2001).

Timerman, Anthony P. et al., "The Calcium Release Channel of Sarcoplasmic Reticulum is Modulated by FK-506- binding Protein." J. Bio. Chem., vol. 268, No. 31, pp. 22992-22999. (1993).

Tse et al. "JTV-519 Japan Tobacco." Curr. Opin. Investig. Drugs. vol. 2, No. 7, pp. 936-939. (2001).

Tsuji, N. et al., "Sudden Cardiac Death in Calves with Experimental Heavy Infection of Strongyloides Papillosus." J. Vet. Med. Sci., vol. 54, No. 6, pp. 1137-1143. (1992).

Tunwell et al., "*H. sapiens* mRNA for Ryanodine Receptor 2." GenBank Database, Accession No. X98330. Sep. 9, 1996.

Tunwell et al., "The Human Cardiac Muscle Ryanodine Receptor-Calcium Release Channel: Identification, Primary Structure and Topological Analysis." Biochem. J., vol. 318, pp. 477-487. (1996).

van Rooij, et al., "MCIPl overexpression suppresses left ventricular remodeling and sustains cardiac function after mycardial infarction," Circ. Res. 94, e18-26 (2004).

Verde, et al., "Characterization of the cyclic nucleotide phosphodiesterase subtypes involved in the regulation of the L-type Ca2+ current in rat ventricular myocytes," Br. J. Pharmacol. 127, 65-74 (1999).

Vest, J.A. et al., "Defective Cardiac Ryanodine Receptor Regulation During Atrial Fibrillation." Circulation. vol. 111, No. 16, pp. 2025-2032. (2005).

Vignola, A.M., "PDE4 inhibitors in COPD—a more sselective approach to treatment,". Respir. Med. 98, 495-503 (2004).

von Altrock, A., "Sudden Deaths in Fattening Herds on taking Blood Samples- Experiences from the Practice." Berl Munch Tierarztl Wschr, vol. 112, pp. 89-90. (1999).

Wang, et al., "Cloning and characterization of novel PDE4D isoforms PDE4D6 and PDE4D7," Cell. Signal. 15, 883-891 (2003).

Wang, J. et al. "Physical Training Alters the Pathogenesis of Pacing-Induced Heart Failure Through Endothelium-Mediated Mechanisms in Awake Dogs." Circulation, vol. 96, pp. 2683-2692. (1997).

Wehrens et al. "Ca2+/Calmodulin-Dependent Protein Kinase II Phosphorylation Regulates the Cardiac Ryanodine Receptor." Circ. Res., vol. 94, No. 6, pp. e61-70. (Apr. 2004).

Wehrens et al., "Enhancing Calstabin Binding to Ryanodine Receptors Improves Cardiac and Skeletal Muscle Function in Heart Failure." PNAS, vol. 102, No. 27, pp. 9607-9612. (2005).

Wehrens et al., "Molecular Determinants of Altered Contractility in Heart Failure." Ann Med., vol. 36, Suppl. 1, pp. 70-80. (2004).

Wehrens et al., "Novel Therapeutic Approaches for Heart Failure by Normalizing Calcium Cycling." Nature Reviews Drug Discovery., vol. 3, pp. 565-573. (2004).

Wehrens et al., "Protection from Cardiac Arrhythmia Through Ryanodine Receptor-Stabilizing Protein Calstabin2." Science, vol. 304, pp. 292-296. (Apr. 2004).

Wehrens et al., "Ryanodine Receptor-Targeted Anti-Arrhythmic Therapy." Ann N. Y Acad. Sci., vol. 1047, pp. 366-375. (2005).

Wehrens et al., "Sudden Unexplained Death Caused by Cardiac Ryanodine Receptor (RyR2) Mutations." Mayo Clin Proc., vol. 79, No. 11, pp. 1367-1371. (Nov. 2004).

Wehrens, et al., "Intracellular Calcium Release Channels and Cardiac Disease," Annu. Rev. Physiol. (2004).

Westphal, R.S. et al. "Regulation of NMDA Receptors by an Associated Phosphatase-Kinase Signaling Complex." Science, vol. 285, pp. 93-96. (1999).

Wilson, et al. "Exertional Fatigue Due to Skeletal Muscle Dysfunction in Patients with Heart Failure." Circulation, vol. 87, pp. 470-475. (1993).

Wilson, J.R. "Exercise Intolerance in Heart Failure. Importance of Skeletal Muscle." Circulation, vol. 91, pp. 559-561. (1995).

Xiang, Y. et al.: "Phosphodiesterase 4D is required for β2 adrenoceptor subtype-specific signaling in cardiac myocytes," PNAS, Jan. 18, 2005, vol. 102, No. 3, 909-914.

Xin, H.B. et al. "Oestrogen Protects FKBP12.6 Null Mice from Cardiac Hypertrophy." Nature, vol. 416, pp. 334-337. (2002).

Yamamoto-Hino, M. et al. "Cloning and Characterization of Human Type 2 and Type 3 Inositol 1,4,5-trisphosphate Receptors." Receptor Channels, vol. 2, pp. 9-22. (1994).

Yamawaza, et. al., "Subtype Specificity of the Ryanodine Receptor for $Ca^{2+}$ Signal Amplification in the Excitation-Contraction Coupling," The EMBO Journal, vol. 15, No. 22, pp. 6172-6177, 1996.

Yang, Jiacheng et al. "A-kinase Anchoring Protein 100 (AKAP100) is Localized in Multiple Subcellular Compartments in the Adult Rat Heart." The Journal of Cell Biology, vol. 142, No. 2, pp. 511-522 (Jul. 27, 1998.).

Yano, M. et al. "FKBP12.6-Mediated Stabilization of Calcium-Release Channel (Ryanodine Receptor) as a Novel Therapeutic Strategy against Heart Failure." Circulation, vol. 107, pp. 477-484. (2003).

Zaccolo, et al., "Discrete micro domains with high concentration of cAMP in stimulated rat neonatal cardiac myocytes," Science 295, 1711-5 (2002).

Zucchi et al., "The Sarcoplasmic Reticulum $Ca^{2+}$ Channel/ Ryanodine Receptor: Modulation by Endogenous Effectors, Drugs, and Disease States." Pharmacological Reviews, vol. 49, No. 1, pp. 1-51. (1997).

Bidasee et al., "Diabetes Increases Formation of Advanced Glycation End Products on Sarco (endo) plasmic Reticulum Ca2+-ATPase," Diabetes, vol. 53, pp. 463-473 (2004).

Bruton et al., "Ryanodine receptors of pancreatic β-cells mediate a distinct context-dependent signal for insulin secretion," the FASEB Journal, vol. 17, pp. 301-303 (2003).

Buijs et al., "β-Adrenergic activation reveals impaired cardia calcium handling at early stage of diabetes," Life Sciences, vol. 76, pp. 1083-1098 (2005).

Dyachok et al., "Ca2+-induced Ca2+ release by activation of inositol 1,4,5-trisphosphate receptors in primary pancreatic β-cells," Cell Calcium, vol. 36, pp. 1-9 (2004).

Dyachok et al., "Ca2+-induced Ca2+ Release via Inositol 1,4,5-trisphosphate Receptors Is Amplified by Protein Kinase and Triggers Exocytosis in Pancreatic β-Cells," The Journal of Biological Chemistry, vol. 279, No. 44, pp. 45455-45461 (2004).

Eisner et al., "The Ryanodine Receptor: Cause or Consequence of Diabetic Heart Failure?," J. Moll Cell Cardiol, vol. 32, pp. 1377-1378 (2000).

Holz et al., "cAMP-dependent Mobilization of Intracellular Ca2+ Stores by Activation of Ryanodine Receptors in Pancreatic β-Cells," The Journal of Biological Chemistry, vol. 274, pp. 14147-14156 (1999).

International Preliminary Report on Patentability from International Application PCT/US2005/045914, mailed Jun. 28, 2007.

International Search Report and Written Opinion from PCT/US2005/10056, Jun. 5, 2007.

Islam et al., "Effects of caffeine on cytoplasmic free Ca2+ concentration in pancreatic β-cells are mediated by interaction with ATP-sensitive K+ channels and L-type voltage-gated Ca2+ channels but not ryanodine receptor," Biochem. J., vol. 306, pp. 679-686 (1995).

Islam et al., "In situ activation of the type 2 ryanodine receptor in pancreatic beta cells requires cAMP-dependent phosphorylation," Proc. Natl. Acad. Sci. USA, vol. 95, pp. 6145-6150 (1998).

Islam S., "Perspectives in Diabetes. The Ryanodine Receptor Calcium Channel of β-Cells. Molecular Regulation and Physiological Significance," Diabetes, vol. 51, pp. 1299-1309 (2002).

Johnson et al., "Ryanodine receptors in human pancreatic β cells: localization and effects on insulin secretion1," the FASEB Journal, vol. 18, pp. 878-880 (2004).

Johnson et al., "RyR2 and Calpain-10 Delineate a Novel Apoptosis Pathway in Pancreatic Islets," The Journal of Biological Chemistry, vol. 279, pp. 24794-24802 (2004).

Kang et al., "A cAMP and Ca2+ coincidence detector in support of Ca2+-induced Ca2+ release in mouse pancreatic β cells," J. Physiol, vol. 566, pp. 173-188 (2005).

Kang et al., "cAMP-regulated guanine nucleotide exchange factor II (Epac2) mediates Ca2+-induced Ca2+ release in INS-1 pancreatic β-cells," Journal of Physiology, vol. 536.2, pp. 375-385 (2001).

Lehnart et al., "Phosphodiesterase 4D associates with the cardiac calcium release channel (Ryanodine Receptor) and protects from Hypertrophy and heart failure", Circulation, vol. 110, No. 17 Suppl. S, pp. 227-228 (Oct. 26, 2004).

Liu et al., "Crosstallk between the cAMP and Inositol Trisphosphate-Signalling Pathways in Pancreatis β-Cells," Archives of Biochemistry and Biophysics, vol. 334, pp. 295-302 (1996).

Mitchell et al., "Ryanodine Receptor Type I and Nicotinic Acid Adenine Dinucleotide Phosphate Receptors Mediate Ca2+ Release from Insulin-containing Vesicles in Living Pancreatic β-Cells (MIN6)," The Journal of Biological Chemistry, vol. 278, pp. 11057-11064 (2003).

Pereira et al., "Mechanisms of [Ca2+]i Transient Decrease in Cardiomyopathy of db/db Type 2 Diabetic Mice," Diabetes, vol. 55, pp. 608-615 (2006).

Shao et al., "Dyssynchronous (non-uniform) Ca2+ release in myocytes from streptozotocin-induced diabetic rats," Journal of Molecular and Cellular Cardiology, vol. 42, pp. 234-246 (2007).

Takasawa et al., "Cyclic ADP-ribose and Inositol 1,4,5-Trisphosphate as Alternate Second Messengers for Intracellular Ca2+ Mobilization in Normal and Diabetic β-Cells," The Journal of Biological Chemistry, vol. 273, pp. 2497-2500 (1998).

Varadi et al., "Dynamic Imaging of Endoplasmic Reticulm Ca2+ Concentration in Insulin-Secreting MIN6 Cells Using Recombinant Target Cameleons. Role of Sarco (endo) plasmic Reticulum Ca2+-ATPase (SERCA)-2 and Ryanodine Receptors," Diabetes, vol. 51, Suppl. 1, pp. S190-S201 (2002).

Woolcott et al., "Arachidonic acid is a physiological activator of the ryanodine receptor in pancreatic β-cells," Cell Calcium, vol. 39, pp. 529-537 (2006).

Yaras et al., "Effects of Diabetes on Ryanodine Receptor Ca Release Channel (RyR2) and Ca2+ Homeostasis in Rat Heart," Diabetes, vol. 54, pp. 3082-3088 (2005).

Yaras et al., "Restoration of Diabetes-Induced abnormal local Ca2+ release in cardiomyocytes by angiotensin II receptor blockade," Am J. Physiol Heart Circ Physiol, vol. 292, pp. H912-H920 (2007).

Zhang et al., "Growth Hormone Promotes Ca+2-induces Ca2+ Release in Insulin-Secreting Cells by Ryanodine Receptor Tyrosine Phosphorylation," Molecular Endocrinology, vol. 18, pp. 1658-1669 (2004).

Alvarez et al., Late post-myocardial infarction induces a tetrodotoxin-resistant Na+ current in rat cardiomyocytes. J. Mol. Cell Cardiol., 32: 1169-1179, 2000.

Antiarrhythmic effects of JTV-519, a novel cardioprotective drug, on atrial fibrillation / flutter in a canine sterile pericarditis model. J. Cardiovasc. Electrophysiol., 14: 880-884, 2003.

Antos et al., Dilated cardiomyopathy and sudden death resulting from constitutive activation of protein kinase A. Circ. Res., 89: 997-1004, 2001.

Barbone et al., Comparison of right and left ventricular responses to left ventricular assist device support in patients with severe heart failure: a primary role of mechanical unloading underlying reverse remodeling. Circulation, 104: 670-675, 2001.

Bennett and Pentecost, The pattern of onset and spontaneous cessation of atrial fibrillation in man. Circulation, 41: 981-988, 1970.

Bennett et al., Identification and characterization of the murine FK506 binding protein (FKBP) 12.6 gene. Mamm. Genome, 9: 1069-1071, 1998.

Beuckelmann et al., Intracellular calcium handling in isolated ventricular myocytes from patients with terminal heart failure. Circ., 85: 1046-1055, 1992.

Brillantes et al., Stabilization of calcium release channel (ryanodine receptor) function by FK506-binding protein. Cell, 77: 513-523, 1994.

Bristow et al., Decreased catecholamine sensitivity and beta-adrenergic—receptor density in failing human hearts. N. Engl. J. Med., 307: 205-211, 1982.

Burashnikov and Antzelevitch, Reinduction of atrial fibrillation immediately after termination of the arrhythmia is mediated by late phase 3 early afterdepolarization-induced triggered activity. Circulation, 107: 2355-2360, 2003.

Cameron et al., FKBP12 binds the inositol 1,4,5-trisphosphate receptor at leucine-proline (1400-1401) and anchors calcineurin to this FK506-like domain. J. Biol. Chem., 272: 27582-27588, 1997.

Chen et al., Mechanism of TGFbeta receptor inhibition by FKBP12. EMBO J., 16: 3866-3876, 1997.

Chidsey et al., Augmentation of plasma norepinephrine response to exercise in patients with congestive heart failure. N. Engl. J. Med., 267: 650, 1962.

Chugh et al., Epidemiology and natural history of atrial fibrillation: clinical implications. J. Am. Coll. Cardiol., 37: 371-378, 2001.

Cranefield, P.F., Action potentials, afterpotentials, and arrhythmias. Circ. Res., 41: 415-423, 1977.

Daoud et al., Effect of verapamil and procainamide on atrial fibrillation-induced electrical remodeling in humans. Circulation, 96: 1542-1550, 1997.

Dun et al., Chronic atrial fibrillation does not further decrease outward currents. It increases them. Am. J. Physiol. Heart Circ. Physiol., 285: H1378-1384, 2003.

Eichhorn and Bristow, Medical therapy can improve the biological properties of the chronically failing heart. A new era in the treatment of heart failure. Circulation, 94: 2285-2296, 1996.

Elvan et al., Pacing-induced chronic atrial fibrillation impairs sinus node function in dogs: electrophysiological remodeling. Circulation, 94: 2953-2960, 1996.

Fabiato, A., Calcium-induced release of calcium from the cardiac sarcoplasmic reticulum. Am. J. Physiol., 245: C1-C14, 1983.

Falk, R.H., Atrial fibrillation. N. Engl. J. Med., 344: 1067-1078, 2001.

Fozzard, H.A., Afterdepolarizations and triggered activity. Basic Res. Cardiol., 87: 105-113, 1992.

Gaspo et al., Functional mechanisms underlying tachycardia-induced sustained atrial fibrillation in a chronic dog model. Circulation, 96: 4027-4035, 1997.

Gillo et al., Calcium entry during induced differentiation in murine erythroleukemia cells. Blood, 81: 783-792, 1993.

Goette et al., Electrical remodeling in atrial fibrillation: time course and mechanisms. Circulation, 94: 2968-2974, 1996.

Gomez et al., Defective excitation-contraction coupling in experimental cardiac hypertrophy and heart failure. Science, 276: 800-806, 1997.

Gwathmey et al., Abnormal intracellular calcium handling in myocardium from patients with end-stage heart failure. Circ. Res., 61: 70-76, 1987.

Hain et al., Phosphorylation modulates the function of the calcium release channel of sarcoplasmic reticulum from cardiac muscle. J. Biol. Chem., 270: 2074-2081, 1995.

Hara et al., Steady-state and nonsteady-state action potentials in fibrillating canine atrium: abnormal rate adaptation and its possible mechanisms. Cardiovasc. Res., 42: 455-469, 1999.

Jayaraman et al., FK506 binding protein associated with the calcium release channel (ryanodine receptor). J. Biol. Chem., 267: 9474-9477, 1992.

Jayaraman et al., Regulation of the inositol 1,4,5-trisphosphate receptor by tyrosine phosphorylation. Science, 272: 1492-1494, 1996.

Kaftan et al., Effects of rapamycin on ryanodine receptor / Ca (2+)-release channels from cardiac muscle. Circ. Res., 78: 990-997, 1996.

Kneller et al., Remodeling of Ca2+—handling by atrial tachycardia: evidence for a role in loss of rate-adaptation. Cardiovasc. Res., 54: 416-426, 2002.

Kohno et al., A new cardioprotective agent, JTV519, improves defective channel gating of ryanodine receptor in heart failure. Am. J. Physiol. Heart Circ. Physiol., 14:14, 2002.

Kumagai et al., Antiarrhythmic effects of JTV-519, a novel cardioprotective drug, on atrial fibrillation / flutter in a canine sterile pericarditis model. J. Cardiovasc. Electrophysiol., 14: 880-884, 2003.

Laitinen et al., Mutations of the cardiac ryanodine receptor (RyR2) gene in familial polymorphic ventricular tachycardia. Circulation, 103: 485-490, 2001.

Leenhardt et al., Catecholaminergic polymorphic ventricular. tachycardia in children: a 7-year follow-up of 21 patients. Circulation, 91: 1512-1519, 1995.

Leistad et al., Atrial contractile dysfunction after short-term atrial fibrillation is reduced by verapamil but increased by BAY K8644. Circulation, 93: 1747-1754, 1996.

Levy et al., Long-term trends in the incidence of and survival with heart failure. N. Engl. J. Med., 347: 1397-1402, 2002.

Marban et al., Mechanisms of arrhythmogenic delayed and early afterdepolarizations in ferret ventricular muscle. J. Clin. Invest., 78: 1185-1192, 1986.

Marks, A.R., Cellular functions of immunophilins. Physiol. Rev., 76: 631-649, 1996.

Marks, A.R., Cardiac intracellular calcium release channels: role in heart failure. Circ. Res., 87: 8-11, 2000.

Marks et al., Progression of heart failure: is protein kinase a hyperphosphorylation of the ryanodine receptor a contributing factor? Circulation, 105: 272-275, 2002.

Marx et al., Coupled gating between individual skeletal muscle Ca2+ release channels (ryanodine receptors). Science, 281: 818-821, 1998.

Marx et al., PKA phosphorylation dissociates FKBP12.6 from the calcium release channel (ryanodine receptor): defective regulation in failing hearts. Cell, 101: 365-376, 2000.

Mohler et al., Ankyrin-B mutation causes type 4 long-QT cardiac arrhythmia and sudden cardiac death. Nature, 421: 634-639, 2003.

Morillo et al., Chronic rapid atrial pacing: structural, functional, and electrophysiological characteristics of a new model of sustained atrial fibrillation. Circulation, 91: 1588-1595, 1995.

Nabauer et al., Regulation of calcium release is gated by calcium current, not gating charge, in cardiac myocytes. Science, 244: 800-803, 1989.

Ono et al., Altered interaction of FKBP12.6 with ryanodine receptor as a cause of abnormal Ca2+ release in heart failure. Cardiovasc. Res., 48: 323-331, 2000.

Priori et al., Clinical and molecular characterization of patients with catecholaminergic polymorphic ventricular tachycardia. Circulation, 106: 69-74, 2002.

Priori et al., Mutations in the cardiac ryanodine receptor gene (hRyR2) underlie catecholaminergic polymorphic ventricular tachycardia. Circulation, 103: 196-200, 2001.

Ramirez et al., Mathematical analysis of canine atrial action potentials: rate, regional factors, and electrical remodeling. Am. J. Physiol. Heart Circ. Physiol., 279: H1767-1785, 2000.

Reiken et al., Beta-adrenergic receptor blockers restore cardiac calcium release channel (ryanodine receptor) structure and function in heart failure. Circulation, 104: 2843-2848, 2001.

Reiken et al., Beta-blockers restore calcium release channel function and improve cardiac muscle performance in human heart failure. Circulation, 107: 2459-2466, 2003.

Reiken et al., PKA phosphorylation dissociates FKBP12 from the calcium release channel (ryanodine receptor) in skeletal muscle: defective regulation in heart failure. J. Cell Biol., 160: 919-928, 2003.

Rensma et al., Length of excitation wave and susceptibility to reentrant atrial arrhythmias in normal conscious dogs. Circ. Res., 62: 395-410, 1988.

Semsarian et al., The L-type calcium channel inhibitor diltiazem prevents cardiomyopathy in a mouse model. J. Clin. Invest., 109: 1013-1020, 2002.

Song and Belardinelli, ATP promotes development of afterdepolarizations and triggered activity in cardiac myocytes. Am. J. Physiol., 267: H2005-2011, 1994.

Sun et al., Cellular mechanisms of atrial contractile dysfunction caused by sustained atrial tachycardia. Circulation, 98: 719-727, 1998.

Swan et al., Arrhythmic disorder mapped to chromosome 1q42-q43 causes malignant polymorphic ventricular tachycardia in structurally normal hearts. J. Am. Coll. Cardiol., 34: 2035-2042, 1999.

Tieleman et al., Verapamil reduces tachycardia-induced electrical remodeling of the atrial. Circulation, 95: 1945-1953, 1997.

Timmermans et al., Immediate reinitiation of atrial fibrillation following internal atrial defibrillation. J. Cardiovasc. Electrophysiol., 9: 122-128, 1998.

Valdivia et al., Rapid adaptation of cardiac ryanodine receptors: modulation by Mg2+ and phosphorylation. Science, 267: 1997-2000, 1995.

Wang et al., Regional and functional factors determining induction and maintenance of atrial fibrillation in dogs. Am. J. Physiol., 271: H148-158, 1996.

Wehrens et al., FKBP12.6 deficiency and defective calcium release channel (ryanodine receptor) function linked to exercise-induced sudden cardiac death. Cell, 113: 829-840, 2003.

Wellens et al., Atrioverter: an implantable device for the treatment of atrial fibrillation. Circulation, 98: 1651-1656, 1998.

Wijffel et al., Atrial fibrillation begets atrial fibrillation: a study in awake chronically instrumented goats. Circulation, 92:1954-1968, 1995.

Wit and Rosen, Pathophysiologic mechanisms of cardiac arrhythmias. Am. Heart J., 106: 798-811, 1983.

Yamamoto et al., Abnormal Ca2+ release from cardiac sarcoplasmic reticulum in tachycardia-induced heart failure. Cardiovasc. Res., 44: 146-155, 1999.

Yano et al., Altered stoichiometry of FKBP12.6 versus ryanodine receptor as a cause of abnormal Ca2+ leak through ryanodine receptor in heart failure. Circulation, 102: 2131-2136, 2000.

Yano et al., FKBP12.6-mediated stabilization of calcium-release channel (ryanodine receptor) as a novel therapeutic strategy against heart failure. Circulation, 107: 477-484, 2003.

Yu et al., Tachycardia-induced change of atrial refractory period in humans: rate dependency and effects of antiarrhythmic drugs. Circulation, 97: 2331-2337, 1998.

Yue et al., Ionic remodeling underlying action potential changes in a canine model of atrial fibrillation. Circ. Res., 81: 512-525, 1997.
Bidasee et al., "Chronic Diabetes Increases Advanced Glycation End Products on Cardiac Ryanodine Receptors/Calcium-Release Channels," Diabetes, vol. 52, pp. 1825-1836 (Jul. 2003).
CIBIS-II Investigators and Committees, The Cardiac Insufficiency Bisoprolol Study II (CIBIS-II): A Randomized Trial. The Lancet, vol. 353, pp. 9-13, (1999).
Exhibit A: Chemical Structures—Prior search.
The Cardiac Arrhythmia Suppression Trial (CAST) Investigators, Special Report "Preliminary Report: Effect of Encainide and Flecainide on mortality in a randomized trial of arrhythmia suppression after myocardial infraction," The New England Jour. of Med., vol. 321, No. 6, pp. 406-412. (1989).
Supplementary European Search Report for European Patent Application No. 04756121.2, mailed Dec. 21, 2007.
Non Final Office Action mailed Aug. 7, 2001 for U.S. Appl. No. 09/568,474, filed Mar. 10, 2000.
Non Final Office Action mailed Jan. 14, 2002 for U.S. Appl. No. 09/568,474, filed May 10, 2000.
Non Final Office Action mailed on May 4, 2004 for U.S. Appl. No. 10/288,606, filed Nov. 5, 2002.
Final Office Action mailed on Nov. 22, 2004 for U.S. Appl. No. 10/288,606, filed Nov. 5, 2002.
Non Final Office Action Mailed on Jul. 11, 2005 for U.S. Appl. No. 10/288,606, filed Nov. 5, 2002.
Final Office Action mailed on Jan. 5, 2006 for U.S. Appl. No. 10/288,606, filed Nov. 5, 2002.
Non Final Office Action mailed on Jan. 26, 2007 for U.S. Appl. No. 10/288,606, filed Nov. 5, 2002.
Final Office Action mailed on Oct. 5, 2007 for U.S. Appl. No. 10/288,606, filed Nov. 5, 2002.
Non Final Office Action mailed on Mar. 25, 2008 for U.S. Appl. No. 10/288,606, filed Nov. 5, 2002.
Non Final Office Action mailed on Feb. 27, 2007 for U.S. Appl. No. 10/680,988, filed Oct. 7, 2003.
Final Office Action mailed Nov. 29, 2007 for U.S. Appl. No. 10/680,988, filed Oct. 7, 2003.
Non Final Office Action mailed on Mar. 19, 2008 for U.S. Appl. No. 10/680,988, filed Oct. 7, 2003.
Non Final Office Action mailed on Apr. 27, 2005 for U.S. Appl. No. 10/608,723, filed Jun. 26, 2003.
Final Office Action mailed on Dec. 29, 2005 for U.S. Appl. No. 10/608,723, filed Jun. 26, 2003.
Non Final Office Action mailed on Aug. 23, 2006 for U.S. Appl. No. 10/608,723, filed Jun. 26, 2003.
Final Office Action mailed on Feb. 16, 2007 for U.S. Appl. No. 10/608,723, filed Jun. 26, 2003.
Non Final Office Action mailed on Oct. 30, 2007 for U.S. Appl. No. 10/608,723, filed Jun. 26, 2003.
Final office Action mailed on Mar. 20, 2008 for U.S. Appl. No. 10/608,723, filed Jun. 26, 2003.
Non Final Office Action mailed on May 3, 2005 for U.S. Appl. No. 10/794,218, filed Mar. 5, 2004.
Non Final Office Action mailed on Jan. 9, 2006 for U.S. Appl. No. 10/794,218, filed Mar. 5, 2004.
Final Office Action mailed on Aug. 23, 2006 for U.S. Appl. No. 10/794,218, filed Mar. 5, 2004.
Non Final Office Action mailed on Aug. 29, 2006 for U.S. Appl. No. 11/088,123, filed Mar. 23, 2005.
Final Office Action mailed on Mar. 27, 2007 for U.S. Appl. No. 11/088,123, filed Mar. 23, 2005.
Gailly, "New Aspects of Calcium signaling in skeletal muscle cells: implications in Duchenne muscular Dystrophy," Biochimica et Biophysica Acta, vol. 1600, pp. 38-44 (2002).
International Preliminary Report on Patentability from International Application PCT/US2005/010055, mailed Oct. 4, 2007.
International Preliminary Report on Patentability from International Application PCT/US2005/010056, mailed Oct. 4, 2007.
International Search Report and Written Opinion from International Patent Appilcation No. PCT/US06/32405, Dec. 7, 2007.

LaFerla, "Calcium Dyshomeostasis and Intracellular signalling in Alzheimer's disease," Nature Reviews, vol. 3, pp. 862-872 (Nov. 2002).
Mackenzie et all, "The Role of inositol 1,4,5-trisphosphate receptors in Ca2+ signalling and the generation of arrhythmias in rat atrila myocytes," J. Physiol., vol. 541, pp. 395-409 (2002).
Taur et al., "The Cardiac Ryanodine Receptor (RyR2) and its Role in Heart Disease," Cardiology in Review, vol. 13, No. 3, pp. 142-146 (2005).
Most et al., Sealing the leak, healing the heart, Nature Medicine, vol. 9, pp. 993-994 (Aug. 2003).
International Search Report and Written Opinion for International Patent Application No. PCT/US04/06971, mailed Jun. 25, 2008.
International Search Report and Written Opinion for International Patent Application No. PCT/US07/09715, mailed Aug. 21, 2008.
International Search Report and Written Opinion for International Patent Application No. PCT/US07/18138, mailed Aug. 26, 2008.
International Search Report and Written Opinion for International Patent Application No. PCT/US07/18147, mailed Sep. 8, 2008.
International Search Report and Written Opinion mailed Oct. 28, 2008 for International Patent Application No. PCT/US07/12936 filed Jun. 1, 2007.
Non Final Office Action mailed Oct. 20, 2008 for U.S. Appl. No. 11/212,309, filed Aug. 25, 2005.
Non Final Office action mailed Oct. 20, 2008 for U.S. Appl. No. 11/212,413, filed Aug. 25, 2005.
Giordano et al., "Rapamycin antagonizes NF-KappaB nuclear translocation activated by TNF-alpha in primary vascular smooth muscle cells and enhances apoptosis," Am J. Physiol Heart circu Physiol, vol. 290, pp. 2459-2465, (2006).
International Search Report an Written opinion mailed Aug. 14, 2008, for International Application No. PCT/US07/09289 filed Apr. 13, 2007.
Zahradka et al., "Activation of MMP-2 in response to vascular injury is mediated by phosphatidylinositol 3-kinase-Dependent expression of MT1-MMP," Am J. Physiol Heart Circ. Physiol, vol. 287, pp. H2861-H2870 (2004).
International Search Report and Written Opinion mailed Jan. 10, 2008 for International Patent Application No. PCT/US07/12969 filed Jun. 1, 2007.
Non Final Office Action mailed Sep. 17, 2008 for U.S. Appl. No. 11/305,528, filed Dec. 16, 2005.
Altamura et al.,"Investigation on the flexibility of chiral tricyclic derivatives," New J. Chem., 32, 1617-1627 (2008).
Garofalo et a., "Polycondensed Heterocycles. X. Method For The Preparation of Pyrrolo[2,1-c][1,4]benzothiazepines by Intramolecular Mitsunobu Cyclisation," Tetrahedron 55:1479-1490 (1999).
Hirai et al., Reactivity of some benzodiazepine derivatives, Sankyo Kenkyusho Nenpo, 44: 141-50 (1992).
Johansson B.W., "Adams-Stokes Syndrome. A Review and follow-up Study of Forty-two cases," The American Journal of Cardiology, pp. 76-93 (Jul. 1961).
Nousiainan et al., "Cardiac arrhythmias in the differential diagnosis of epilepsy," J. Neurol, vol. 236, pp. 93-96 (1989).
Schott et al., "Cardiac Arrhythmias that masquerade as epilepsy," British Medical Journal, vol. 1, pp. 1454-1457 (1977).
Supplementary European Search Report mailed Dec. 12, 2008 for European Patent Application No. 04794052.3 filed Oct. 4, 2004.
Supplementary European Search Report mailed on Mar. 27, 2009 for European Patent Application No. 05732932.8 filed Mar. 22, 2005.
Supplementary European Search Report mailed May 14, 2009 for European Patent Application No. 06801887.8, filed Aug. 17, 2006.
Czoliner et al., "Synthesis of 1,4-benzothiazepines and investigation of their reactions," Magyar Kemiai Folyoirat, Kiralyi Magy. Termtud. Tars. Chem. Szakoszt, Budapest, Hu, vol. 94, pp. 332-335 (1988).
Duddeck et al., "Oxazepines and thiazepines, XVI. Proton and Carbon-13 NMR studies of the structure of Benzothiazepinone derivative," Liebigs Annalen der Chemie, pp. 869-876 (1985), English Abst only.
Extended European Search Report for European Patent No. 09166965.5.

Levai et al., "Oxazepines and thiazepines. VI. A convenient synthesis of benzothiazepines sulfoxides," Acta Chimica, Academia Scientiarum Hungarica, Budapest, HU, vol. 102, pp. 141-142 (1979).

Shridhar et al, "Antiinflammatory agents. Part VII. Synthesis of some new methyl 2,3-dihydro-1,4- and-1,5-benzothiazepinone-2-acetates," Indian Journal of Chemistry, Section B: Organic and Medicinal Chemistry Scientific Publishers, Jodhpur, In, vol. 22B, pp. 300-302 (1983).

Still et al., "Behavior of thiochromanone and isothiochromanone sulfoxides in the Schmidt reaction. Isolation of a novel azide product from thiochromone sulfone," Canadian Journal of Chemistry, pp. 276-282 (1975).

Wuensch et al., "B enzokondensierte 7-ring-Heterocyclen, I.2.3.4.5-Tetrahydro-1.4-benzothiazepin-one-(5)=Benzo condensed heterocycles with 7-membered rings. I. 2,3,4,5-Tetrahydro-1, 4-benzothiazepin-5-ones," Chemische Berichte, verlag Chemie GMBH. Weinheim, DE, vol. 102, pp. 1618-1625 (May 1969) (English Abstract).

Wuensch et al., "Benzokondensierte 7-ring-Heterocyclen, IV. Schmidt-Reaktion and 1-thio-chromanonen-(4) und 1-Thio-chromanon-(4)-1.1-dioxiden=benzo-fused seven-membered heterocyclic compounds. IV. Schmidt reaction on 1-thio-4-chromanone and 1-thio-4-chromanone 1,1-dioxides," Chemische Berichte, verlag Chemie GMBH. Weinheim, DE, vol. 103, pp. 2302-2307 (Jul. 1970) (English Abstract).

* cited by examiner

A Control
Po 0.008, To 2.0 ms, Tc 1107.2 ms

Atrial fibrillation
Po 0.412, To 3.8 ms, Tc 20.6 ms

B

ANTI-ARRHYTHMIC AND HEART FAILURE DRUGS THAT TARGET THE LEAK IN THE RYANODINE RECEPTOR (RYR2) AND USES THEREOF

RELATED APPLICATIONS

This application is a continuation-in-part of U.S. patent application Ser. No. 10/763,498, filed on Jan. 22, 2004, now abandoned, the contents of which is hereby incorporated by reference herein.

STATEMENT OF GOVERNMENT INTEREST

This invention was made with government support under NIH Grant No. PO1 HL 67849-01. As such, the United States government has certain rights in this invention.

BACKGROUND OF THE INVENTION

Despite advances in treatment, congestive heart failure remains an important cause of mortality in Western countries. Heart failure affects 5 million individuals in the United States alone, and is characterized by a 5-year mortality rate of ~50% (Levy et al., Long-term trends in the incidence of and survival with heart failure. *N. Engl. J. Med.*, 347:1397-402, 2002).

An important hallmark of heart failure is reduced myocardial contractility (Gwathmey et al., Abnormal intracellular calcium handling in myocardium from patients with end-stage heart failure. *Circ. Res.*, 61:70-76, 1987). In healthy heart muscle, and in other striated muscle, calcium-release channels on the sarcoplasmic reticulum (SR), including ryanodine receptors (RyRs), facilitate coupling of an action potential to a muscle cell's contraction (i.e., excitation-contraction (EC) coupling). Contraction is initiated when calcium ($Ca^{2+}$) is released from the SR into the surrounding cytoplasm. In heart failure, contractile abnormalities result, in part, from alterations in the signaling cascade that allows the cardiac action potential (AP) to trigger contraction. In particular, in failing hearts, the amplitude of the whole-cell $Ca^{2+}$ transient is decreased (Beuckelmann et al., Intracellular calcium handling in isolated ventricular myocytes from patients with terminal heart failure. *Circ.*, 85:1046-55, 1992; Gomez et al., Defective excitation-contraction coupling in experimental cardiac hypertrophy and heart failure. *Science*, 276: 800-06, 1997), and the duration is prolonged (Beuckelmann et al., Intracellular calcium handling in isolated ventricular myocytes from patients with terminal heart failure. *Circ.*, 85:1046-55, 1992).

Cardiac arrhythmia, a common feature of heart failure, is known to be associated with SR $Ca^{2+}$ leaks in structurally-normal hearts. In these cases, the most common mechanism for induction and maintenance of ventricular tachycardia is abnormal automaticity. One form of abnormal automaticity, known as triggered arrhythmia, is associated with aberrant release of SR $Ca^{2+}$, which initiates delayed after-depolarizations, or DADs (Fozzard, H. A., After depolarizations and triggered activity. *Basic Res. Cardiol.*, 87:105-13, 1992; Wit and Rosen, Pathophysiologic mechanisms of cardiac arrhythmias. *Am. Heart J.*, 106:798-811, 1983). DADs are abnormal depolarizations in cardiomyocytes that occur after repolarization of a cardiac action potential. The molecular basis for the abnormal SR $Ca^{2+}$ release that results in DADs has not been fully elucidated. However, DADs are known to be blocked by ryanodine, providing evidence that RyR2 may play a key role in the pathogenesis of this aberrant $Ca^{2+}$ release (Marban et al., Mechanisms of arrhythmogenic delayed and early afterdepolarizations in ferret ventricular muscle. *J. Clin. Invest.*, 78:1185-92, 1986; Song and Belardinelli, ATP promotes development of afterdepolarizations and triggered activity in cardiac myocytes. *Am. J. Physiol.*, 267:H2005-11, 1994).

The most common cardiac arrhythmia in humans is atrial fibrillation (AF). It represents a major cause of morbidity and mortality (Chugh et al., Epidemiology and natural history of atrial fibrillation: clinical implications. *J. Am. Coll. Cardiol.*, 37:371-78, 2001; Falk, R. H., Atrial fibrillation. *N. Engl. J. Med.*, 344:1067-78, 2001). Despite its clinical importance, however, treatment options for AF have been limited—due, in part, to the fact that its underlying molecular mechanisms are poorly understood.

Approximately 50% of all patients with heart disease die from fatal cardiac arrhythmias. Such fatal cardiac arrhythmias are often ventricular in nature. In some cases, a ventricular arrhythmia in the heart may be rapidly fatal—a phenomenon referred to as "sudden cardiac death" (SCD). Fatal ventricular arrhythmias (and SCD) may also occur in young, otherwise-healthy individuals who are not known to have structural heart disease. In fact, ventricular arrhythmia is the most common cause of sudden death in otherwise-healthy individuals.

Catecholaminergic polymorphic ventricular tachycardia (CPVT) is an inherited disorder in individuals with structurally-normal hearts. It is characterized by stress-induced ventricular tachycardia—a lethal arrhythmia that may cause SCD. In subjects with CPVT, physical exertion and/or stress induce bidirectional and/or polymorphic ventricular tachycardias that lead to SCD in the absence of detectable structural heart disease (Laitinen et al., Mutations of the cardiac ryanodine receptor (RyR2) gene in familial polymorphic ventricular tachycardia. *Circulation*, 103:485-90, 2001; Leenhardt et al., Catecholaminergic polymorphic ventricular tachycardia in children: a 7-year follow-up of 21 patients. *Circulation*, 91:1512-19, 1995; Priori et al., Clinical and molecular characterization of patients with catecholaminergic polymorphic ventricular tachycardia. *Circulation*, 106: 69-74, 2002; Priori et al., Mutations in the cardiac ryanodine receptor gene (hRyR2) underlie catecholaminergic polymorphic ventricular tachycardia. *Circulation*, 103:196-200, 2001; Swan et al., Arrhythmic disorder mapped to chromosome 1q42-q43 causes malignant polymorphic ventricular tachycardia in structurally normal hearts. *J. Am. Coll. Cardiol.*, 34:2035-42, 1999).

CPVT is predominantly inherited in an autosomal-dominant fashion. Individuals with CPVT have ventricular arrhythmias when subjected to exercise, but do not develop arrhythmias at rest. Linkage studies and direct sequencing have identified mutations in the human RyR2 gene, on chromosome 1q42-q43, in individuals with CPVT (Laitinen et al., Mutations of the cardiac ryanodine receptor (RyR2) gene in familial polymorphic ventricular tachycardia. *Circulation*, 103:485-90, 2001; Priori et al., Mutations in the cardiac ryanodine receptor gene (hRyR2) underlie catecholaminergic polymorphic ventricular tachycardia. *Circulation*, 103:196-200, 2001; Swan et al., Arrhythmic disorder mapped to chromosome 1q42-q43 causes malignant polymorphic ventricular tachycardia in structurally normal hearts. *J. Am. Coll. Cardiol.*, 34:2035-42, 1999).

There are three types of ryanodine receptors, all of which are highly-related $Ca^{2+}$ channels. RyR1 is found in skeletal muscle, RyR2 is found in the heart, and RyR3 is located in the brain. The type 2 ryanodine receptor (RyR2) is the major $Ca^{2+}$-release channel required for EC coupling and muscle contraction in cardiac striated muscle.

RyR2 channels are packed into dense arrays in specialized regions of the SR that release intracellular stores of $Ca^{2+}$, and thereby trigger muscle contraction (Marx et al., Coupled gating between individual skeletal muscle $Ca^{2+}$ release channels (ryanodine receptors). *Science*, 281:818-21, 1998). During EC coupling, depolarization of the cardiac-muscle cell membrane, in phase zero of the AP, activates voltage-gated $Ca^{2+}$ channels. In turn, $Ca^{2+}$ influx through these channels initiates $Ca^{2+}$ release from the SR via RyR2, in a process known as $Ca^{2+}$-induced $Ca^{2+}$ release (Fabiato, A., Calcium-induced release of calcium from the cardiac sarcoplasmic reticulum. *Am. J. Physiol.*, 245:C1-C14, 1983; Nabauer et al., Regulation of calcium release is gated by calcium current, not gating charge, in cardiac myocytes. *Science*, 244:800-03, 1989). The RyR2-mediated, $Ca^{2+}$-induced $Ca^{2+}$ release then activates the contractile proteins which are responsible for cardiac muscle contraction.

RyR2 is a protein complex comprising four 565,000-dalton RyR2 polypeptides in association with four 12,000-dalton FK506 binding proteins (FKBPs), specifically FKBP12.6 (calstabin). FKBPs are cis-trans peptidyl-prolyl isomerases that are widely expressed, and serve a variety of cellular functions (Marks, A. R., Cellular functions of immunophilins. *Physiol. Rev.*, 76:631-49, 1996). FKBP12 proteins are tightly bound to, and regulate the function of, the skeletal ryanodine receptor, RyR1 (Brillantes et al., Stabilization of calcium release channel (ryanodine receptor) function by FK506-binding protein. *Cell*, 77:513-23, 1994; Jayaraman et al., FK506 binding protein associated with the calcium release channel (ryanodine receptor). *J. Biol. Chem.*, 267: 9474-77, 1992); the cardiac ryanodine receptor, RyR2 (Kaftan et al., Effects of rapamycin on ryanodine receptor/Ca(2+)-release channels from cardiac muscle. *Circ. Res.*, 78:990-97, 1996); a related intracellular $Ca^{2+}$-release channel, known as the type 1 inositol 1,4,5-triphosphate receptor (IP3R1) (Cameron et al., FKBP12 binds the inositol 1,4,5-trisphosphate receptor at leucine-proline (1400-1401) and anchors calcineurin to this FK506-like domain. *J. Biol. Chem.*, 272: 27582-88, 1997); and the type I transforming growth factor β (TGFβ) receptor (TβRI) (Chen et al., Mechanism of TGFbeta receptor inhibition by FKBP12. *EMBO J.*, 16:3866-76, 1997). FKBP12.6 binds to the RyR2 channel (one molecule per RyR2 subunit), stabilizes RyR2-channel function (Brillantes et al., Stabilization of calcium release channel (ryanodine receptor) function by FK506-binding protein. *Cell*, 77:513-23, 1994), and facilitates coupled gating between neighboring RyR2 channels (Marx et al., Coupled gating between individual skeletal muscle $Ca^{2+}$ release channels (ryanodine receptors). *Science*, 281:818-21, 1998), thereby preventing aberrant activation of the channel during the resting phase of the cardiac cycle.

It is clear that leaks in RyR2 channels are associated with a number of pathological states—in both diseased hearts and structurally-normal hearts. Accordingly, methods to repair the leaks in RyR2 could treat or prevent heart failure, cardiac arrhythmias, and sudden cardiac death in millions of patients.

The 1,4-benzothiazepine derivative, JTV-519, or 4-[3-(4-benzylpiperidin-1-yl)propionyl]-7-methoxy-2,3,4,5-tetrahydro-1,4-benzothiazepine monohydrochloride (also known as k201 or ICP-Calstan 100), is a new modulator of calcium-ion channels. In addition to regulating $Ca^{2+}$ levels in myocardial cells, JTV-519 also modulates the $Na^+$ current and the inward-rectifier $K^+$ current in guinea pig ventricular cells, and inhibits the delayed-rectifier $K^+$ current in guinea pig atrial cells. Studies have shown that JTV-519 has a strong cardioprotective effect against catecholamine-induced myocardial injury, myocardial-injury-induced myofibrillar overcontraction, and ischemia/reperfusion injury. In experimental myofibrillar overcontraction models, JTV-519 demonstrated greater cardioprotective effects than propranolol, verapamil, and diltiazem. Experimental data have also suggested that JTV-519 effectively prevents ventricular ischemia/reperfusion by reducing the level of intracellular $Ca^{2+}$ overload in animal models.

SUMMARY OF THE INVENTION

The present invention is based upon the surprising discovery that RyR2 is a target for treating and preventing heart failure and cardiac arrhythmias, including atrial fibrillations, ventricular arrhythmias, and exercise-induced cardiac arrhythmias. As described herein, the inventors made mutant RyR2 channels with 7 different CPVT mutations, and studied their functions. All 7 mutants had functional defects that resulted in channels that became leaky (a calcium leak) when stimulated during exercise. The inventors' study is the first to identify a mechanism by which the SR calcium leak causes DADs. Remarkably, the defect in the mutant CPVT channels made the channels look like the leaky channels in the hearts of patients with end-stage heart failure—a disorder characterized by a high incidence of fatal cardiac arrhythmias. Therefore, the inventors have shown that the mechanism for the VT in CPVT is the same as the mechanism for VT in heart failure.

The inventors also disclose herein that JTV-519 (k201 or ICP-Calstan 100), and other novel 1,4-benzothiazepine derivatives, repair the leak in RyR2 channels. As the inventors have shown, JTV-519 and related derivatives enhance binding of FKBP12.6 to PKA-phosphorylated RyR2, and to mutant RyR2s that otherwise have reduced affinity for, or do not bind to, FKBP12.6. This action fixes the leak in RyR2 which triggers fatal cardiac arrhythmias (sudden cardiac death (SCD)) and contributes to atrial/ventricular fibrillations and heart-muscle dysfunction in heart failure.

Accordingly, in one aspect, the present invention provides a method for limiting or preventing a decrease in the level of RyR2-bound FKBP12.6 in a subject who has, or is a candidate for, atrial fibrillation, by administering to the subject an amount of JTV-519 effective to limit or prevent a decrease in the level of RyR2-bound FKBP12.6 in the subject, wherein the RyR2 is atrial RyR2. Also provided is a use of JTV-519 in a method for limiting or preventing a decrease in the level of RyR2-bound FKBP12.6 in a subject who has, or is a candidate for, atrial fibrillation.

In another aspect, the present invention provides a method for treating or preventing atrial fibrillation in a subject, by administering to the subject an amount of JTV-519 effective to limit or prevent a decrease in the level of RyR2-bound FKBP12.6 in the subject, thereby treating or preventing atrial fibrillation in the subject. In one embodiment, the amount of JTV-519 effective to limit or prevent a decrease in the level of RyR2-bound FKBP12.6 in the subject is an amount of JTV-519 effective to treat or prevent atrial fibrillation in the subject.

In still another aspect, the present invention provides a method for limiting or preventing a decrease in the level of RyR2-bound FKBP12.6 in a subject, by administering a 1,4-benzothiazepine derivative to the subject, in an amount effective to limit or prevent a decrease in the level of RyR2-bound FKBP12.6 in the subject, wherein the 1,4-benzothiazepine derivative is selected from the group consisting of:

(a)

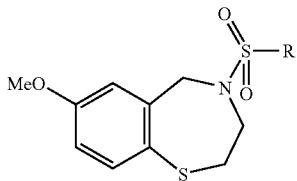

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl;

(b)

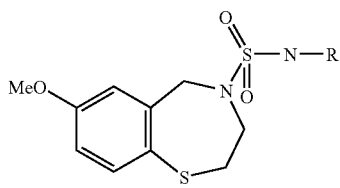

wherein R=aryl, alkyl, —(CH$_2$)$_n$NR'$_2$, or —(CH$_2$)$_n$SR', and n=0, 1, 2, or 3, and R'=alkyl or cycloalkyl;

(c)

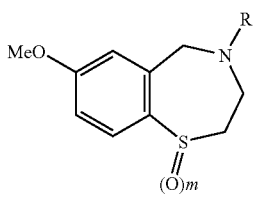

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2;

(d)

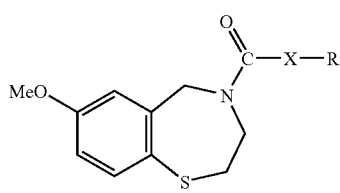

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O;

(e)

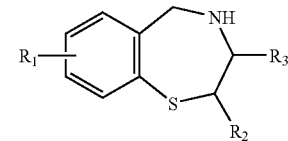

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl;

(f)

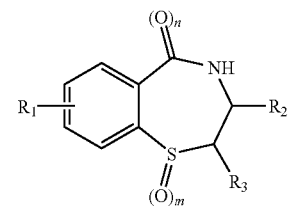

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein m=0, 1, or 2; and wherein n=0 or 1;

(g)

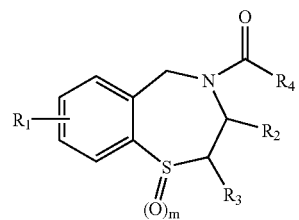

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein R4=H, halide, alkenyl, carboxylic acid, or an alkyl containing O, S, or N; and wherein m=0, 1, or 2; and (h) any oxidized form thereof. Also provided are uses of these 1,4-benzothiazepine derivatives in methods for limiting or preventing a decrease in the level of RyR2-bound FKBP12.6 in a subject.

In yet another aspect, the present invention provides a method for treating or preventing a cardiac arrhythmia, heart failure, and/or exercise-induced sudden cardiac death in a subject, comprising administering a 1,4-benzothiazepine derivative to the subject, in an amount effective to limit or prevent a decrease in the level of RyR2-bound FKBP12.6 in the subject, wherein the 1,4-benzothiazepine derivative is selected from the group consisting of:

(a)

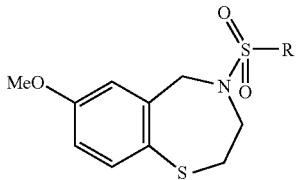

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl;

(b)

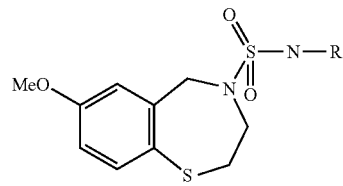

wherein R=aryl, alkyl, —(CH$_2$)$_n$NR'$_2$, or —(CH$_2$)$_n$SR', and n=0, 1, 2, or 3, and R'=alkyl or cycloalkyl;

(c)

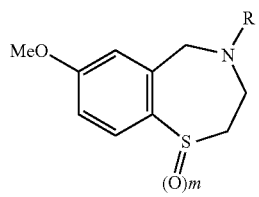

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2;

(d)

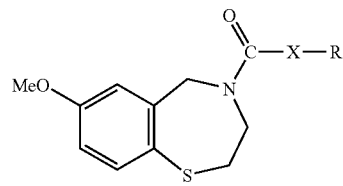

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O;

(e)

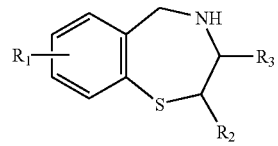

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl;

(f)

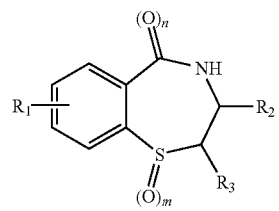

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein m=0, 1, or 2; and wherein n=0 or 1;

(g)

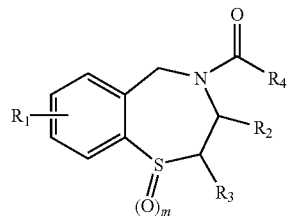

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein R4=H, halide, alkenyl, carboxylic acid, or an alkyl containing O, S, or N; and wherein m=0, 1, or 2; and (h) any oxidized form thereof.

In a further aspect, the present invention provides a method for treating or preventing a cardiac arrhythmia, heart failure, and/or exercise-induced sudden cardiac death in a subject, comprising administering a 1,4-benzothiazepine derivative to the subject, in an amount effective to treat or prevent the cardiac arrhythmia, heart failure, and/or exercise-induced sudden cardiac death in the subject, wherein the 1,4-benzothiazepine derivative is selected from the group consisting of:

(a)

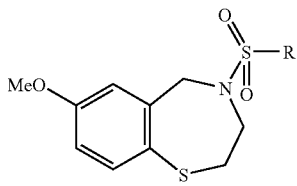

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl;

(b)

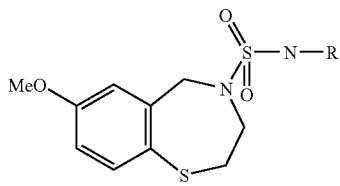

wherein R=aryl, alkyl, —(CH$_2$)$_n$NR'$_2$, or —(CH$_2$)$_n$SR', and n=0, 1, 2, or 3, and R'=alkyl or cycloalkyl;

(c)

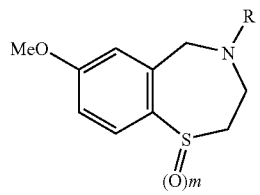

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2;

(d)

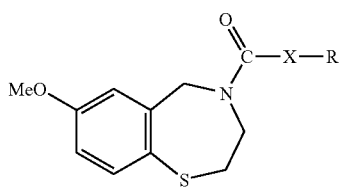

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O;

(e)

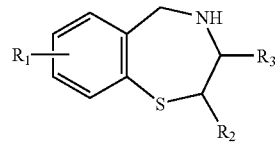

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl;

(f)

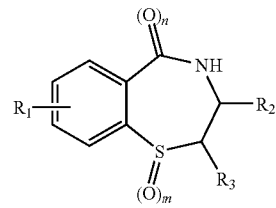

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein m=0, 1, or 2; and wherein n=0 or 1;

(g)

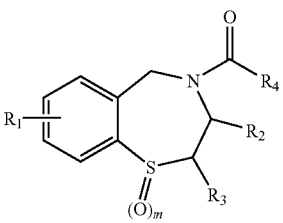

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein R4=H, halide, alkenyl, carboxylic acid, or an alkyl containing O, S, or N; and wherein m=0, 1, or 2; and (h) any oxidized form thereof. Also provided are uses of these 1,4-benzothiazepine derivatives in methods for treating or preventing a cardiac arrhythmia, heart failure, and/or exercise-induced sudden cardiac death in a subject.

In still another aspect, the present invention provides a method for identifying an agent for use in treating or preventing atrial fibrillation or heart failure, by: (a) obtaining or generating a culture of cells containing RyR2; (b) contacting the cells with a candidate agent; (c) exposing the cells to one or more conditions known to increase phosphorylation of RyR2 in cells; and (d) determining if the agent limits or prevents a decrease in the level of RyR2-bound FKBP12.6 in the cells. In one embodiment, this method further comprises the step of: (e) determining if the agent has an effect on an RyR2-associated biological event in the cells. Also provided are an agent identified by this method, and a use of the agent in methods of treating and preventing atrial fibrillation and heart failure.

In yet another aspect, the present invention provides a method for identifying an agent for use in treating or preventing atrial fibrillation or heart failure, by: (a) obtaining or generating an animal containing RyR2; (b) administering a candidate agent to the animal; (c) exposing the animal to one or more conditions known to increase phosphorylation of RyR2 in cells; and (d) determining if the agent limits or prevents a decrease in the level of RyR2-bound FKBP12.6 in the animal. In one embodiment, this method further comprises the step of: (e) determining if the agent has an effect on an RyR2-associated biological event in the animal. Also provided are an agent identified by this method, and a use of the agent in methods of treating and preventing atrial fibrillation and heart failure.

Additional aspects of the present invention will be apparent in view of the description which follows.

DETAILED DESCRIPTION OF THE INVENTION

Figure 1:
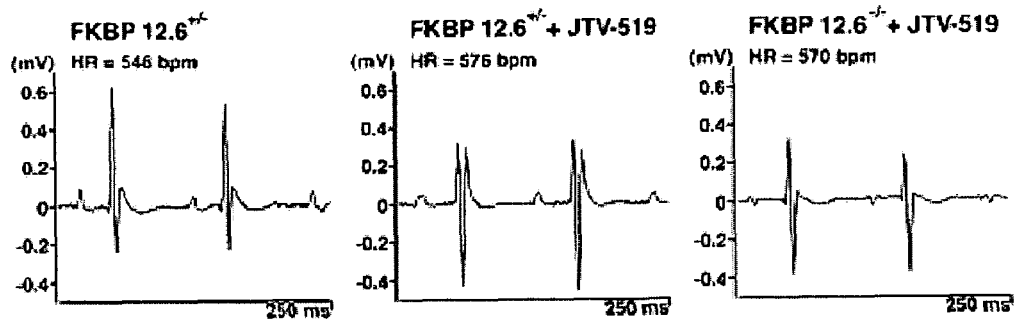
FIG. 1 demonstrates that JTV-519 prevents exercise-induced ventricular arrhythmias in FKBP12.6$^{+/-}$ mice. (A) Representative ambulatory electrocardiograms of an untreated FKBP12.6$^{+/-}$ mouse, an FKBP12.6$^{+/-}$ mouse treated with JTV-519, and an FKBP12.6$^{-/-}$ mouse treated with JTV-519. There were no significant differences in heart rate, or in any of the measured ECG parameters. (B) upper tracing: Example of sustained polymorphic ventricular tachycardia, recorded in an untreated FKBP12.6+/−mouse subjected to exercise testing and injection with 1.0 mg/kg epinephrine. middle tracing: Electro-cardiogram of a JTV-519-treated FKBP12.6$^{+/-}$ mouse following the same protocol; no arrhythmias were detected. bottom tracing: Exercise-induced ventricular tachycardia (VT) in an FKBP12.6$^{-/-}$ mouse treated with JTV-519. The dotted line represents 16.31 seconds of VT that are not shown in the figure. 'P' indicates a P-wave, which is indicative of sinus rhythm following ventricular tachycardia. (C) Bar graph showing quantification of sudden cardiac death (left), sustained ventricular tachycardias (>10 beats, middle), and non-sustained ventricular tachycardias (3-10 abnormal beats, right) in FKBP12.6$^{+/-}$ and FKBP12.6$^{-/-}$ mice, either treated or not treated with JTV-519, respectively. It should be noted that treatment with JTV-519 completely prevented exercise- and epinephrine-induced arrhythmias in FKBP12.6$^{+/-}$ mice treated with JTV-519 (n=9), as compared with untreated FKBP12.6$^{+/-}$ mice (n=10) or JTV-519-treated FKBP12.6$^{-/-}$ mice (n=5), suggesting that JTV-519 prevents arrhythmias and sudden death in FKBP12.6$^{+/-}$ mice by rebinding FKBP12.6 to RyR2.
Figure 1:
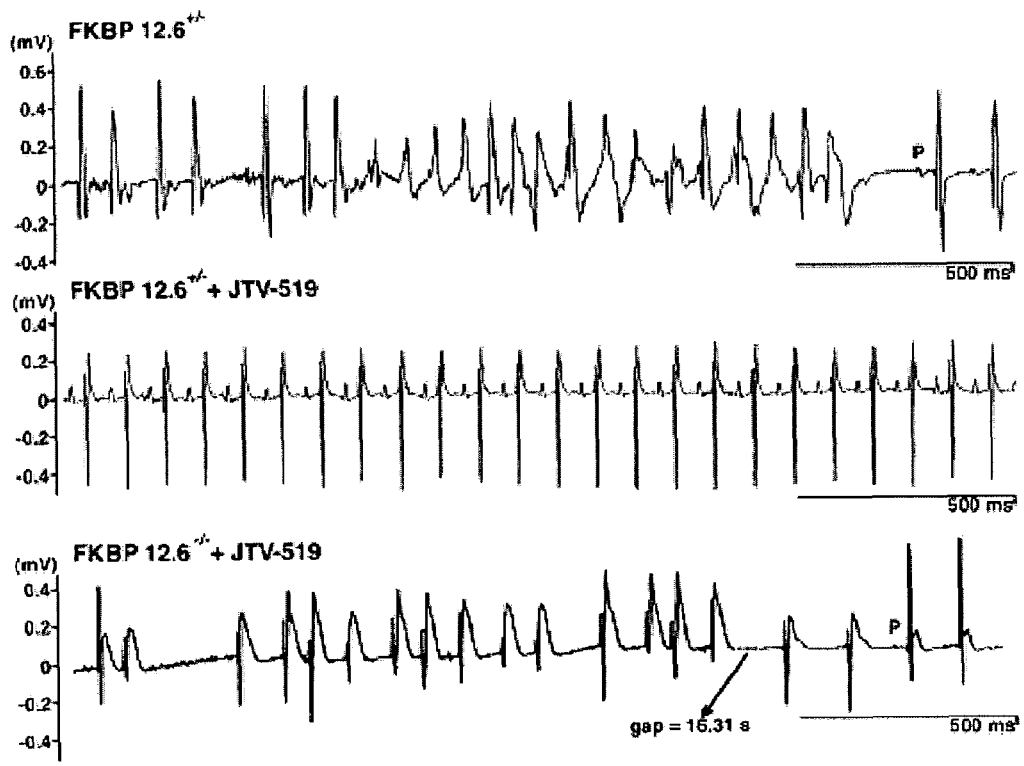
Figure 1:
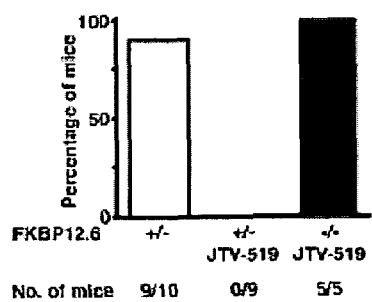
Figure 1:
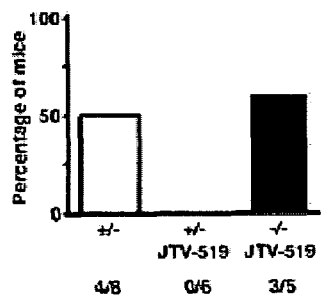
Figure 1:
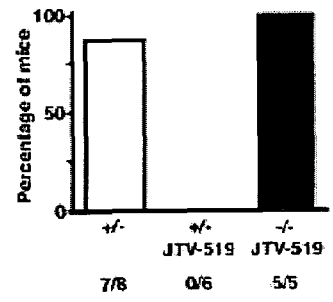

Phosphorylation of cardiac RyR2 by protein kinase (PKA) is an important part of the "fight or flight" response; it increases cardiac EC-coupling gain by augmenting the amount of Ca$^{2+}$ released for a given trigger (Marks, A. R., Cardiac intracellular calcium release channels: role in heart failure. *Circ. Res.*, 87:8-11, 2000). This signaling pathway provides a mechanism by which activation of the sympathetic nervous system, in response to stress, results in increased cardiac output required to meet the metabolic demands of the stress responses. Upon binding of catecholamines, β1- and β2-adrenergic receptors activate adenylyl cyclase via a stimulatory G-protein, Gα$_s$. Adenylyl cyclase increases intracellular cyclic adenosine monophosphate (cAMP) levels, which activate the cAMP-dependent PKA. PKA phosphorylation of RyR2 increases the open probability of the channel by dissociating calstabin2 (FKBP12.6) from the channel complex. This, in turn, increases the sensitivity of RyR2 to Ca$^{2+}$-dependent activation (Hain et al., Phosphorylation modulates the function of the calcium release channel of sarcoplasmic reticulum from cardiac muscle. *J. Biol. Chem.*, 270:2074-81, 1995; Valdivia et al., Rapid adaptation of cardiac ryanodine receptors: modulation by Mg$^{2+}$ and phosphorylation. *Science*, 267:1997-2000, 1995; Marx et al., PKA phosphorylation dissociates FKBP12.6 from the calcium release channel (ryanodine receptor): defective regulation in failing hearts. *Cell*, 101:365-76, 2000).

Failing hearts (e.g., in patients with heart failure and in animal models of heart failure) are characterized by a maladaptive response that includes chronic hyperadrenergic stimulation (Bristow et al., Decreased catecholamine sensitivity and beta-adrenergic-receptor density in failing human hearts. *N. Engl. J. Med.*, 307:205-11, 1982). The pathogenic significance of this stimulation in heart failure is supported by therapeutic strategies that decrease beta-adrenergic stimulation and left ventricular myocardial wall stress, and potently reverse ventricular remodeling (Barbone et al., Comparison of right and left ventricular responses to left ventricular assist device support in patients with severe heart failure: a primary role of mechanical unloading underlying reverse remodeling. *Circulation*, 104:670-75, 2001; Eichhorn and Bristow, Medical therapy can improve the biological properties of the chronically failing heart. A new era in the treatment of heart failure. *Circulation*, 94:2285-96, 1996). In heart failure, chronic beta-adrenergic stimulation is associated with the activation of beta-adrenergic receptors in the heart, which, through coupling with G-proteins, activate adenylyl cyclase and thereby increase intracellular cAMP concentration. cAMP activates cAMP-dependent PKA, which has been shown to induce hyperphosphorylation of RyR2. Thus, chronic heart failure is a chronic hyperadrenergic state (Chidsey et al., Augmentation of plasma norepinephrine response to exercise in patients with congestive heart failure. *N. Engl. J. Med.*, 267:650, 1962) that results in several pathologic consequences, including PKA hyperphosphorylation of RyR2 (Marx et al., PKA phosphorylation dissociates FKBP12.6 from the calcium release channel (ryanodine receptor): defective regulation in failing hearts. *Cell*, 101:365-76, 2000).

The PKA hyperphosphorylation of RyR2 has been proposed as a factor contributing to depressed contractile function and arrhythmogenesis in heart failure (Marks et al., Progression of heart failure: is protein kinase a hyperphosphorylation of the ryanodine receptor a contributing factor? *Circulation*, 105:272-75, 2002; Marx et al., PKA phosphorylation dissociates FKBP12.6 from the calcium release channel (ryanodine receptor): defective regulation in failing hearts. *Cell*, 101:365-76, 2000). Consistent with this hypothesis, PKA hyperphosphorylation of RyR2 in failing hearts has been demonstrated in vivo, both in animal models and in patients with heart failure undergoing cardiac transplantation (Antos et al., Dilated cardiomyopathy and sudden death resulting from constitutive activation of protein kinase A. *Circ. Res.*, 89:997-1004, 2001; Marx et al., PKA phosphorylation dissociates FKBP12.6 from the calcium release channel (ryanodine receptor): defective regulation in failing hearts. *Cell*, 101:365-76, 2000; Ono et al., Altered interaction of FKBP12.6 with ryanodine receptor as a cause of abnormal $Ca^{2+}$ release in heart failure. *Cardiovasc. Res.*, 48:323-31, 2000; Reiken et al., Beta-adrenergic receptor blockers restore cardiac calcium release channel (ryanodine receptor) structure and function in heart failure. *Circulation*, 104:2843-48, 2001; Semsarian et al., The L-type calcium channel inhibitor diltiazem prevents cardiomyopathy in a mouse model. *J. Clin. Invest.*, 109:1013-20, 2002; Yano et al., Altered stoichiometry of FKBP12.6 versus ryanodine receptor as a cause of abnormal $Ca^{2+}$ leak through ryanodine receptor in heart failure. *Circulation*, 102:2131-36, 2000).

In failing hearts, the hyperphosphorylation of RyR2 by PKA induces the dissociation of the regulatory FKBP12.6 subunit from the RyR2 channel (Marx et al., PKA phosphorylation dissociates FKBP12.6 from the calcium release channel (ryanodine receptor): defective regulation in failing hearts. *Cell*, 101:365-76, 2000). This causes marked changes in the biophysical properties of the RyR2 channel. Such changes are evidenced by increased open probability (Po) due to an increased sensitivity to $Ca^{2+}$-dependent activation (Brillantes et al., Stabilization of calcium release channel (ryanodine receptor) function by FK506-binding protein. *Cell*, 77:513-23, 1994; Kaftan et al., Effects of rapamycin on ryanodine receptor/$Ca^{2+}$-release channels from cardiac muscle. *Circ. Res.*, 78:990-97, 1996); destabilization of the channel, resulting in subconductance states; and impaired coupled gating of the channels, resulting in defective EC coupling and cardiac dysfunction (Marx et al., Coupled gating between individual skeletal muscle $Ca^{2+}$ release channels (ryanodine receptors). *Science*, 281:818-21, 1998). Thus, PKA-hyperphosphorylated RyR2 is very sensitive to low-level $Ca^{2+}$ stimulation, and this manifests itself as an SR $Ca^{2+}$ leak through the hyperphosphorylated channel.

The maladaptive response to stress in heart failure results in depletion of FKBP12.6 from the channel macromolecular complex. This leads to a shift to the left in the sensitivity of RyR2 to $Ca^{2+}$-induced $Ca^{2+}$ release, resulting in channels that are more active at low-to-moderate [$Ca^{2+}$](Marx et al., PKA phosphorylation dissociates FKBP12.6 from the calcium release channel (ryanodine receptor): defective regulation in failing hearts. *Cell*, 101:365-76, 2000; Yamamoto et al., Abnormal $Ca^{2+}$ release from cardiac sarcoplasmic reticulum in tachycardia-induced heart failure. *Cardiovasc. Res.*, 44:146-55, 1999; Yano et al., Altered stoichiometry of FKBP12.6 versus ryanodine receptor as a cause of abnormal $Ca^{2+}$ leak through ryanodine receptor in heart failure. *Circulation*, 102:2131-36, 2000). Over time, the increased "leak" through RyR2 results in resetting of the SR $Ca^{2+}$ content to a lower level, which in turn reduces EC coupling gain and contributes to impaired systolic contractility (Marx et al., PKA phosphorylation dissociates FKBP12.6 from the calcium release channel (ryanodine receptor): defective regulation in failing hearts. *Cell*, 101:365-76, 2000).

A subpopulation of RyR2 channels that are particularly "leaky" can release SR $Ca^{2+}$ during the resting phase of the cardiac cycle, diastole. This results in depolarizations of the cardiomyocyte membrane known as delayed after-depolarizations (DADs), which are known to trigger fatal ventricular cardiac arrhythmias (Wehrens et al., FKBP12.6 deficiency and defective calcium release channel (ryanodine receptor) function linked to exercise-induced sudden cardiac death. *Cell*, 113:829-40, 2003).

In structurally-normal hearts, a similar phenomenon may be at work. Specifically, it is known that exercise and stress induce the release of catecholamines that activate beta-adrenergic receptors in the heart. Activation of the beta-adrenergic receptors leads to hyperphosphorylation of RyR2 channels. Evidence also suggests that the hyperphosphorylation of RyR2, resulting from beta-adrenergic-receptor activation, renders mutated RyR2 channels more likely to open in the relaxation phase of the cardiac cycle, increasing the likelihood of arrhythmias.

The inventors have shown herein that JTV-519 prevents heart failure in a rat model of post-MI heart failure. In this animal model, JTV-519 improved cardiac function, in terms of reduced diastolic dysfunction and improved systolic function. Furthermore, the inventors have demonstrated that the skeletal-muscle form of the RyR channel, RyR1, is also defective (or leaky) in heart-failure skeletal muscle, due to PKA-hyperphosphorylation (Reiken et al., PKA phosphorylation dissociates FKBP12 from the calcium release channel (ryanodine receptor) in skeletal muscle: defective regulation in heart failure. *J. Cell Biol.*, 160:919-28, 2003). Therefore, it is expected that JTV-519 will also improve skeletal-muscle function in patients with heart failure. As such, JTV-519 provides a novel therapeutic approach to treat two major symptoms in heart failure—early fatigue and shortness of breath —which are caused by skeletal-muscle weakness in the extremities and in the diaphragm, respectively.

As discussed above, catecholaminergic polymorphic ventricular tachycardia (CPVT) is an inherited disorder in individuals with structurally-normal hearts. It is characterized by stress-induced ventricular tachycardia, a lethal arrhythmia that may cause sudden cardiac death (SCD). Mutations in RyR2 channels, located on the sarcoplasmic reticulum (SR), have been linked to CPVT.

All individuals with CPVT have exercise-induced cardiac arrhythmias. The inventors previously showed that exercise-induced arrhythmias and sudden death (in patients with CPVT) result from a reduced affinity of FKBP12.6 for RyR2. Herein, the inventors have demonstrated that exercise activates RyR2 as a result of phosphorylation by adenosine-3', 5'-monophosphate-dependent protein kinase (PKA).

To determine the molecular mechanisms underlying the fatal cardiac arrhythmias in CPVT, the inventors studied CPVT-associated mutant RyR2 channels (e.g., S2246L, R2474S, N4104K, R4497C). Mutant RyR2 channels, which had normal function in planar lipid bilayers under basal conditions, were more sensitive to activation by PKA phosphorylation—exhibiting increased activity (open probability) and prolonged open states, as compared with wild-type channels. In addition, PKA-phosphorylated mutant RyR2 channels were resistant to inhibition by $Mg^{2+}$, a physiological inhibitor of RyR2 channels, and showed reduced binding to FKBP12.6 (which stabilizes the channel in the closed state). These findings indicate that, during exercise, when the RyR2 channels are PKA-hosphorylated, the mutant CPVT channels are more likely to open in the relaxation phase of the cardiac cycle (diastole), increasing the likelihood of occurrence of arrhythmias triggered by the SR $Ca^{2+}$ leak. Since heart failure is a leading cause of death worldwide, methods to repair the leak in RyR2 could prevent fatal arrhythmias in millions of patients.

The inventors have further demonstrated herein that the experimental drug, JTV-519, a 1,4-benzothiazepine derivative, prevents lethal ventricular arrhythmias in mice heterozygous for the FKBP12.6 gene. It has recently been shown that JTV-519 reduces diastolic SR $Ca^{2+}$ leak in an animal model of heart failure (Yano et al., FKBP12.6-mediated stabilization of calcium-release channel (ryanodine receptor) as a novel therapeutic strategy against heart failure. *Circulation*, 107: 477-84, 2003; Kohno et al., A new cardioprotective agent, JTV519, improves defective channel gating of ryanodine receptor in heart failure. *Am. J. Physiol. Heart Circ. Physiol.*, 14:14, 2002). In the present study, the inventors examined JTV-519's efficacy and mechanism of action in a cardiac arrhythmia model. For their in vivo experiments, the inventors required gram quantities of JTV-519 (4-[3-(4-benzylpiperidin-1-yl)propionyl]-7-methoxy-2,3,4,5-tetrahydro-1,4-benzothiazepine monohydrochloride).

To test for cardiac arrhythmias, $FKBP12.6^{+/-}$ and $FKBP12.6^{-/-}$ mice were subjected to a previously-described exercise protocol (Wehrens et al., FKBP12.6 deficiency and defective calcium release channel (ryanodine receptor) function linked to exercise-induced sudden cardiac death. *Cell*, 113:829-40, 2003; Mohler et al., Ankyrin-B mutation causes type 4 long-QT cardiac arrhythmia and sudden cardiac death. *Nature*, 421:634-39, 2003). While 88% of the $FKBP12.6^{+/-}$ mice (7 of 8) displayed ventricular tachyarrhythmias (VT) or syncopal events during the protocol, none of the $FKBP12.6^{+/-}$ mice (0 of 6) pretreated with JTV-519 developed arrhythmias or syncopal events (FIG. 1). Furthermore, 90% of $FKBP12.6^{+/-}$ mice (9 of 10) died during or following exercise, whereas none of the JTV-519-treated $FKBP12.6^{+/-}$ mice (0 of 9) died (FIG. 1C). In contrast to pretreated $FKBP12.6^{+/-}$ mice, 100% of the $FKBP12.6^{-/-}$ mice (5 of 5) treated with JTV-519 developed VT during the stress protocol and died, despite JTV-519 treatment (FIG. 1C). Taken together, these data suggest that FKBP12.6 is required for the anti-arrhythmic actions of JTV-519.

In order to characterize further the anti-arrhythmic properties of JTV-519, the inventors subjected $FKBP12.6^{+/+}$, $FKBP12.6^{+/-}$, and $FKBP12.6^{-/-}$ mice to programmed electrical stimulation protocols. VTs were induced by rapid overdrive pacing in 71% of $FKBP12.6^{+/-}$ mice (5 of 7), but not in wild-type FKBP12.6+/+mice (P<0.05, n=5), following injection of 0.5 mg/kg isoproterenol. $FKBP12.6^{+/-}$ mice pretreated with JTV-519 (0.5 mg/kg/h) were significantly less susceptible to overdrive-pacing-induced VTs, as compared with untreated $FKBP12.6^{+/-}$ mice (1 of 7 vs. 5 of 7; P<0.05). Contrastingly, 67% of $FKBP12.6^{-/-}$ mice (4 of 6) pretreated with JTV-519 developed VTs during overdrive pacing.

VTs could be induced with a single premature beat in 71% of $FKBP12.6^{+/-}$ mice (5 of 7). No VTs were observed in the 7 $FKBP12.6^{+/-}$ mice pretreated with JTV-519. Using a double premature beat protocol (S1-S2-S3), VTs were reproducibly induced in 100% of untreated $FKBP12.6^{+/-}$ mice (7 of 7). Treatment with JTV-519 completely eliminated inducible VTs in $FKBP12.6^{+/-}$ mice (7 of 7). JTV-519 treatment did not prevent VTs in $FKBP12.6^{-/-}$ mice, supporting the concept that FKBP12.6 is required for the anti-arrhythmic actions of JTV-519.

Figure 2:
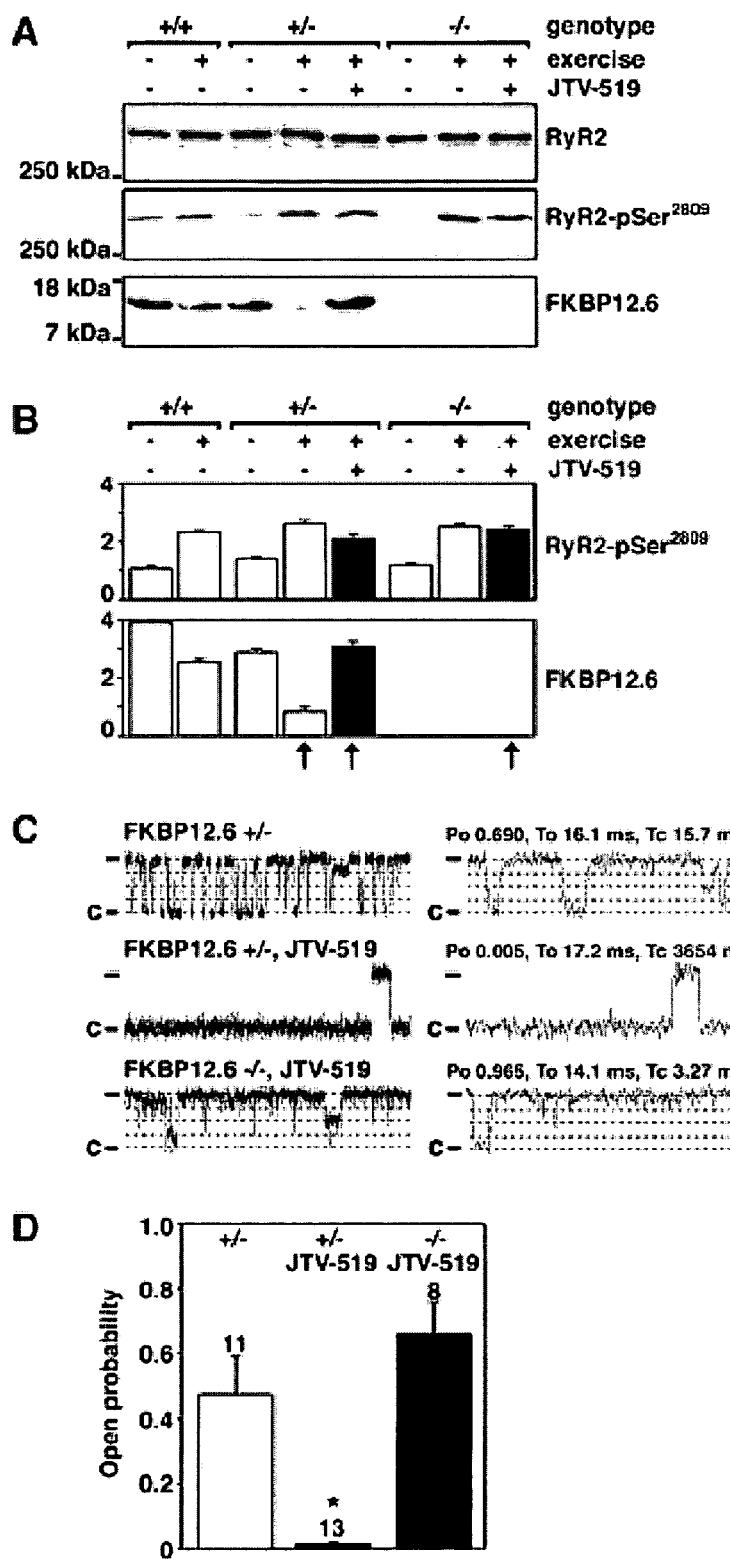
FIG. 2 shows that JTV-519 prevents exercise-induced sudden cardiac death (SCD) by increasing the affinity of FKBP12.6 for RyR2 in FKBP12.6$^{+/-}$ mice. (A-B) Cardiac ryanodine receptors (RyR2) were immunoprecipitated using RyR2-5029 antibody. Shown are immunoblots (A) and bar graphs (B) representing the quantified amounts of RyR2, PKA-phosphorylated RyR2 (RyR2-pSer$^{2809}$ antibody), and FKBP12.6 in wild-type (FKBP12.6$^{+/+}$) mice, FKBP12.6$^{+/-}$ mice, and FKBP12.6$^{-/-}$ under resting conditions, and following exercise, either in the absence or presence of JTV-519, respectively. Under resting conditions, ~70% of FKBP12.6 is associated with RyR2 in FKBP12.6$^{+/-}$ mice. Following exercise testing, the amount of FKBP12.6 associated with the RyR2 complex was dramatically decreased in FKBP12.6$^{+/-}$ mice, but this could be rescued by treatment with JTV-519. (C) RyR2 single channels were isolated from hearts obtained following exercise testing and epinephrine injection. Shown are channels from FKBP12.6$^{+/-}$ mice, with and without pre-treatment with JTV-519, and channels from FKBP12.6$^{-/-}$ mice following JTV-519 pre-treatment. It should be noted that RyR2-channel function was normalized in the exercised FKBP12.6$^{+/-}$ mouse treated with JTV-519. The representative single channel from an exercised FKBP12.6$^{-/-}$ mouse after JTV-519 treatment shows that FKBP12.6 in the heart is required for the action of JTV-519. The dotted lines represent incomplete channel openings, or 'subconductance' openings, and are indicative of FKBP12.6-depleted RyR2 channels. Tracings on the left represent 5.0 sec, while tracings on the right represent 500 msec. In the figure, Po=open probability; To=average open times; Tc=average closed times; and c=closed state of the channel. (D) Summary bar graph showing average open probabilities of single RyR2 channels (see above). JTV-519 dramatically reduces the open probability of RyR2 from FKBP12.6$^{+/-}$ mice following exercise testing at diastolic calcium concentrations (150 nM).

Previously, the inventors demonstrated that PKA phosphorylation of RyR2 at Ser2809 causes dissociation of FKBP12.6 from the RyR2 channel (Marx et al., PKA phosphorylation dissociates FKBP12.6 from the calcium release channel (ryanodine receptor): defective regulation in failing hearts. *Cell*, 101:365-76, 2000). In the present study, pretreatment with JTV-519 (0.5 mg/kg/h) did not affect the degree of PKA phosphorylation of RyR2 in $FKBP12.6^{+/-}$ and $FKBP12.6^{-/-}$ mice (FIG. 2). Compared to $FKBP12.6^{+/+}$ mice, RyR2 complexes from $FKBP12.6^{+/-}$ mice were significantly more depleted of FKBP12.6 following exercise (*P<0.05). Pretreatment with JTV-519, however, prevented the loss of FKBP12.6 from the RyR2 macromolecular complex in $FKBP12.6^{+/-}$ mice during exercise (FIG. 2; *P<0.05).

The open probabilities (Po) of RyR2 channels from $FKBP12.6^{+/-}$ mice subjected to exercise were significantly increased, as compared with channels from exercised $FKBP12.6^{+/+}$ mice (+/−: 0.47±0.12, n=11; +/+: 0.04±0.01, n=13; P<0.05). Treatment of exercised $FKBP12.6^{+/-}$ mice with JTV-519 (0.5 mg/kg/h) significantly reduced the channel Po (0.02±0.01, n=13), as compared with non-treated exercised mice (FIG. 2). This observation is consistent with increased amounts of FKBP12.6 in the RyR2 complex (FIG. 2). In contrast, JTV-519 treatment of exercised $FKBP12.6^{-/-}$ mice did not result in channels with a low Po.

RyR2 single channels were examined with low cis (cytosolic) [$Ca^{2+}$] of 150 nM, using $Ca^{2+}$ as the charge carrier. These conditions simulate those in the heart during diastole, when the RyR2 channels should have a low open probability in order to prevent the diastolic SR $Ca^{2+}$ leak that can trigger cardiac arrhythmias. Thus, the significant reduction in the RyR2 Po, as observed in JTV-519-treated exercised $FKBP12.6^{+/-}$ mice, suggests that the RyR2 channels will not be "leaky" during diastole d, which is consistent with the absence of observed arrhythmias.

Figure 3:
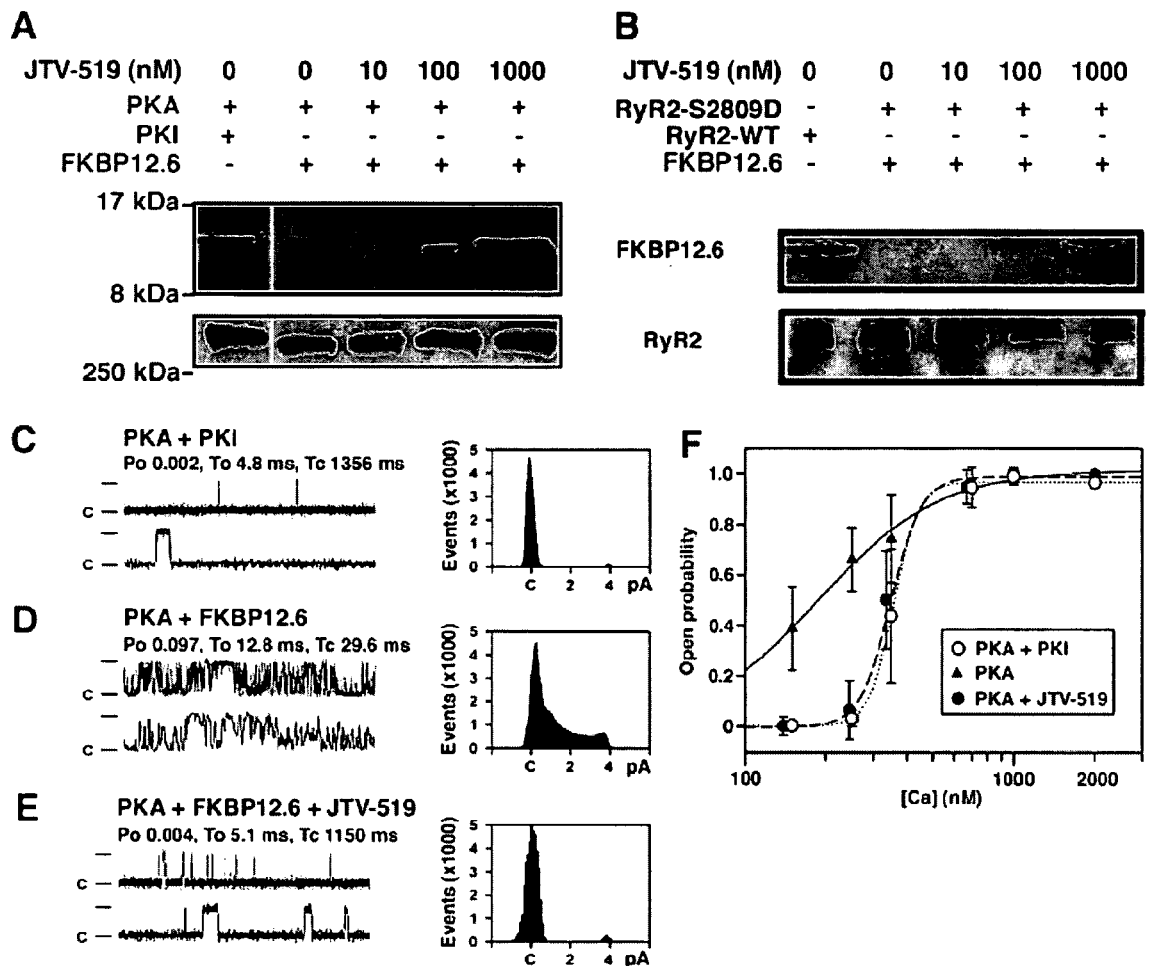
FIG. 3 illustrates that JTV-519 normalizes RyR2-channel gating by increasing FKBP12.6 binding affinity to PKA-phosphorylated RyR2 channels. (A, B) Canine cardiac SR membranes (A) and recombinantly-expressed RyR2 channels (B) were prepared as described previously (Kaftan et al., Effects of rapamycin on ryanodine receptor/Ca$^{(2+)}$-release channels from cardiac muscle. *Circ. Res.,* 78:990-97, 1996). (A) Ryanodine receptors (RyR2) were phosphorylated with PKA catalytic subunit (40 U; Sigma Chemical Co., St. Louis, Mo.), in the presence or absence of the PKA inhibitor, PKI$_{5-24}$, in phosphorylation buffer (8 mM MgCl$_2$, 10 mM EGTA, and 50 mM Tris/PIPES; pH 6.8). Samples were centrifuged at 100,000×g for 10 min, and washed three times in imidazole buffer (10 mM imidazole; pH 7). Recombinantly-expressed FKBP12.6 (final concentration=250 nM) was added to the samples, in the absence or presence of different concentrations of JTV-519. After a 60-min incubation, samples were centrifuged at 100,000×g for 10 min, and washed twice in imidazole buffer. Samples were heated to 95° C., and size-fractionated using SDS-PAGE. Immunoblotting of the SR microsomes was performed, as previously described (Jayaraman et al., FK506 binding protein associated with the calcium release channel (ryanodine receptor). *J. Biol. Chem.,* 267:9474-77, 1992), with anti-FKBP12.6 antibody (1:1,000) and anti-RyR2-5029 antibody (1:3,000). The figure demonstrates that JTV-519 enables FKBP12.6 to bind to: (A) PKA-phosphorylated RyR2 (partial binding at 100 nM; complete binding at 1000 nM) or (B) RyR2-S2809D mutant channels, which are constitutively PKA-phosphorylated RyR2 channels. (C-E) Single-channel studies showing increased open probability of RyR2 following PKA phosphorylation (D), as compared with PKA phosphorylation in the presence of the specific PKA inhibitor, PKI$_{5-24}$ (C). Single-channel function was normalized in PKA-phosphorylated RyR2 incubated with FKBP12.6 in the presence of JTV-519 (E). Channel openings are upward, the dash indicates the level of full openings (4 pA), and the letter 'c' indicates the closed state. Channels are shown at compressed (5 sec, upper tracing) and expanded (500 msec, lower tracing) time scales, and recordings are at 0 mV. Amplitude histograms (right) revealed increased activity and subconductance openings in PKA-phosphorylated RyR2, but not following treatment with JTV-519 and FKBP12.6. (F) Normalized plot of open probability as a function of cytosolic [Ca$^{2+}$]. Incubation of PKA-phosphorylated RyR2 with FKBP12.6 in the presence of JTV-519 shifted the Ca$^{2+}$-dependence of RyR2 activation towards the right, making it similar to the Ca$^{2+}$-dependence of unphosphorylated channels.

To further examine the mechanism by which JTV-519 prevents VTs, the inventors simulated the conditions of exercise using PKA phosphorylation of wild-type RyR2 (RyR2-WT) channels. PKA-phosphorylated RyR2 channels were then incubated with FKBP12.6 (250 nM), in the presence of increasing concentrations of JTV-519. Incubation with 100 nM or 1000 nM JTV-519 induced the binding of FKBP12.6 to PKA-phosphorylated RyR2 (FIG. 3). JTV-519 also induced FKBP12.6 binding to mutant RyR2-S2809D channels that mimic constitutively-PKA-phosphorylated RyR2 channels (FIG. 3).

The affinity of FKBP12.6 for PKA-phosphorylated RyR2 channels was significantly increased by addition of JTV-519. The dissociation constants ($K_d$s) for FKBP12.6 binding to the channels were: 148±59.0 nM for RyR2-WT+PKA+PKI$_{5-24}$ (PKA inhibitor); 1972±39.9 nM for RyR2-WT+PKA; 158±56.4 nM for RyR2+PKA+JTV-519 (P<0.05, n=2 for PKA-phosphorylated channels vs. PKA-phosphorylated channels with JTV-519) (FIG. 3). Similar results were obtained using RyR2-S2809D mutant channels (that mimic constitutively-PKA-phosphorylated channels). The $K_d$s for FKBP12.6 binding were: 2123±104 nM for RyR2-S2809D; and 428±39 nM for RyR2-S2809D+JTV-519. PKA phosphorylation of RyR2 activated the channel (Po=0.01±0.002 (PKA+PKI; n=11) vs. Po=0.40±0.02 (PKA; n=12; P<0.05). Addition of FKBP12.6 (250 nM) to the PKA-phosphorylated RyR2-WT channels did not lower the Po. However, addition of 1 µM JTV-519 plus FKBP12.6 reduced the Po to levels comparable to the non-PKA-phosphorylated channels (Po=0.002±0.001; n=13; P<0.05).

Taken together, the inventors' results show that depletion of FKBP12.6 from the RyR2 macromolecular complex—which is associated with increased RyR2 open probability, ventricular tachycardias, and sudden cardiac death in FKBP12.6$^{+/-}$ mice—is reversed by treatment with the 1,4-benzodiazepine derivative, JTV-519. Therefore, the inventors have identified a novel molecular mechanism for treating ventricular arrhythmias: increases in the affinity of RyR2 for FKBP12.6 prevent diastolic SR calcium leaks that trigger arrhythmias. Since FKBP12.6 deficiency in the RyR2 macromolecular complex is a common feature in heart failure (Marx et al., PKA phosphorylation dissociates FKBP12.6 from the calcium release channel (ryanodine receptor): defective regulation in failing hearts. *Cell*, 101:365-76, 2000) and in inherited exercise-induced ventricular arrhythmias (Wehrens et al., FKBP12.6 deficiency and defective calcium release channel (ryanodine receptor) function linked to exercise-induced sudden cardiac death. *Cell*, 113:829-40, 2003), it is expected that JTV-519 will provide a novel and specific way to treat the molecular defect in RyR2 which triggers sudden cardiac death.

As discussed above, atrial fibrillation is the most common form of cardiac arrhythmia in humans. To date, it has been established that structural remodeling and electrical remodeling—including shortening of atrial refractoriness, loss of rate-related adaptation of refractoriness (Wijffels et al., Atrial fibrillation begets atrial fibrillation: a study in awake chronically instrumented goats. *Circulation*, 92:1954-68, 1995; Morillo et al., Chronic rapid atrial pacing: structural, functional, and electrophysiological characteristics of a new model of sustained atrial fibrillation. *Circulation*, 91:1588-95, 1995; Elvan et al., Pacing-induced chronic atrial fibrillation impairs sinus node function in dogs: electrophysiological remodeling. *Circulation*, 94:2953-60, 1996; Gaspo et al., Functional mechanisms underlying tachycardia-induced sustained atrial fibrillation in a chronic dog model. *Circulation*, 96:4027-35, 1997), and shortening of the wavelength of re-entrant wavelets—accompany sustained tachycardia (Rensma et al., length of excitation wave and susceptibility to reentrant atrial arrhythmias in normal conscious dogs. *Circ. Res.*, 62:395-410, 1988). This remodeling is likely important in the development, maintenance, and progression of atrial fibrillation. It has also been suggested that calcium handling may play a role in electrical remodeling in atrial fibrillation (Sun et al., Cellular mechanisms of atrial contractile dysfunction caused by sustained atrial tachycardia. *Circulation*, 98:719-27, 1998; Goette et al., Electrical remodeling in atrial fibrillation: time course and mechanisms. *Circulation*, 94:2968-74, 1996; Daoud et al., Effect of verapamil and procainamide on atrial fibrillation-induced electrical remodeling in humans. *Circulation*, 96:1542-50, 1997; Yu et al., Tachycardia-induced change of atrial refractory period in humans: rate dependency and effects of antiarrhythmic drugs. *Circulation*, 97:2331-37, 1998; Leistad et al., Atrial contractile dysfunction after short-term atrial fibrillation is reduced by verapamil but increased by BAY K8644. *Circulation*, 93:1747-54, 1996; Tieleman et al., Verapamil reduces tachycardia-induced electrical remodeling of the atria. *Circulation*, 95:1945-53, 1997).

A variety of mechanisms, based on altered ion-channel function, have been proposed for AF. For example, studies have shown a reduction in the L-type $Ca^{2+}$ current ($I_{Ca,L}$) and transient outward current ($I_{to}$), in the setting of prolonged atrial tachycardia (Yue et al., Ionic remodeling underlying action potential changes in a canine model of atrial fibrillation. *Circ. Res.*, 81:512-25, 1997). The observed downregulation of $I_{Ca,L}$ is likely to explain, at least in part, shortening of AERP and the loss of rate-related adaptation of refractoriness—both of which are hallmarks of the electrical remodeling process that accompanies AF (Yue et al., Ionic remodeling underlying action potential changes in a canine model of atrial fibrillation. *Circ. Res.*, 81:512-25, 1997). In experimental animal models of rapid atrial pacing, and in clinical studies of humans with AF, verapamil has been shown to inhibit electrical remodeling, thereby suggesting that $Ca^{2+}$ overload is involved (Daoud et al., Effect of verapamil and procainamide on atrial fibrillation-induced electrical remodeling in humans. *Circulation*, 96:1542-50, 1997; Leistad et al., Atrial contractile dysfunction after short-term atrial fibrillation is reduced by verapamil but increased by BAY K8644. *Circulation*, 93:1747-54, 1996).

While sarcolemmal ion channels clearly play an important role in the remodeling that accompanies atrial tachycardia and AF, the contribution of intracellular $Ca^{2+}$ handling has not been thoroughly explored. Evidence exists, however, to suggest that aberrant intracellular $Ca^{2+}$ handling does play a role in the remodeling process. Previous studies have demonstrated, for example, that loss of rate adaptation cannot be fully explained by altered sarcolemmal ion currents, such as $I_{Ca,L}$ and $I_{to}$ (Ramirez et al., Mathematical analysis of canine atrial action potentials: rate, regional factors, and electrical remodeling. *Am. J. Physiol. Heart Circ. Physiol.*, 279: H1767-85, 2000; Kneller et al., Remodeling of $Ca^{2+}$-handling by atrial tachycardia: evidence for a role in loss of rate-adaptation. *Cardiovasc. Res.*, 54:416-26, 2002). Studies have also shown that tachycardia-induced changes in intracellular calcium handling also contribute significantly to loss of rate adaptation, which is believed to be critical to the pathogenesis of AF (Sun et al., Cellular mechanisms of atrial contractile dysfunction caused by sustained atrial tachycardia. *Circulation*, 98:719-27, 1998; Kneller et al., Remodeling of $Ca^{2+}$-handling by atrial tachycardia: evidence for a role in loss of rate-adaptation. *Cardiovasc. Res.*, 54:416-26, 2002; Hara et al., Steady-state and nonsteady-state action potentials in fibrillating canine atrium: abnormal rate adaptation and its possible mechanisms. *Cardiovasc. Res.*, 42:455-69, 1999).

In previous studies, atria from a canine model of pacing-induced AF demonstrated a loss of AP-duration-rate adaptation, and altered AP characteristics, which could be reversed by the presence of ryanodine. These observations suggest that the changes result, at least in part, from an intracellular-$Ca^{2+}$-dependent process (Hara et al., Steady-state and nonsteady-state action potentials in fibrillating canine atrium: abnormal rate adaptation and its possible mechanisms. *Cardiovasc. Res.*, 42:455-69, 1999). Furthermore, in the atria of canines with sustained pacing-induced atrial tachycardia, there is a significant reduction in $Ca^{2+}$ transients (Sun et al., Cellular mechanisms of atrial contractile dysfunction caused by sustained atrial tachycardia. *Circulation*, 98:719-27, 1998).

Because $Ca^{2+}$ transients result from sarcolemmal $Ca^{2+}$ entry that triggers $Ca^{2+}$-induced $Ca^{2+}$ release from the SR through RyR2, the results of previous studies suggest that alterations in intracellular-calcium handling accompany the tachycardia-induced remodeling process. Such aberrantly-decreased $Ca^{2+}$ transients have been associated with depressed shortening of isolated atrial myocytes, indicating that calcium handling contributes to the atrial contractile dysfunction accompanying AF (Sun et al., Cellular mechanisms of atrial contractile dysfunction caused by sustained atrial tachycardia. *Circulation*, 98:719-27, 1998).

As disclosed herein, the inventors' studies provide convincing evidence that calcium homeostasis plays an important role in the electrical and contractile remodeling that accompanies sustained atrial tachycardia and AF. Release of SR $Ca^{2+}$ stores by RyR2 stands as an integral component of myocardial $Ca^{2+}$ homeostasis. The regulation of RyR2 has been well characterized in ventricular tissue of canines and humans, and RyR2 has been implicated in diseases of the ventricular myocardium, including heart failure and sudden cardiac death (Marx et al., PKA phosphorylation dissociates FKBP12.6 from the calcium release channel (ryanodine receptor): defective regulation in failing hearts. *Cell*, 101:365-76, 2000; Wehrens et al., FKBP12.6 deficiency and defective calcium release channel (ryanodine receptor) function linked to exercise-induced sudden cardiac death. *Cell*, 113:829-40, 2003; Reiken et al., Beta-blockers restore calcium release channel function and improve cardiac muscle performance in human heart failure. *Circulation*, 107:2459-66, 2003). Despite the evidence that $Ca^{2+}$ handling plays a role in atrial arrhythmias, the regulation and function of the atrial ryanodine receptor has not been well characterized in this setting. In particular, prior to the present invention, the role of this channel in AF was not known.

The inventors confirm herein that, as in the ventricular myocardium, atrial intracellular-calcium-release channels exist as macromolecular complexes. The results of the inventors' co-immunoprecipitation experiments indicate that atrial RyR2 is physically associated with the major regulatory subunit, calstabin2 (FKBP12.6); with the phosphatases, PP1 and PP2A; and with the regulatory and catalytic subunits of PKA. Furthermore, the inventors have demonstrated that endogenous PKA specifically phosphorylates RyR2 in atrial sarcoplasmic reticulum, resulting in a depletion of calstabin2 (FKBP12.6) in the channel complex. These findings suggest that regulation of contractile function in the atrium could be modulated by PKA phosphorylation of atrial RyR2, in a manner similar to that observed in the ventricular myocardium (Brillantes, et al., Stabilization of calcium release channel (ryanodine receptor) function by FK-506 binding protein, *Cell*, 77:513-523, 1994).

In the current study, the inventors observed that PKA hyperphosphorylation of RyR2 was associated with depletion of calstabin2 (FKBP12.6) in canine AF atria. Similarly, the inventors observed PKA hyperphosphorylation, with associated depletion of calstabin (FKBP12.6), in atrial tissue from humans with AF in the setting of heart failure. The functional consequence of this abnormal PKA hyperphosphorylation of RyR2 was increased open probability at conditions that simulate diastole in the heart (low cytosolic $Ca^{2+}$). Such functional abnormalities are characteristic of channels that have been depleted of calstabin2 (FKBP12.6) (Brillantes, et al., Stabilization of calcium release channel (ryanodine receptor) function by FK-506 binding protein, *Cell*, 77:513-523, 1994). This abnormal channel function in AF is consistent with previous studies demonstrating that the loss of calstabin2 (FKBP12.6) from RyR2, in the setting of PKA hyperphosphorylation, results in "leaky channels" which are predisposed to a diastolic $Ca^{2+}$ leak that is secondary to an increased sensitivity to $Ca^{2+}$-induced $Ca^{2+}$ release (Brillantes et al., Stabilization of calcium release channel (ryanodine receptor) function by FK506-binding protein. *Cell*, 77:513-23, 1994; Kaftan et al., Effects of rapamycin on ryanodine receptor/ $Ca^{2+}$-release channels from cardiac muscle. *Circ. Res.*, 78:990-97, 1996). In the absence of calstabin2 (FKBP12.6), channels are also known to open and close (gate) stochastically, rather than in unison (coupled gating) (Marx et al., Coupled gating between individual skeletal muscle $Ca^{2+}$ release channels (ryanodine receptors). *Science*, 281:818-21, 1998).

Evidence suggests that AF is typically initiated by premature atrial extrasystoles (Bennett and Pentecost, The pattern of onset and spontaneous cessation of atrial fibrillation in man. *Circulation*, 41:981-88, 1970), which are known to result from after-depolarizations (Cranefield, P. F., Action potentials, afterpotentials, and arrhythmias. *Circ. Res.*, 41:415-23, 1977). Reinitiation of AF by atrial extrasystoles, immediately following termination of the arrhythmia, has been observed (Timmermans et al., Immediate reinitiation of atrial fibrillation following internal atrial defibrillation. *J. Cardiovasc. Electrophysiol.*, 9:122-28, 1998; Wellens et al., Atrioverter: an implantable device for the treatment of atrial fibrillation. *Circulation*, 98:1651-56, 1998), and has been specifically linked to early after-depolarizations (Burashnikov and Antzelevitch, Reinduction of atrial fibrillation immediately after termination of the arrhythmia is mediated by late phase 3 early afterdepolarization-induced triggered activity. *Circulation*, 107:2355-60, 2003). Extrasystoles are particularly likely to give rise to AF in the setting of a shortened atrial effective refractory period (Wang et al., Regional and functional factors determining induction and maintenance of atrial fibrillation in dogs. *Am. J. Physiol.*, 271:H148-58, 1996), similar to that which accompanies atrial electrical remodeling.

As discussed above, there is evidence that the aberrant diastolic $Ca^{2+}$ release from "leaky" PKA-hyperphosphorylated RyR2 results in delayed after-depolarizations (DADs) sufficient to trigger lethal ventricular arrhythmias (Wehrens et al., FKBP12.6 deficiency and defective calcium release channel (ryanodine receptor) function linked to exercise-induced sudden cardiac death. *Cell*, 113:829-40, 2003). It is believed that dysfunctional RyR2 calcium handling may also serve to initiate AF in a similar manner. The abnormal channel function observed by the inventors may contribute to the pathogenesis of AF by providing a source of DADs necessary for triggering AF, in addition to contributing to the dysfunctional calcium handling that is integral to the remodeling process associated with the arrhythmia. Given the evidence presented herein that atrial myocardium from humans with AF, in the setting of heart failure, is PKA-hyperphosphorylated and depleted of calstabin2 (FKBP12.6), dysfunctional RyR2 function may explain, in part, the frequency of atrial arrhythmias in AF patients.

JTV-519's ability to repair a specific molecular-level defect in RyR2 calcium handling makes it an intriguing candidate for a novel therapeutic agent. JTV-519's potential is underscored by the growing number of important cardiac diseases, including heart failure and fatal ventricular arrhythmias, that involve dysfunctional regulation of RyR2 (i.e., PKA hyperphosphorylation and loss of calstabin2 (FKBP12.6) from the channel complex may be important contributors to their pathogenesis).

Initial studies of JTV-519 focused on its anti-ischemic properties (Personal Communication, Aetas). More recently, however, JTV-519 has been shown to inhibit induction of AF in a canine sterile pericarditis model of atrial fibrillation (Kumagai et al., Antiarrhythmic effects of JTV-519, a novel cardioprotective drug, on atrial fibrillation/flutter in a canine sterile pericarditis model. *J. Cardiovasc. Electrophysiol.,* 14:880-84, 2003). This study did not, however, define the mechanism through which JTV-519 impacted the inducibility and maintenance of AF.

As demonstrated herein, the inventors have determined that treatment with JTV-519 (1 μM) allows recombinant calstabin2 (FKBP12.6) to bind to PKA-phosphorylated RyR2 that has been isolated from normal canine myocardium in vitro. Association of calstabin2 (FKBP12.6) with PKA-phosphorylated RyR2 did not occur with untreated channels. Re-association of calstabin2 (FKBP12.6) with the channel complex restores normal function in PKA-hyperphosphorylated channels. Thus, restoration of RyR2-channel function may play a role in the ability of JTV-519 to inhibit the inducibility and maintenance of AF, as observed by Kumagai et al. (Antiarrhythmic effects of JTV-519, a novel cardioprotective drug, on atrial fibrillation/flutter in a canine sterile pericarditis model. *J. Cardiovasc. Electrophysiol.,* 14:880-84, 2003).

Atrial fibrillation is a complex electrophysiological process; its molecular pathogenesis is likely to be multifactorial. Aberrant myocardial $Ca^{2+}$ handling appears to contribute significantly to the disease process. The inventors' studies suggest that abnormal intracellular-$Ca^{2+}$-release channel function, which results from PKA hyperphosphorylation of RyR2, may contribute to the remodeling process in AF, and could potentially serve as a trigger for arrhythmia.

Novel Methods of Treatment and Prevention Using JTV-519

In accordance with the foregoing, the present invention provides a method for limiting or preventing a decrease in the level of RyR2-bound FKBP12.6 in a subject. As used herein, "FKBP12.6" includes both an "FKBP12.6 protein" and an "FKBP12.6 analogue". Unless otherwise indicated herein, "protein" shall include a protein, protein domain, polypeptide, or peptide, and any fragment thereof. An "FKBP12.6 analogue" is a functional variant of the FKBP12.6 protein, having FKBP12.6 biological activity, that has 60% or greater amino-acid-sequence homology with the FKBP12.6 protein. As further used herein, the term "FKBP12.6 biological activity" refers to the activity of a protein or peptide that demonstrates an ability to associate physically with, or bind with, unphosphorylated or non-hyperphosphorylated RyR2 (i.e., binding of approximately two fold, or, more preferably, approximately five fold, above the background binding of a negative control), under the conditions of the assays described herein, although affinity may be different from that of FKBP12.6.

In addition, as used herein, "RyR2" includes both an "RyR2 protein" (e.g., atrial RyR2 protein or ventricular RyR2 protein) and an "RyR2 analogue". An "RyR2 analogue" is a functional variant of the RyR2 protein, having RyR2 biological activity, that has 60% or greater amino-acid-sequence homology with the RyR2 protein. As used herein, the term "RyR2 analogue" includes RyR1—the skeletal-muscle isoform of RyR2—and RyR3. The RyR2 of the present invention may be unphosphorylated, phosphorylated (e.g., by PKA), or hyperphosphorylated (e.g., by PKA); preferably, the RyR2 is phosphorylated or hyperphosphorylated. As further used herein, the term "RyR2 biological activity" refers to the activity of a protein or peptide that demonstrates an ability to associate physically with, or bind with, FKBP12.6 (i.e., binding of approximately two fold, or, more preferably, approximately five fold, above the background binding of a negative control), under the conditions of the assays described herein, although affinity may be different from that of RyR2.

As described above, the cardiac ryanodine receptor, RyR2, is a protein complex comprising four 565,000-dalton RyR2 proteins in association with four 12,000-dalton FKBP12.6 proteins. FK506 binding proteins (FKBPs) are cis-trans peptidyl-prolyl isomerases that are widely expressed, and serve a variety of cellular functions. FKBP12.6 protein is tightly bound to, and regulates the function of, RyR2. FKBP12.6 binds to the RyR2 channel, one molecule per RyR2 subunit, stabilizes RyR2-channel function, and facilitates coupled gating between neighboring RyR2 channels, thereby preventing aberrant activation of the channel during the resting phase of the cardiac cycle. Accordingly, as used herein, the term "RyR2-bound FKBP12.6" includes a molecule of an FKBP12.6 protein that is bound to an RyR2 protein subunit or a tetramer of FKBP12.6 that is in association with a tetramer of RyR2. The term "RyR2-bound FKBP12.6" also includes an RyR2 protein subunit that is bound to a molecule of an FKBP12.6 protein, or a tetramer of RyR2 that is in association with a tetramer of FKBP12.6. Thus, "a decrease in the level of RyR2-bound FKBP12.6 in a subject" includes a decrease in the level of FKBP12.6-bound RyR2 in a subject, and a decrease in the level of a FKBP12.6-RyR2 complex in a subject.

In accordance with the method of the present invention, a "decrease" in the level of RyR2-bound FKBP12.6 in a subject refers to a detectable decrease, diminution, or reduction in the level of RyR2-bound FKBP12.6 in the subject. Such a decrease is limited or prevented in the subject when the decrease is in any way halted, hindered, impeded, obstructed, or reduced by the administration of JTV-519 (as described below), such that the level of RyR2-bound FKBP12.6 in the subject is higher than it would otherwise be in the absence of JTV-519. The "level" of RyR2-bound FKBP12.6 in a subject refers to the overall level in the subject, including the level of RyR2-bound FKBP12.6 in the blood (circulation), tissues, and cells (e.g., cytoplasm or nucleus) of the subject. By way of example, then, a decrease in the overall level of RyR2-bound FKBP12.6 in the subject may be accomplished by a decrease in the level of RyR2-bound FKBP12.6 in the blood, in a tissue, and/or in cells of the subject.

The level of RyR2-bound FKBP12.6 in a subject may be detected by standard assays and techniques, including those readily determined from the known art (e.g., immunological techniques, hybridization analysis, immunoprecipitation, Western-blot analysis, fluorescence imaging techniques, and/or radiation detection, etc.), as well as any assays and detection methods disclosed herein. For example, protein may be isolated and purified from cells of a subject using standard methods known in the art, including, without limitation, extraction from the cells (e.g., with a detergent that solubilizes the protein) where necessary, followed by affinity purification on a column, chromatography (e.g., FTLC and HPLC), immunoprecipitation (with an antibody), and precipitation (e.g., with isopropanol and a reagent such as Trizol). Isolation and purification of the protein may be followed by electrophoresis (e.g., on an SDS-polyacrylamide gel). A decrease in the level of RyR2-bound FKBP12.6 in a subject, or the limiting or prevention thereof, may be determined by comparing the amount of RyR2-bound FKBP12.6 detected prior to the administration of a therapeutic/preventive agent (e.g., JTV-519 or another 1,4-benzothiazepine derivative, in accordance with methods described below) with the amount detected a suitable time after administration of the therapeutic/preventive agent.

In the method of the present invention, a decrease in the level of RyR2-bound FKBP12.6 in a subject (e.g., in cells of the subject) may be limited or prevented, for example, by inhibiting dissociation of FKBP12.6 and RyR2 in the subject; by increasing binding between FKBP12.6 and RyR2 in the subject; or by stabilizing the RyR2-FKBP12.6 complex in the subject. As used herein, the term "inhibiting dissociation" includes blocking, decreasing, inhibiting, limiting, or preventing the physical dissociation or separation of an FKBP12.6 subunit from an RyR2 molecule in the subject, and blocking, decreasing, inhibiting, limiting, or preventing the physical dissociation or separation of an RyR2 molecule from an FKBP12.6 subunit in the subject. As further used herein, the term "increasing binding" includes enhancing, increasing, or improving the ability of phosphorylated RyR2 to associate physically with FKBP12.6 (e.g., binding of approximately two fold, or, more preferably, approximately five fold, above the background binding of a negative control) in the subject, and enhancing, increasing, or improving the ability of FKBP12.6 to associate physically with phosphorylated RyR2 (e.g., binding of approximately two fold, or, more preferably, approximately five fold, above the background binding of a negative control) in the subject.

Additionally, in the method of the present invention, a decrease in the level of RyR2-bound FKBP12.6 in a subject (e.g., in cells of a subject) may be limited or prevented by directly decreasing the level of phosphorylated RyR2 in the subject, or by indirectly decreasing the level of phosphorylated RyR2 in the subject (e.g., by targeting an enzyme (such as PKA) or another endogenous molecule that regulates or modulates the functions or levels of phosphorylated RyR2 in the cells). Preferably, the level of phosphorylated RyR2 in the subject is decreased by at least 10% in the method of the present invention. More preferably, the level of phosphorylated RyR2 is decreased by at least 20%.

In accordance with the method of the present invention, a decrease in the level of RyR2-bound FKBP12.6 is limited or prevented in a subject (e.g., in cells of a subject). The subject of the present invention may be any animal, including amphibians, birds, fish, mammals, and marsupials, but is preferably a mammal (e.g., a human; a domestic animal, such as a cat, dog, monkey, mouse, or rat; or a commercial animal, such as a cow or pig). In certain embodiments of the present invention, the subject has, or is a candidate for, a cardiac condition. Examples of a "cardiac condition" include, without limitation, cardiac arrhythmias (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, and exercise-induced sudden cardiac death.

Cardiac arrhythmia is a disturbance of the electrical activity of the heart that manifests as an abnormality in heart rate or heart rhythm. Tachycardia (e.g., atrial, junctional (nodal), ventricular, and paroxysmal tachycardia) is a condition associated with excessive rapidity in the action of the heart, particularly when the heart rate is above 100 per min. A tachyarrhythmia is a tachycardia associated with an irregularity in the normal heart rhythm. Exercise-induced cardiac arrhythmia is a heart condition (e.g., a ventricular fibrillation or ventricular tachycardia, including any that leads to sudden cardiac death) that develops during/after a subject has undergone physical exercise.

Atrial fibrillation is an example of tachyarrhythmia. More specifically, atrial fibrillation is a condition associated with an abnormal and irregular heart rhythm, wherein electrical signals are generated chaotically throughout the upper chambers, or atria, of the heart. Common symptoms of atrial fibrillation include, without limitation, palpitations (an uncomfortable awareness of the heart's rapid and irregular beat). Atrial fibrillation can also result in blood clots that travel from the heart to the brain, causing stroke. Current treatment of atrial fibrillation involves control of risk factors, administration of medications to slow the heart rate and/or convert the heart to normal rhythm, and prevention of complications associated with blood clotting.

Heart failure is a condition manifested by decreased contractile function (contractility) of the heart. Symptoms of heart failure include shortness of breath, decreased exercise tolerance, and early muscle fatigue.

A "candidate" for a cardiac condition (e.g., cardiac arrhythmia or heart failure) is a subject who is known to be, or is believed to be, or is suspected of being, at risk for developing a cardiac condition. Examples of candidates for a cardiac condition include, without limitation, an animal/person suspected of having cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia) and/or heart failure; and an animal/person who is known to be, or is believed to be, or is suspected of being, at risk for developing cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, and/or exercise-induced sudden cardiac death.

A "candidate" for exercise-induced cardiac arrhythmia is a subject who is known to be, or is believed to be, or is suspected of being, at risk for developing cardiac arrhythmia during/after physical exercise. Examples of candidates for exercise-induced cardiac arrhythmia include, without limitation, an animal/person known to have catecholaminergic polymorphic ventricular tachycardia (CPVT); an animal/person suspected of having CPVT; and an animal/person who is known to be, or is believed to be, or is suspected of being, at risk for developing cardiac arrhythmia during/after physical exercise, and who is about to exercise, is currently exercising, or has just completed exercise. As discussed above, CPVT is an inherited disorder in individuals with structurally-normal hearts. It is characterized by stress-induced ventricular tachycardia—a lethal arrhythmia that may cause sudden cardiac death. In subjects with CPVT, physical exertion and/or stress induce bidirectional and/or polymorphic ventricular tachycardias that lead to sudden cardiac death (SCD) in the absence of detectable structural heart disease. Individuals with CPVT have ventricular arrhythmias when subjected to exercise, but do not develop arrhythmias at rest.

In the method of the present invention, the cells of a subject are preferably striated muscle cells. A striated muscle is a muscle in which the repeating units (sarcomeres) of the contractile myofibrils are arranged in registry throughout the cell, resulting in transverse or oblique striations that may be observed at the level of a light microscope. Examples of striated muscle cells include, without limitation, voluntary (skeletal) muscle cells and cardiac muscle cells. In a preferred embodiment, the cell used in the method of the present invention is a human cardiac muscle cell. As used herein, the term "cardiac muscle cell" includes cardiac muscle fibers, such as those found in the myocardium of the heart. Cardiac muscle fibers are composed of chains of contiguous heart-muscle cells, or cardiomyocytes, joined end to end at intercalated disks. These disks possess two kinds of cell junctions: expanded desmosomes extending along their transverse portions, and gap junctions, the largest of which lie along their longitudinal portions.

In the method of the present invention, a decrease in the level of RyR2-bound FKBP12.6 is limited or prevented in a subject (e.g., in cells of a subject) by administering JTV-519 to the subject; this would then permit contact between cells of the subject and JTV-519. JTV-519 (4-[3-(4-benzylpiperidin-1-yl)propionyl]-7-methoxy-2,3,4,5-tetrahydro-1,4-benzothiazepine monohydrochloride), also known as k201, is a derivative of 1,4-benzothiazepine, and a modulator of calcium-ion channels. In addition to regulating $Ca^{2+}$ levels in myocardial cells, JTV-519 modulates the $Na^+$ current and the inward-rectifier $K^+$ current in guinea pig ventricular cells, and inhibits the delayed-rectifier $K^+$ current in guinea pig atrial cells. FK506 and rapamycin are drugs that may be used to design other compounds that stabilize the RyR2-FKBP12.6 complex in the subject of the present invention. FK506 and rapamycin both dissociate FKBP12.6 from RyR2. It is possible to design and/or screen for compounds that are structurally related to these drugs, but have the opposite effects.

In the method of the present invention, JTV-519 may be administered to a subject by way of a therapeutic composition, comprising JTV-519 and a pharmaceutically-acceptable carrier. The pharmaceutically-acceptable carrier must be "acceptable" in the sense of being compatible with the other ingredients of the composition, and not deleterious to the recipient thereof. The pharmaceutically-acceptable carrier employed herein is selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

The pharmaceutical formulations of the present invention may be prepared by methods well-known in the pharmaceutical arts. For example, the JTV-519 may be brought into association with a carrier or diluent, as a suspension or solution. Optionally, one or more accessory ingredients (e.g., buffers, flavoring agents, surface active agents, and the like) also may be added. The choice of carrier will depend upon the route of administration.

JTV-519 may be administered to a subject by contacting target cells (e.g., cardiac muscle cells) in vivo in the subject with the JTV-519. JTV-519 may be contacted with (e.g., introduced into) cells of the subject using known techniques utilized for the introduction and administration of proteins, nucleic acids, and other drugs. Examples of methods for contacting the cells with (i.e., treating the cells with) JTV-519 include, without limitation, absorption, electroporation, immersion, injection, introduction, liposome delivery, transfection, transfusion, vectors, and other drug-delivery vehicles and methods. When the target cells are localized to a particular portion of a subject, it may be desirable to introduce the JTV-519 directly to the cells, by injection or by some other means (e.g., by introducing the JTV-519 into the blood or another body fluid). The target cells may, for example, be contained in heart tissue of a subject, and may be detected in heart tissue of the subject by standard detection methods readily determined from the known art, examples of which include, without limitation, immunological techniques (e.g., immunohistochemical staining), fluorescence imaging techniques, and microscopic techniques.

Additionally, the JTV-519 of the present invention may be administered to a human or animal subject by known procedures, including, without limitation, oral administration, parenteral administration, and transdermal administration. Preferably, the JTV-519 is administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual injection, or by way of catheter. In one embodiment, the agent is administered to the subject by way of targeted delivery to cardiac muscle cells via a catheter inserted into the subject's heart.

For oral administration, a JTV-519 formulation may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration (i.e., administration by injection through a route other than the alimentary canal), JTV-519 may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual, or by way of catheter into the subject's heart.

For transdermal administration, JTV-519 may be combined with skin penetration enhancers, such as propylene glycol, polyethylene glycol, isopropanol, ethanol, oleic acid, N-methylpyrrolidone, and the like, which increase the permeability of the skin to the JTV-519, and permit the JTV-519 to penetrate through the skin and into the bloodstream. The JTV-519/enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in a solvent, such as methylene chloride, evaporated to the desired viscosity, and then applied to backing material to provide a patch.

In accordance with the method of the present invention, JTV-519 may be administered to the subject (and JTV-519 may be contacted with cells of the subject) in an amount effective to limit or prevent a decrease in the level of RyR2-bound FKBP12.6 in the subject, particularly in cells of the subject. This amount may be readily determined by the skilled artisan, based upon known procedures, including analysis of titration curves established in vivo, and methods and assays disclosed herein. A suitable amount of JTV-519 effective to limit or prevent a decrease in the level of RyR2-bound FKBP12.6 in the subject may range from about 5 mg/kg/day to about 20 mg/kg/day, and/or may be an amount sufficient to achieve plasma levels ranging from about 300 ng/ml to about 1000 ng/ml. Preferably, the amount of JTV-519 ranges from about 10 mg/kg/day to about 20 mg/kg/day.

In one embodiment of the present invention, the subject has not yet developed a cardiac condition, such as a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death. In this case, the amount of JTV-519 effective to limit or prevent a decrease in the level of RyR2-bound FKBP12.6 in the subject may be an amount of JTV-519 effective to prevent a cardiac condition (e.g., cardiac arrhythmia, heart failure, or exercise-induced sudden cardiac death) in the subject.

As used herein, an amount of a drug (e.g., JTV-519) "effective to prevent a cardiac condition" includes an amount of the drug (e.g., JTV-519) effective to prevent the development of the clinical impairment or symptoms of the cardiac condition. For example, where the cardiac condition is atrial fibrillation, the amount of JTV-519 effective to prevent atrial fibrillation may be an amount of JTV-519 effective to prevent palpitations and/or blood clots in the subject. Similarly, where the cardiac condition is exercise-induced cardiac arrhythmia, the amount of JTV-519 effective to prevent exercise-induced cardiac arrhythmia may be an amount of JTV-519 effective to prevent exercise-induced palpitations, fainting, ventricular fibrillation, ventricular tachycardia, and sudden cardiac death in the subject. Additionally, where the cardiac condition is heart failure, the amount of JTV-519 effective to prevent heart failure may be an amount of JTV-519 effective to prevent shortness of breath, decreased exercise tolerance, and early muscle fatigue in the subject.

The amount of a drug (e.g., JTV-519) effective to prevent a cardiac condition in a subject will vary depending upon the particular factors of each case, including the type of cardiac condition, the subject's weight, the severity of the subject's condition, and the mode of administration of the drug (e.g., JTV-519). This amount may be readily determined by the skilled artisan, based upon known procedures, including clinical trials, and methods disclosed herein. In one embodiment of the present invention, the amount of a drug (e.g., JTV-519) effective to prevent exercise-induced cardiac arrhythmia is an amount of a drug (e.g., JTV-519) effective to prevent exercise-induced sudden cardiac death in the subject. In another embodiment, the drug (e.g., JTV-519) prevents at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in the subject.

Because of its ability to stabilize RyR2-bound FKBP12.6, and maintain and restore balance in the context of dynamic PKA phosphorylation and dephosphorylation of RyR2, JTV-519 may also be useful in treating a subject who has already started to experience clinical symptoms of a cardiac condition. If the symptoms of the cardiac condition are observed in the subject early enough, JTV-519 might be effective in limiting or preventing a further decrease in the level of RyR2-bound FKBP12.6 in the subject.

Accordingly, in another embodiment of the present invention, the subject has developed a cardiac condition. For example, the subject has been exercising, or is currently exercising, and has developed exercise-induced cardiac arrhythmia. In such a case, the amount of JTV-519 effective to limit or prevent a decrease in the level of RyR2-bound FKBP12.6 in the subject may be an amount of JTV-519 effective to treat a cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia) or heart failure) in the subject.

As used herein, an amount of a drug (e.g., JTV-519) "effective to treat a cardiac condition" includes an amount of a drug (e.g., JTV-519) effective to alleviate or ameliorate the clinical impairment or symptoms of the cardiac condition. For example, where the cardiac condition is atrial fibrillation, the amount of JTV-519 effective to treat atrial fibrillation may be an amount of JTV-519 effective to alleviate or ameliorate palpitations and/or blood clots in the subject. Similarly, where the cardiac condition is exercise-induced cardiac arrhythmia, the amount of JTV-519 effective to treat exercise-induced cardiac arrhythmia may be an amount of JTV-519 effective to alleviate or ameliorate exercise-induced palpitations, fainting, ventricular fibrillation, and ventricular tachycardia in the subject. Additionally, where the cardiac condition is heart failure, the amount of JTV-519 effective to treat heart failure may be an amount of JTV-519 effective to alleviate or ameliorate shortness of breath, decreased exercise tolerance, and early muscle fatigue in the subject.

The amount of a drug (e.g., JTV-519) effective to treat a cardiac condition in a subject will vary depending upon the particular factors of each case, including the type of cardiac condition, the subject's weight, the severity of the subject's condition, and the mode of administration of the drug (e.g., JTV-519). This amount may be readily determined by the skilled artisan, based upon known procedures, including clinical trials, and methods disclosed herein. In a preferred embodiment, the drug (e.g., JTV-519) treats at least one cardiac condition in the subject.

The present invention further provides a method for treating at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia) or heart failure) in a subject. The method comprises administering JTV-519 to the subject in an amount effective to treat at least one cardiac condition in the subject. A suitable amount of JTV-519 effective to treat a cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia) or heart failure) in a subject may range from about 5 mg/kg/day to about 20 mg/kg/day, and/or may be an amount sufficient to achieve plasma levels ranging from about 300 ng/ml to about 1000 ng/ml.

The present invention also provides a method for preventing at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in a subject. The method comprises administering JTV-519 to the subject in an amount effective to prevent at least one cardiac condition in the subject. A suitable amount of JTV-519 effective to prevent at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in a subject may range from about 5 mg/kg/day to about 20 mg/kg/day, and/or may be an amount sufficient to achieve plasma levels ranging from about 300 ng/ml to about 1000 ng/ml.

In various embodiments of the above-described methods, the exercise-induced cardiac arrhythmia in the subject is associated with VT. In preferred embodiments, the VT is CPVT. In other embodiments of these methods, the subject is a candidate for exercise-induced cardiac arrhythmia, including a candidate for exercise-induced sudden cardiac death.

Additionally, in view of the foregoing methods, the present invention also provides use of JTV-519 in a method for limiting or preventing a decrease in the level of RyR2-bound FKBP12.6 in a subject who has, or is a candidate for, at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death). The present invention also provides use of JTV-519 in a method for treating or preventing at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in a subject.

Novel Methods of Screening

As discussed above and presented herein, the inventors' data show that protein kinase A (PKA) phosphorylation of the cardiac ryanodine receptor, RyR2, on serine 2809 activates the channel by releasing the FK506 binding protein, FKBP12.6. In failing hearts (including human hearts and animal models of heart failure), RyR2 is PKA-hyperphosphorylated, resulting in defective channels that have decreased amounts of bound FKBP12.6, and have increased sensitivity to calcium-induced activation. The net result of these changes is that the RyR2 channels are "leaky". These channel leaks can result in a depletion of intracellular stores of calcium to such an extent that there is no longer enough calcium in the sarcoplasmic reticulum (SR) to provide a strong stimulus for muscle contraction. This results in weak contraction of heart muscle. As a second consequence of the channel leaks, RyR2 channels release calcium during the resting phase of the heart cycle known as "diastole". This release of calcium during diastole can trigger the fatal arrhythmias of the hearts (e.g., ventricular tachycardia and ventricular fibrillation) that cause sudden cardiac death (SCD).

The inventors have also shown that treatment of heart failure with a mechanical pumping device, referred to as a left ventricular assist device (LVAD), which puts the heart at rest and restores normalized function, is associated with a reduction in the PKA hyperphosphorylation of RyR2, and normalized function of the channel. Furthermore, the inventors have shown that treatment of dogs (who have pacing-induced heart failure) with beta-adrenergic blockers (beta blockers) reverses the PKA hyperphosphorylation of RyR2. Beta blockers inhibit the pathway that activates PKA. The conclusion which may be drawn from the results of the inventors' work is that PKA phosphorylation of RyR2 increases the activity of the channel, resulting in the release of more calcium into the cell for a given trigger (activator) of the channel.

As further disclosed herein, the inventors have established that cardiac conditions (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) are associated with an increase in phosphorylation of RyR2 proteins (particularly CPVT-associated RyR2 mutant proteins) and a decrease in the level of RyR2-bound FKBP12.6. It is possible to use this mechanism to design effective drugs for treating and preventing such cardiac conditions. A candidate agent having the ability to limit or prevent a decrease in the level of RyR2-bound FKBP12.6 may, as a consequence of this limiting or preventive activity, have an effect on an RyR2-associated biological event, thereby treating or preventing such cardiac conditions.

Accordingly, the present invention further provides a method for identifying an agent for use in treating or preventing at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death). The method comprises the steps of: (a) obtaining or generating a culture of cells containing RyR2; (b) contacting the cells with a candidate agent; (c) exposing the cells to one or more conditions known to increase phosphorylation of RyR2 in cells; and (d) determining if the agent limits or prevents a decrease in the level of RyR2-bound FKBP12.6 in the cells.

As used herein, an "agent" shall include a protein, polypeptide, peptide, nucleic acid (including DNA or RNA), antibody, Fab fragment, F(ab')$_2$ fragment, molecule, compound, antibiotic, drug, and any combination(s) thereof. An agent that limits or prevents a decrease in the level of RyR2-bound FKBP12.6 may be either natural or synthetic, and may be an agent reactive with (i.e., an agent that has affinity for, binds to, or is directed against) RyR2 and/or FKBP12.6. As further used herein, a cell "containing RyR2" is a cell (preferably, a cardiac muscle cell) in which RyR2, or a derivative or homologue thereof, is naturally expressed or naturally occurs. Conditions known to increase phosphorylation of RyR2 in cells include, without limitation, PKA.

In the method of the present invention, cells may be contacted with a candidate agent by any of the standard methods of effecting contact between drugs/agents and cells, including any modes of introduction and administration described herein. The level of RyR2-bound FKBP12.6 in the cell may be measured or detected by known procedures, including any of the methods, molecular procedures, and assays known to one of skill in the art or described herein. In one embodiment of the present invention, the agent limits or prevents a decrease in the level of RyR2-bound FKBP12.6 in the cells.

As disclosed herein, RyR2 has been implicated in a number of biological events in striated muscle cells. For example, it has been shown that RyR2 channels play an important role in EC coupling and contractility in cardiac muscle cells. Therefore, it is clear that therapeutic or preventive drugs designed to limit or prevent a decrease in the level of RyR2-bound FKBP12.6 in cells, particularly cardiac muscle cells, may be useful in the regulation of a number of RyR2-associated biological events, including EC coupling and contractility. Thus, once the candidate agent of the present invention has been screened, and has been determined to have a suitable limiting or preventive effect on decreasing levels of RyR2-bound FKBP12.6, it may be evaluated for its effect on EC coupling and contractility in cells, particularly cardiac muscle cells. It is expected that the therapeutic/preventive agent of the present invention will be useful for treating or preventing cardiac conditions, including cardiac arrhythmias (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, and exercise-induced sudden cardiac death.

Accordingly, the method of the present invention may further comprise the steps of: (e) contacting the candidate agent with a culture of cells containing RyR2; and (f) determining if the agent has an effect on an RyR2-associated biological event in the cells. As used herein, an "RyR2-associated biological event" includes a biochemical or physiological process in which RyR2 levels or activity have been implicated. As disclosed herein, examples of RyR2-associated biological events include, without limitation, EC coupling and contractility in cardiac muscle cells. According to this method of the present invention, a candidate agent may be contacted with one or more cells (preferably, cardiac muscle cells) in vitro. For example, a culture of the cells may be incubated with a preparation containing the candidate agent. The candidate agent's effect on an RyR2-associated biological event then may be assessed by any biological assays or methods known in the art, including immunoblotting, single-channel recordings and any others disclosed herein.

The present invention is further directed to an agent identified by the above-described identification method, as well as a pharmaceutical composition comprising the agent and a pharmaceutically-acceptable carrier. The agent may be useful for preventing exercise-induced sudden cardiac death in a subject, and for treating or preventing other RyR2-associated conditions. As used herein, an "RyR2-associated condition" is a condition, disease, or disorder in which RyR2 level or activity has been implicated, and includes an RyR2-associated biological event and a cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death).

The RyR2-associated condition may be treated or prevented in the subject by administering to the subject an amount of the agent effective to treat or prevent the RyR2-associated condition in the subject. This amount may be readily determined by one skilled in the art. In one embodiment, the present invention provides a method for treating or preventing at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in a subject, by administering the agent to the subject in an amount effective to treat or prevent at least one cardiac condition in the subject.

The present invention also provides an in vivo method for identifying an agent for use in treating or preventing a cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death). The method comprises the steps of: (a) obtaining or generating an animal containing RyR2; (b) administering a candidate agent to the animal; (c) exposing the animal to one or more conditions known to increase phosphorylation of RyR2 in cells; and (d) determining if the agent limits or prevents a decrease in the level of RyR2-bound FKBP12.6 in the animal. The method may further comprise the steps of: (e) administering the agent to an animal containing RyR2; and (f) determining if the agent has an effect on an RyR2-associated biological event in the animal. Also provided is an agent identified by this method; a pharmaceutical composition comprising this agent; and a method for treating or preventing at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in a subject, by administering this agent to the subject in an amount effective to treat or prevent at least one cardiac condition in the subject.

The inventors' work has demonstrated that compounds which block PKA activation would be expected to reduce the activation of the RyR2 channel, resulting in less release of calcium into the cell. Compounds that bind to the RyR2 channel at the FKBP12.6 binding site, but do not come off the channel when the channel is phosphorylated by PKA, would also be expected to decrease the activity of the channel in response to PKA activation or other triggers that activate the RyR2 channel. Such compounds would also result in less calcium release into the cell. In view of these findings, the present invention further provides additional assays for identifying agents that may be useful in treating or preventing cardiac conditions (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death), in that they block or inhibit activation of RyR2.

By way of example, the diagnostic assays of the present invention may screen for the release of calcium into cells via the RyR2 channel, using calcium-sensitive fluorescent dyes (e.g., Fluo-3, Fura-2, and the like). Cells may be loaded with the fluorescent dye of choice, then stimulated with RyR2 activators to determine whether or not compounds added to the cell reduce the calcium-dependent fluorescent signal (Brillantes et al., Stabilization of calcium release channel (ryanodine receptor) function by FK506-binding protein. *Cell,* 77:513-23, 1994; Gillo et al., Calcium entry during induced differentiation in murine erythroleukemia cells. *Blood,* 81:783-92, 1993; Jayaraman et al., Regulation of the inositol 1,4,5-trisphosphate receptor by tyrosine phosphorylation. *Science,* 272:1492-94, 1996). Calcium-dependent fluorescent signals may be monitored with a photomultiplier tube, and analyzed with appropriate software, as previously described (Brillantes et al., Stabilization of calcium release channel (ryanodine receptor) function by FK506-binding protein. *Cell,* 77:513-23, 1994; Gillo et al., Calcium entry during induced differentiation in murine erythroleukemia cells. *Blood,* 81:783-92, 1993; Jayaraman et al., Regulation of the inositol 1,4,5-trisphosphate receptor by tyrosine phosphorylation. *Science,* 272:1492-94, 1996). This assay can easily be automated to screen large numbers of compounds using multiwell dishes.

To identify compounds that inhibit the PKA-dependent activation of RyR2-mediated intracellular calcium release, an assay may involve the expression of recombinant RyR2 channels in a heterologous expression system, such as Sf9, HEK293, or CHO cells (Brillantes et al., Stabilization of calcium release channel (ryanodine receptor) function by FK506-binding protein. *Cell,* 77:513-23, 1994). RyR2 could also be co-expressed with beta-adrenergic receptors. This would permit assessment of the effect of compounds on RyR2 activation, in response to addition of beta-adrenergic receptor agonists.

The level of PKA phosphorylation of RyR2 which correlates with the degree of heart failure may also be assayed, and then used to determine the efficacy of compounds designed to block the PKA phosphorylation of the RyR2 channel. Such an assay may be based on the use of antibodies that are specific for the RyR2 protein. For example, the RyR2-channel protein may be immunoprecipitated, and then back-phosphorylated with PKA and [gamma$^{32}$P]-ATP. The amount of radioactive [$^{32}$P] label that is transferred to the RyR2 protein may be then measured using a phosphorimager (Marx et al., PKA phosphorylation dissociates FKBP12.6 from the calcium release channel (ryanodine receptor): defective regulation in failing hearts. *Cell,* 101:365-76, 2000).

Another assay of the present invention involves use of a phosphoepitope-specific antibody that detects RyR2 that is PKA phosphorylated on Ser 2809. Immunoblotting with such an antibody can be used to assess efficacy of therapy for heart failure and cardiac arrhythmias. Additionally, RyR2 S2809A and RyR2 S2809D knock-in mice may be used to assess efficacy of therapy for heart failure and cardiac arrhythmias. Such mice further provide evidence that PKA hyperphosphorylation of RyR2 is a contributing factor in heart failure and cardiac arrhythmias, by showing that the RyR2 S2809A mutation inhibits heart failure and arrhythmias, and that the RyR2 S2809D mutation worsens heart failure and arrhythmias.

Novel 1,4-Benzothiazepine Derivatives and Methods of Synthesizing Same 1,4-benzothiazepine derivatives, particularly 2,3,4,5-tetrahydro-1,4-benzothiazepine derivatives, are important building blocks in the preparation of biologically-active molecules, including JTV-519. The inventors have developed a novel process for preparing 1,4-benzothiazepine intermediate compounds, such as 7-methoxy-2,3,4,5-tetrahydro-1,4-benzothiazepine. The inventors process utilizes readily-available and inexpensive starting materials, and provides high yields of key 1,4-benzothiazepine intermediates.

In the early 1990s, Kaneko et al. (U.S. Pat. No. 5,416,066; WO 92/12148; JP4230681) disclosed that JTV-519 could be prepared by reacting 7-methoxy-2,3,4,5-tetrahydro-1,4-benzothiazepine (a 1,4-benzothiazepine intermediate) with acryloyl chloride, and then reacting the resulting product with 4-benzyl piperidine.

Two processes for the preparation of 7-methoxy-2,3,4,5-tetrahydro-1,4-benzothiazepine and similar compounds have been previously reported in the literature. The first process, disclosed by Kaneko et al. (U.S. Pat. No. 5,416,066), involved a synthetic route of six steps that started with 2,5-dihydroxybenzoic acid. In this process, 2,5-dihydroxybenzoic acid was selectively methylated with dimethyl sulfate. The resulting compound was then reacted with dimethylthiocarbamoyl chloride for 20 h, and then subjected to high temperature (270° C.) for 9 h. The product of this step was refluxed with sodium methoxide in methanol for 20 h. The product of the reflux step was then reacted with 2-chloroethylamine, under basic conditions and at a high temperature, to produce a cyclized amide. The cyclized amide was reduced with LiAlH$_4$ to yield 7-methoxy-2,3,4,5-tetrahydro-1,4-benzothiazepine (a 1,4-benzothiazepine intermediate).

The second process for the preparation of 7-methoxy-2,3,4,5-tetrahydro-1,4-benzothiazepine was disclosed by Hitoshi in a Japanese patent (JP 10045706). This process started with 2-bromo-5-methoxy benzaldehyde. The bromide was substituted with NaSMe, and the resulting product was oxidized with chlorine, followed by reflux in water, to yield disulfide dialdehyde. The dialdehyde was treated with 2-chloroethylamine, and the resulting product was reduced with a reducing agent, such as NaBH$_4$. The resulting compound was cyclized to give 7-methoxy-2,3,4,5-tetrahydro-1,4-benzothiazepine.

Initially, the inventors attempted to prepare the 1,4-benzothiazepine intermediate, 7-methoxy-2,3,4,5-tetrahydro-1,4-benzothiazepine, using the methods described above. However, they found that the first process, described by Kaneko et al. (U.S. Pat. No. 5,416,066), involved synthetic steps of high temperature and long reaction time. Additionally, the inventors discovered that the thio group in the third thiolated intermediate was easily oxidized by air to a disulfide compound, making it impossible to synthesize the subsequent cyclized product. The inventors also determined that the process described by Hitoshi (JP 10045706) involved Cl$_2$, and that another patented method for the preparation of the first intermediate, apart from the substitution of bromide with NaSMe, had to be used.

To overcome the foregoing problems, the inventors developed a novel process for making 7-methoxy-2,3,4,5-tetrahydro-1,4-benzothiazepine from readily-available and inexpensive starting materials. The inventors' process simplifies isolation and purification steps, and can be used to prepare various 1,4-benzothiazepine intermediates, including 7-methoxy-2,3,4,5-tetrahydro-1,4-benzothiazepine and other compounds having the general structure shown in formula:

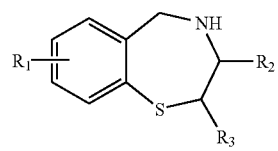

R1 = n-MeO, n-MeS, n-alkyl, n = 6, 7, 8, 9
R2 = alkyl
R3 = alkyl

This process may also be used to prepare JTV-519.

Accordingly, in view of the foregoing, the present invention provides a method for the synthesis of a compound having formula:

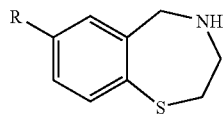

wherein R=OR', SR', NR', alkyl, or halide and R'=alkyl, aryl, or H, and wherein R can be at position 2, 3, 4, or 5, said method comprising the steps of:
(a) treating a compound having formula:

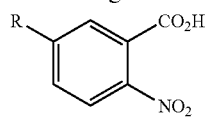

wherein R is as defined above, with a reducing agent, in the presence of an optional catalyst, to form a compound having formula:

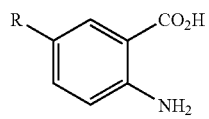

wherein R is as defined above;
(b) treating the compound formed in step (a) with a diazotizing agent and a disulfide, to form a compound having formula:

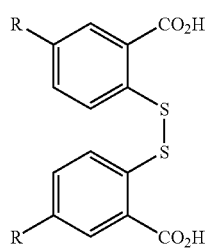

wherein R is as defined above;
(c) treating the compound formed in step (b) with an activating agent and chloroethylamine, to form a compound having formula:

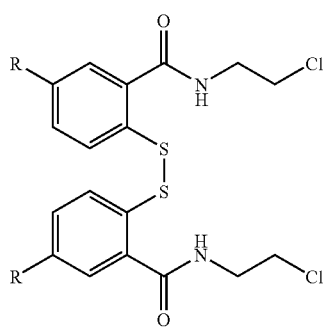

wherein R is as defined above;
(d) treating the compound formed in step (c) with a reducing agent and a base, to form a compound having formula:

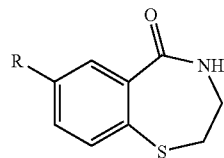

wherein R is as defined above; and
(e) treating the compound formed in step (d) with a reducing agent, to form a compound having formula:

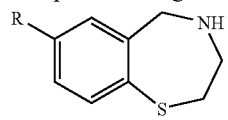

wherein R is as defined above.

In accordance with the method of the present invention, the reducing agent in step (a) may be $H_2$. Additionally, the diazotizing agent in step (b) may be $NaNO_2$, and the disulfide in step (b) may be $Na_2S_2$. Furthermore, the chloride in step (c) may be $SOCl_2$. The reducing agent in step (d) may be trimethylphosphine ($PMe_3$), while the base in step (d) is triethyl amine. In another embodiment, the reducing agent in step (e) is $LiAlH_4$.

The present invention further provides a method for the synthesis of a compound of having formula:

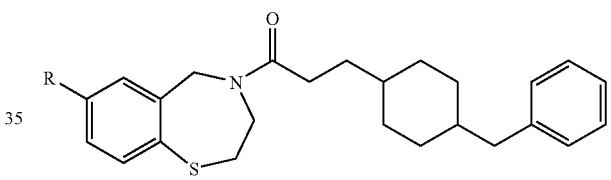

wherein R=OR', SR', NR', alkyl, or halide and R'=alkyl, aryl, or H, and wherein R can be at position 2, 3, 4, or 5, said method comprising the step of:
(a) treating a compound having formula:

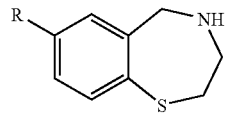

wherein R is as defined above, with 3-bromopropionic chloride and a compound having formula:

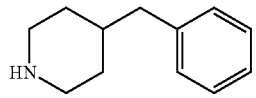

to form a compound having formula:

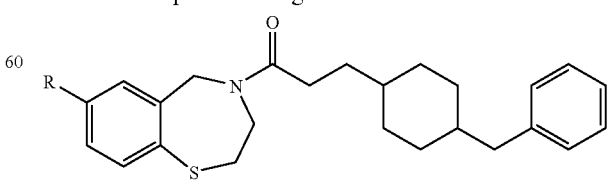

wherein R is as defined above.

By way of example, a compound having the formula:

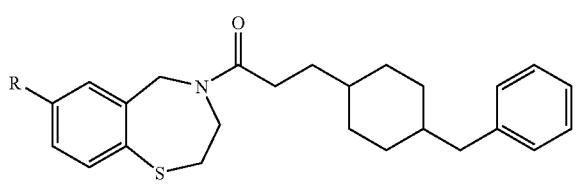

wherein R=OR', SR', NR', alkyl, or halide and R'=alkyl, aryl, or H, and wherein R can be at position 2, 3, 4, or 5, may be synthesized as follows:

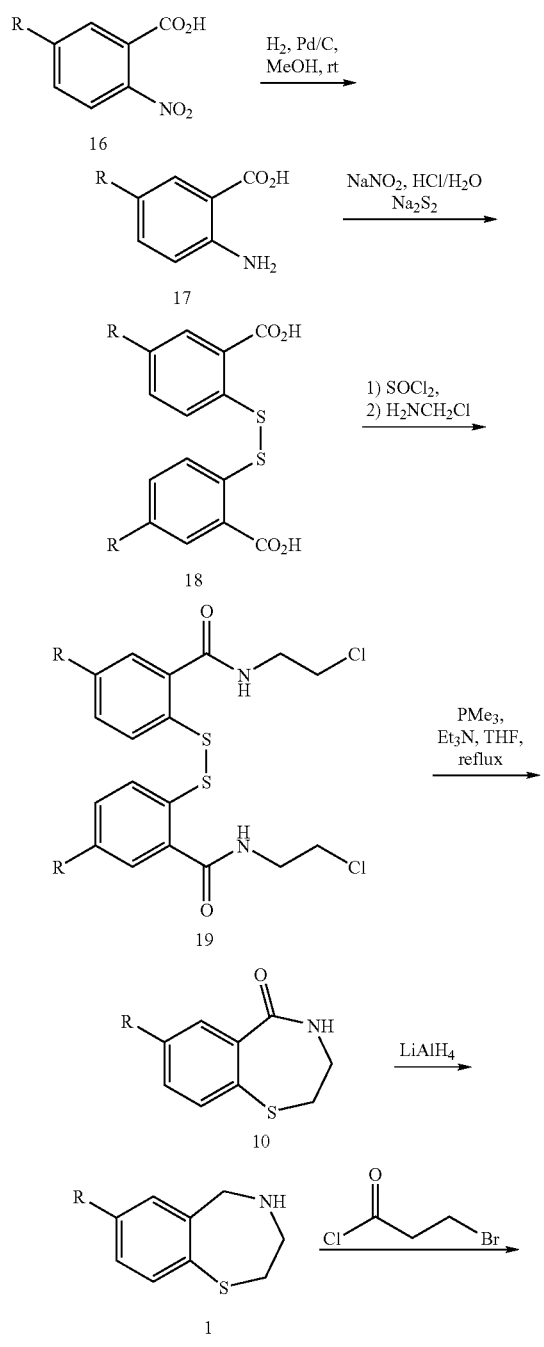

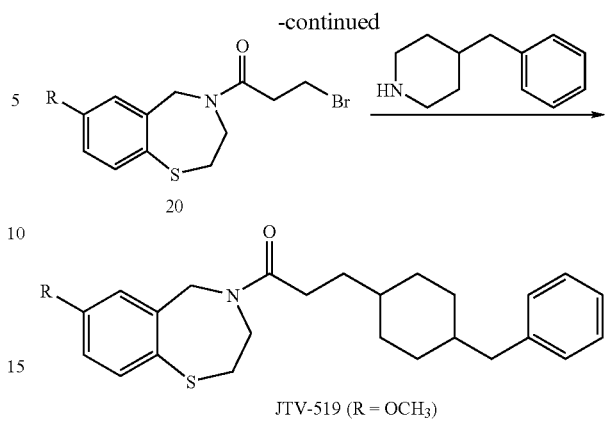

JTV-519 (R = OCH$_3$)

R = OR', SR', NR', alkyl, halides: R' = alkyl, aryl, H
R can be at positions 2, 3, 4, or 5

By way of example, and as shown in Example 9 and Scheme 1 below, 7-methoxy-2,3,4,5-tetrahydro-1,4-benzothiazepine may be prepared from 2-nitro-5-methoxybenzoic acid as follows. The nitro group of 2-nitro-5-methoxybenzoic acid is reduced, using H$_2$ with Pd/C as a catalyst, to give 2-amino-5-methoxybenzoic acid. 2-amino-5-methoxybenzoic acid may be diazotized with NaNO$_2$, and then treated with Na$_2$S$_2$, to provide a stable disulfide compound. Without further purification, the stable disulfide compound may be treated with SOCl$_2$, and then reacted with 2-chloroethylamine, in the presence of Et$_3$N, to give an amide. The amide compound may then be converted to a cyclized compound via a one-pot procedure, as follows. A reducing reagent (such as trimethylphosphine or triphenylphosphine) and a base (such as triethylamine) may be added to a solution of the amide compound in THF (tetrahydrofuran). The resulting reaction mixture may then be refluxed for 3 h. The reducing agent (trimethylphosphine or triphenylphine) cleaves the disulfide (S—S) to its monosulfide (—S), which, in situ, undergoes intramolecular cyclization with the chloride to yield a cyclized amide. The cyclized amide may then be reduced with LiAlH$_4$ to yield the 1,4-benzothiazepine intermediate, 7-methoxy-2,3,4,5-tetrahydro-1,4-benzothiazepine.

JTV-519 may then be prepared from 7-methoxy-2,3,4,5-tetrahydro-1,4-benzothiazepine by reacting the 7-methoxy-2,3,4,5-tetrahydro-1,4-benzothiazepine with 3-bromopropionic chloride, and then reacting the resulting compound with 4-benzyl piperidine.

The present invention further provides a composition, comprising radio-labeled JTV-519. Labeling of JTV-519 may be accomplished using one of a variety of different radioactive labels known in the art. The radioactive label of the present invention may be, for example, a radioisotope. The radioisotope may be any isotope that emits detectable radiation, including, without limitation, $^{35}$S, $^{125}$I, $^{3}$H, or $^{14}$C. Radioactivity emitted by the radioisotope can be detected by techniques well known in the art. For example, gamma emission from the radioisotope may be detected using gamma imaging techniques, particularly scintigraphic imaging.

By way of example, and as shown in Example 10 and Scheme 2 below, radio-labeled JTV-519 may be prepared as follows. JTV-519 may be demethylated at the phenyl ring using BBr$_3$. The resulting phenol compound may then be re-methylated with a radio-labeled methylating agent (such as $^{3}$H-dimethyl sulfate) in the presence of a base (such as NaH) to provide $^{3}$H-labeled JTV-519.

The present invention further provides novel 1,4-benzothiazepine intermediates and derivatives, including 2,3,4,5-tetrahydro-1,4-benzothiazepenes that are similar to JTV-519. By way of example, the present invention provides compounds having the following formulas:

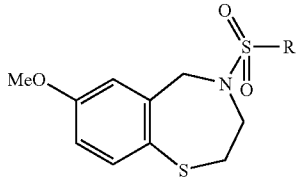

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl;

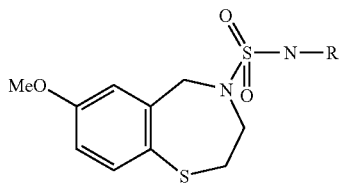

wherein R=aryl, alkyl, —(CH$_2$)$_n$NR'$_2$, or —(CH$_2$)$_n$SR', and n=0, 1, 2, or 3, and R'=alkyl or cycloalkyl;

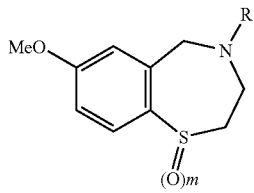

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2; and

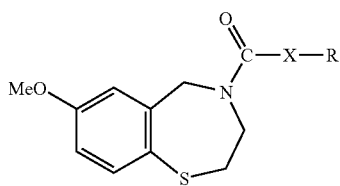

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O. Also provided are additional 2, 3, 4, 5-tetrahydro-1,4-benzothiazepine compounds having the following formulas:

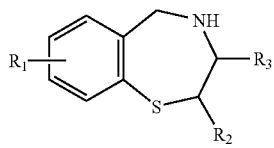

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl;

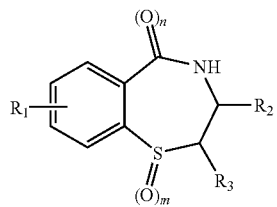

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein m=0, 1, or 2; and wherein n=0 or 1; and

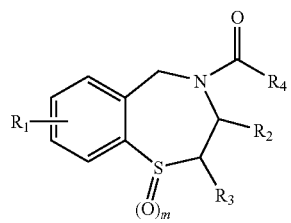

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein R4=H, halide, alkenyl, carboxylic acid, or an alkyl containing O, S, or N; and wherein m=0, 1, or 2.

Examples of the inventors' novel 1,4-benzothiazepine compounds include, without limitation, S7, S-20, S-25, S-27, and S36. Preferably, the compound is S36. Structures for S7, S-20, S-25, S-27, and S36 may be found in Appendix A to the present application. These and any other novel compounds of the present invention may be associated with a pharmaceutically-acceptable carrier, as described above, so as to form a pharmaceutical composition.

The present invention further provides methods of synthesizing the novel 1,4-benzothiazepine compounds disclosed herein. For example, the present invention provides a method for the synthesis of a compound having formula:

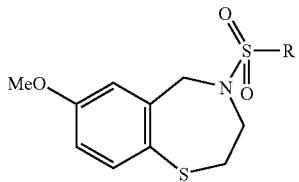

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl, comprising the steps of:

(a) treating a compound having formula:

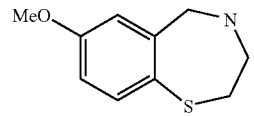

with a sulfonyl chloride compound (including any sulfonyl chloride derivative) and a base, to form a compound having the formula:

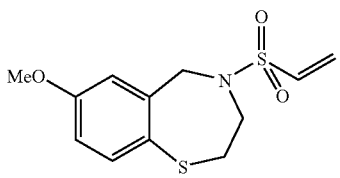

(b) optionally, treating the compound formed in step (a) with a primary or secondary amine, to form a compound having formula:

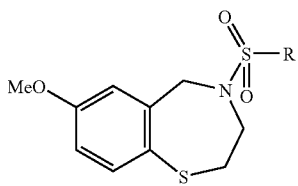

wherein R is as defined above. In one embodiment, the sulfonyl chloride compound in step (a) is selected from the group consisting of alkylsulfonyl chloride and arylsulfonyl chloride. In another embodiment, the base in step (a) is Et₃N. In still another embodiment, the primary or secondary amine in step (b) is 4-benzylpiperidine.

The method of the invention may further comprise the step of oxidizing the compound having formula:

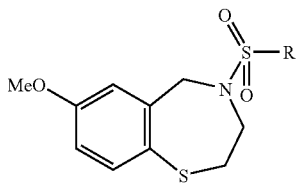

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl, with an oxidizing agent, to form a compound having formula:

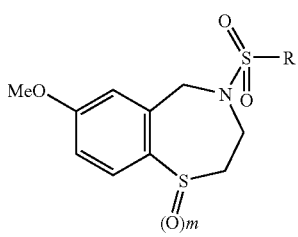

m = 1 or 2 wherein R is as defined above, and wherein m=1 or 2. In one embodiment of the present invention, the oxidizing agent is hydrogen peroxide.

By way of example, and as shown in Example 11 and Scheme 3, the inventors have developed a method of synthesizing compounds having the general structure:

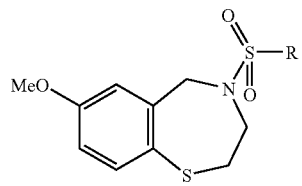

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl. Novel compounds of this general structure may be prepared by reacting 7-methoxy-2,3,4,5-tetrahydro-1,4-benzothiazepine with alkylsulfonyl chloride or arylsulfonyl chloride, in the presence of a base such as Et₃N. Additional reactions (e.g., addition of 4-benzyl piperidine) may follow, to extend the side chain as desired. As Scheme 3 demonstrates, 2-chloroethanesulfonyl chloride (e.g., 180 mg; 1.1 mM) and Et₃N (e.g., 140 mg; 1.1 mM) may be added to 7-methoxy-2,3,4,5-tetrahydro-1,4-benzothiazepine (1) (e.g., 194 mg; 1 mM) in CH$_2$Cl$_2$ (e.g., 20 ml), at 0° C. The mixture may then be stirred (e.g., at 0° C. for 2 h), and washed (e.g., with H$_2$O and saturated NaHCO$_3$ solution). Removal of the solvent will yield a crude product, which may be purified by chromatography on silica gel. The structure may be confirmed by NMR. Scheme 3 further shows that the resulting compound's side chain may be extended by reacting the compound (e.g., 28 mg; 0.1 mM) with 4-benzyl piperidine (e.g., 21 mg; 0.13 mM) in CH$_2$Cl$_2$. After the reaction goes to completion, the excess amine may be removed by a base scavenger (e.g., 3-(2-succinic anhydride)propylfunctionalized silica gel, 0.5 g).

The present invention also provides a method for the synthesis of a compound of having formula:

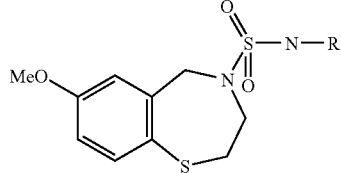

wherein R=aryl, alkyl, —(CH$_2$)$_n$NR'$_2$, or —(CH$_2$)$_n$SR', and n=0, 1, 2, or 3, and R'=alkyl or cycloalkyl, comprising the step of treating a compound having formula:

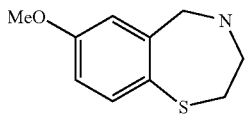

with a sulfuryl chloride and a primary or secondary amine, in the presence of a base, to form a compound having the formula:

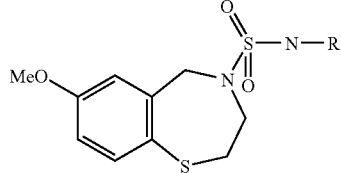

wherein R is as defined above. In one embodiment of the present invention, the base is Et₃N. In another embodiment, the primary or secondary amine is 1-piperonylpiperazine.

The method of the present invention may further comprise the step of oxidizing the compound having formula:

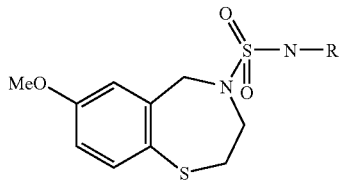

wherein R=aryl, alkyl, —(CH₂)$_n$NR'₂, or —(CH₂)$_n$SR', and n=0, 1, 2, or 3, and R'=alkyl or cycloalkyl, to form a compound having formula:

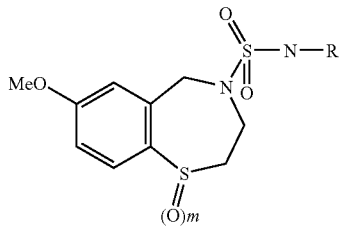

m = 1 or 2 wherein R is as defined above, and wherein m=1 or 2. In one embodiment, the oxidizing agent is hydrogen peroxide.

By way of example, and as shown in Example 11 and Scheme 4, the inventors have developed a method of synthesizing compounds having the general structure:

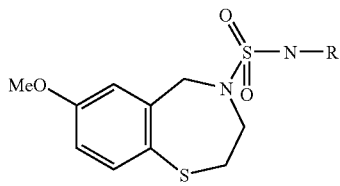

wherein R=aryl, alkyl, —(CH₂)$_n$NR'₂, or —(CH₂)$_n$SR', and n=0, 1, 2, or 3, and R'=alkyl or cycloalkyl. Novel compounds of this general structure may be prepared by a one-pot reaction of 7-methoxy-2,3,4,5-tetrahydro-1,4-benzothiazepine with sulfuryl chloride, in the presence of a base (e.g., Et₃N), followed by a primary or secondary amine. As Scheme 4 demonstrates, sulfuryl chloride (e.g., 15.0 mg; 0.111 mM) and Et₃N (e.g., 28.0 mg; 0.22 mM) may be added to 7-methoxy-2,3,4,5-tetrahydro-1,4-benzothiazepine (e.g., 19.4 mg; 0.1 mM) in CH₂Cl₂ (e.g., 20 ml), at 0° C. After stirring the mixture (e.g., for 2 h at 0° C.), 1-piperonylpiperazine (e.g., 27 mg; 0.12 mM) may be added. The mixture may be stirred for another 2 h, and then washed (e.g., with H₂O and a saturated NaHCO₃ solution). The excess amine may be removed by addition of a base scavenger (e.g., 3-(2-succinic anhydride) propylfunctionalized silica gel, 0.2 g).

The present invention further provides a method for the synthesis of a compound of having formula:

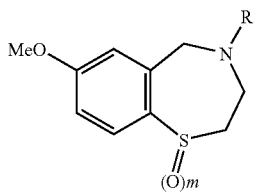

m = 1 or 2 wherein R=CO(CH₂)$_n$XR'₂, SO₂(CH₂)$_n$XR'₂, or SO₂NH(CH₂)$_n$XR'₂, and X=N or S, and n=1, 2, or 3, and R'=alkyl or cycloalkyl; and wherein m=1 or 2, comprising the step of treating a compound having formula:

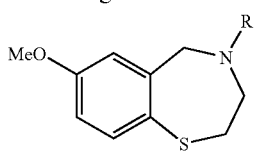

wherein R is as defined above, with an oxidizing agent, to form a compound having formula:

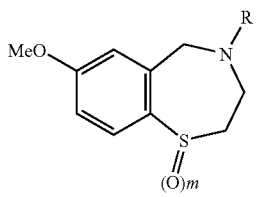

m = 1 or 2 wherein R and m are as defined above. In one embodiment, the oxidizing agent is hydrogen peroxide. This method may also be used to oxidize JTV-519.

The present invention further provides a method for the synthesis of a compound of having formula:

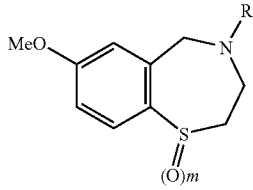

m = 1 or 2 wherein R=CO(CH₂)$_n$XR'₂, SO₂(CH₂)$_n$XR'₂, or SO₂NH(CH₂)$_n$XR'₂, and X=N or S, and n=1, 2, or 3, and R'=alkyl or cycloalkyl; and wherein m=1 or 2, comprising the step of treating a compound having formula:

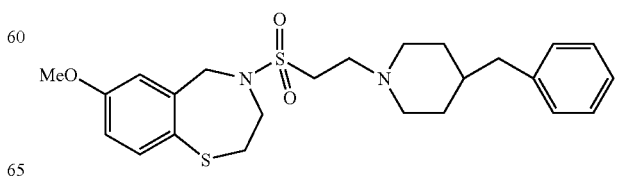

with an oxidizing agent, to form a compound having formula:

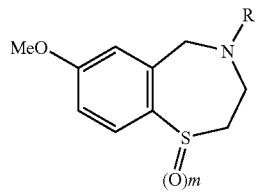

m = 1 or 2 wherein R and m are as defined above. In one embodiment, the oxidizing agent is hydrogen peroxide. This method may also be used to oxidize JTV-519.

By way of example, and as shown in Example 11 and Scheme 5, the inventors have developed a method of synthesizing compounds having the general structure:

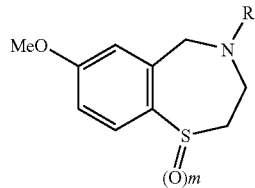

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2. Novel compounds of this general structure may be prepared by oxidation of JTV-519, or one of the novel 1,4-benzothiazepine derivatives disclosed herein, with hydrogen peroxide. As Scheme 5 shows, the 1,4-benzothiazepine compound of interest (e.g., 21 mg; 0.05 mM) in MeOH (e.g., 5 ml) may be added to H$_2$O$_2$ (e.g., 0.1 ml, excess). The mixture may be stirred (e.g., for 2 days), and the resulting product may be purified by chromatography on silica gel (e.g., CH$_2$Cl$_2$:MeOH=10:1).

Additionally, the present invention provides a method for the synthesis of a compound having formula:

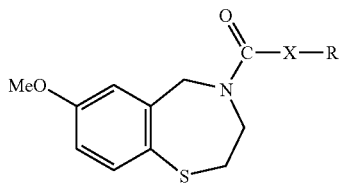

wherein R=aryl, alkyl, —(CH$_2$)$_n$NR'$_2$, or —(CH$_2$)$_n$SR', and n=0, 1, 2, or 3, and R'=alkyl or cycloalkyl; and wherein X=NH or O, comprising the step of treating a compound having formula:

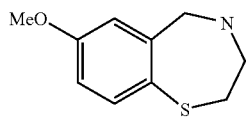

with a carbonyl chloride compound, in the presence of a base, and with a primary or secondary amine or an alcohol, to form a compound having the formula:

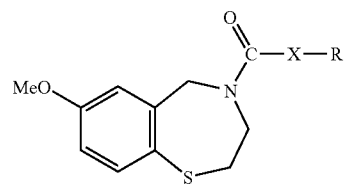

wherein R and X are as defined above. In one embodiment, the carbonyl chloride compound is triphosgene. In another embodiment, the base is Et$_3$N. In yet another embodiment, the primary or secondary amine is 4-benzylpiperidine.

By way of example, and as shown in Example 11 and Scheme 6, the inventors have developed a method of synthesizing compounds having the general structure:

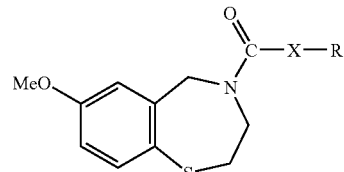

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O. Novel compounds of this general structure may be prepared by reacting 7-methoxy-2,3,4,5-tetrahydro-1,4-benzothiazepine with triphosgene, in the presence of a base (e.g., Et$_3$N), followed by addition of a primary or secondary amine or an alcohol.

The present invention further provides a method for the synthesis of 2, 3, 4, 5-tetrahydro-1,4-benzothiazepine compounds having formula:

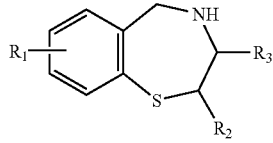

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl, comprising the steps of:

(a) treating a compound having formula:

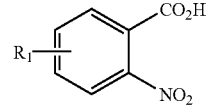

wherein R$_1$ is as defined above, with a reducing agent, in the presence of an optional catalyst, to form a compound having formula:

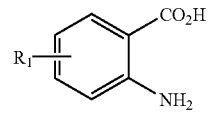

wherein R$_1$ is as defined above;

(b) treating the compound formed in step (a) with a diazotizing agent and a disulfide, to form a compound having formula:

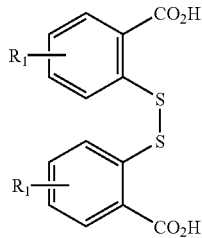

wherein $R_1$ is as defined above;

(c) treating the compound formed in step (b) with an activating agent and chloroethylamine, to form a compound having formula:

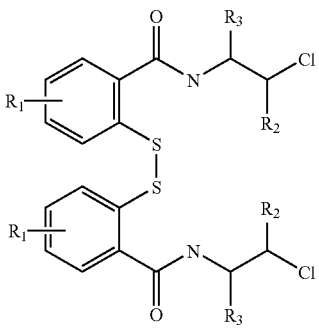

wherein $R_1$, $R_2$, and $R_3$ are as defined above;

(d) treating the compound formed in step (c) with a reducing agent and a base to form a compound having formula:

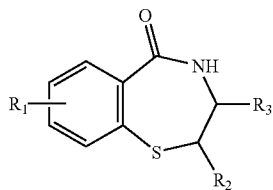

wherein $R_1$, $R_2$, and $R_3$ are as defined above; and (e) treating the compound formed in step (d) with a reducing agent, to form a compound having formula:

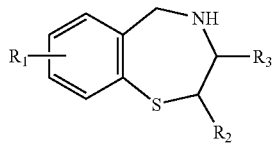

wherein $R_1$, $R_2$, and $R_3$ are as defined above.

Methods of Treatment and Prevention Using Novel 1,4-Benzothiazepine Derivatives

The inventors' novel 1,4-benzothiazepine compounds share functional characteristics with JTV-519. For example, like JTV-519 (mwt=423), compound S36 (mwt=267) regulates calcium channels. Indeed, S36 (a carboxylic acid) is approximately 10 times more potent than JTV-519 in regulating calcium channels (data not shown). Unlike JTV-519, however, the inventors' novel compounds show weak blocking activity of hERGs.

The rapid delayed rectifier (I(Kr)) channel—a potassium channel—is important for repolarization of the cardiac action potential. hERG is the pore-forming subunit of the I(Kr) channel. Suppression of I(Kr) function—as a result of adverse drug effects and/or genetic defects in hERG—can lead to long-QT (LQT) syndrome, which carries increased risk of life-threatening arrhythmias. hERGs, then, are potassium-channel subunits that, when blocked, can cause cardiac arrhythmias and sudden cardiac death.

The inventors' compounds have significantly reduced blocking of hERG (I(Kr)) channels, when compared with JTV-519. As shown in FIGS. 15-18, for example, one of the inventors' compounds, S36, has hERG blocking activity that is approximately 5- to 10-fold lower than the hERG blocking activity of JTV-519. Because the inventors' compounds have weak hERG blocking activity, they are expected to be less toxic than JTV-519.

Based upon the foregoing, the inventors' novel 1,4-benzothiazepine compounds are more potent than JTV-519, and have reduced toxicity. Thus, it is believed that the inventors' novel compounds will be particularly useful in any of the above-described methods for limiting or preventing a decrease in the level of RyR2-bound FKBP12.6 in a subject, including a subject who has, or is a candidate for, at least one cardiac condition, including, without limitation, a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, and exercise-induced sudden cardiac death. It is also believed that the inventors' compounds will be particularly useful in methods for treating or preventing such cardiac conditions in a subject.

Accordingly, the present invention further provides a method for limiting or preventing a decrease in the level of RyR2-bound FKBP12.6 in a subject, by administering an agent to the subject, in an amount effective to limit or prevent a decrease in the level of RyR2-bound FKBP12.6 in the subject. The agent of the present invention may be any 1,4-benzothiazepine derivative, including the following:

(a)

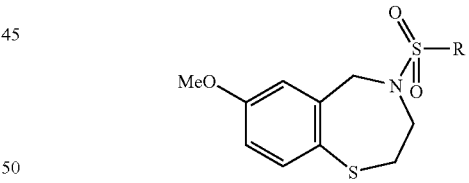

wherein R=aryl, alkenyl, alkyl, —$(CH_2)_n NR'_2$, or —$(CH_2)_n SR'$, and n=0, 1, 2, or 3, and R'=alkyl or cycloalkyl;

(b)

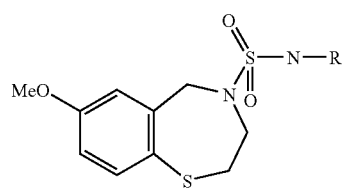

wherein R=aryl, alkyl, —$(CH_2)_n NR'_2$, or —$(CH_2)_n SR'$, and n=0, 1, 2, or 3, and R'=alkyl or cycloalkyl;

(c)

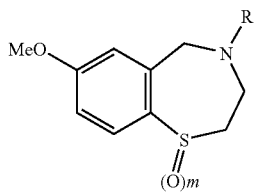

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2;

(d)

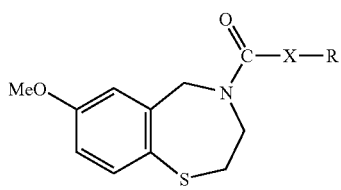

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O;

(e)

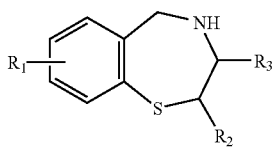

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl;

(f)

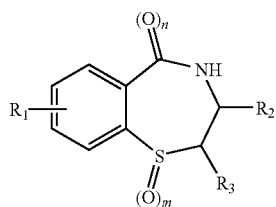

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein m=0, 1, or 2; and wherein n=0 or 1;

(g)

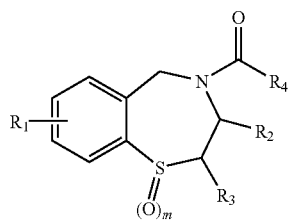

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein R4=H, halide, alkenyl, carboxylic acid, or an alkyl containing O, S, or N; and wherein m=0, 1, or 2; and (h) any oxidized form of compounds (a)-(g) above. Also provided are uses of these agents in methods for limiting or preventing a decrease in the level of RyR2-bound FKBP12.6 in a subject. In one embodiment of the present invention, the agent is selected from the group consisting of S4, S7, S-20, S-24, S-25, S-26, S-27, and S36. Structures for these agents may be found in Appendix A herein. Preferably, the agent is S36.

As described above, the subject may be any animal, but is preferably a human. In one embodiment, the subject has catecholaminergic polymorphic ventricular tachycardia (CPVT). In another embodiment, the subject has, or is a candidate for, at least one cardiac condition, including, without limitation, a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, and exercise-induced sudden cardiac death.

In the method of the present invention, a 1,4-benzothiazepine derivative may be administered to a subject as part of a therapeutic composition that comprises the derivative and a pharmaceutically-acceptable carrier, as described above. The derivative or pharmaceutical composition may be administered to the subject by way of any techniques known in the art and/or disclosed herein.

In accordance with the method of the present invention, a 1,4-benzothiazepine derivative may be administered to a subject (and the 1,4-benzothiazepine derivative may be contacted with cells of the subject) in an amount effective to limit or prevent a decrease in the level of RyR2-bound FKBP12.6 in the subject, particularly in cells of the subject. This amount may be readily determined by the skilled artisan, based upon known procedures, including analysis of titration curves established in vivo, and methods and assays disclosed herein. A suitable amount of the 1,4-benzothiazepine derivative effective to limit or prevent a decrease in the level of RyR2-bound FKBP12.6 in the subject may range from about 5 mg/kg/day to about 20 mg/kg/day, and/or may be an amount sufficient to achieve plasma levels ranging from about 300 ng/ml to about 1000 ng/ml. Preferably, the amount of the 1,4-benzothiazepine derivative ranges from about 10 mg/kg/day to about 20 mg/kg/day.

In accordance with the method of the present invention, a decrease in the level of RyR2-bound FKBP12.6 may be limited or prevented in the subject by decreasing the level of phosphorylated RyR2 in the subject. In one embodiment of the present invention, the subject has not yet developed a cardiac condition, such as a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death. In this case, the amount of the 1,4-benzothiazepine derivative effective to limit or prevent a decrease in the level of RyR2-bound FKBP12.6 in the subject may be an amount of the 1,4-benzothiazepine derivative effective to prevent a cardiac condition (e.g., cardiac arrhythmia, heart failure, or exercise-induced sudden cardiac death) in the subject. In one embodiment, the 1,4-benzothiazepine derivative prevents at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in the subject.

In another embodiment of the present invention, the subject has already developed a cardiac condition. In this case, the amount of the 1,4-benzothiazepine derivative effective to limit or prevent a decrease in the level of RyR2-bound FKBP12.6 in the subject may be an amount of the 1,4-benzothiazepine derivative effective to treat a cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia) or heart failure) in the subject. In a preferred embodiment, the JTV-519 treats at least one cardiac condition in the subject.

The present invention further provides a method for treating or preventing a cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in a subject, comprising administering an agent to the subject, in an amount effective to limit or prevent a decrease in the level of RyR2-bound FKBP12.6 in the subject. The agent of the present invention may be any 1,4-benzothiazepine derivative, including the following:

(a)

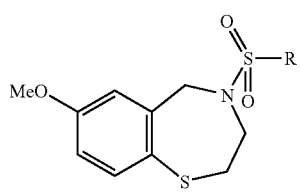

wherein R=aryl, alkenyl, alkyl, —(CH$_2$)$_n$NR'$_2$, or —(CH$_2$)$_n$SR', and n=0, 1, 2, or 3, and R'=alkyl or cycloalkyl;

(b)

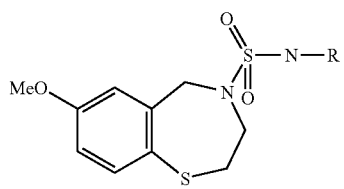

wherein R=aryl, alkyl, —(CH$_2$)$_n$NR'$_2$, or —(CH$_2$)$_n$SR', and n=0, 1, 2, or 3, and R'=alkyl or cycloalkyl;

(c)

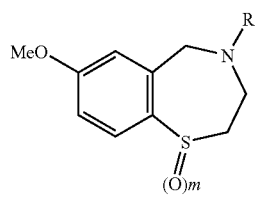

wherein R=CO(CH$_2$)$_n$XR'$_2$, SO$_2$(CH$_2$)$_n$XR'$_2$, or SO$_2$NH(CH$_2$)$_n$XR'$_2$, and X=N or S, and n=1, 2, or 3, and R'=alkyl or cycloalkyl; and wherein m=1 or 2;

(d)

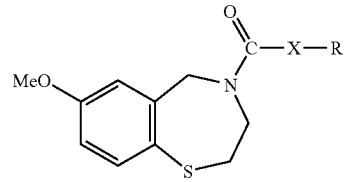

wherein R=aryl, alkyl, —(CH$_2$)$_n$NR'$_2$, —(CH$_2$)$_n$SR', and n=0, 1, 2, or 3, and R'=alkyl or cycloalkyl; and wherein X=NH or O;

(e)

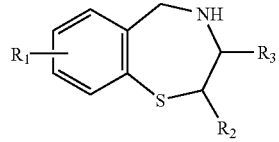

wherein R$_1$=OR', SR', NR', alkyl, or halide, at position 2, 3, 4, or 5 on the phenyl ring, and R'=alkyl, aryl, or H; wherein R$_2$=H, alkyl, or aryl; and wherein R$_3$=H, alkyl, or aryl;

(f)

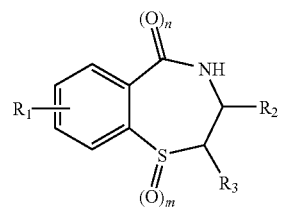

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein m=0, 1, or 2; and wherein n=0 or 1;

(g)

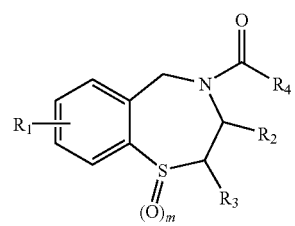

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein R4=H, halide, alkenyl, carboxylic acid, or an alkyl containing O, S, or N; and wherein m=0, 1, or 2; and (h) any oxidized form of compounds (a)-(g) above.

The present invention further provides a method for treating at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia) or heart failure) in a subject. The method comprises administering a 1,4-benzothiazepine derivative to the subject in an amount effective to treat at least one cardiac condition in the subject. A suitable amount of the 1,4-benzothiazepine derivative effective to treat a cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia) or heart failure) in a subject may range from about 5 mg/kg/day to about 20 mg/kg/day, and/or may be an amount sufficient to achieve plasma levels ranging from about 300 ng/ml to about 1000 ng/ml.

The present invention also provides a method for preventing at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in a subject. The method comprises administering a 1,4-benzothiazepine derivative to the subject in an amount effective to prevent at least one cardiac condition in the subject. A suitable amount of the 1,4-benzothiazepine derivative effective to prevent at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in a subject may range from about 5 mg/kg/day to about 20 mg/kg/day, and/or may be an amount sufficient to achieve plasma levels ranging from about 300 ng/ml to about 1000 ng/ml.

In accordance with the above-described methods, examples of the 1,4-benzothiazepine derivative include, without limitation:

(a)

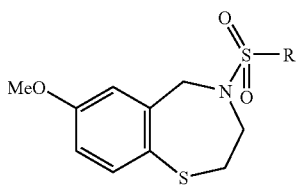

wherein R=aryl, alkenyl, alkyl, —$(CH_2)_n NR'_2$, or —$(CH_2)_n SR'$, and n=0, 1, 2, or 3, and R'=alkyl or cycloalkyl;

(b)

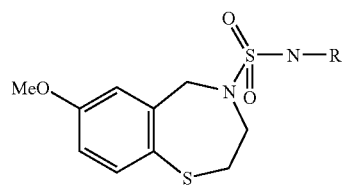

wherein R=aryl, alkyl, —$(CH_2)_n NR'_2$, or —$(CH_2)_n SR'$, and n=0, 1, 2, or 3, and R'=alkyl or cycloalkyl;

(c)

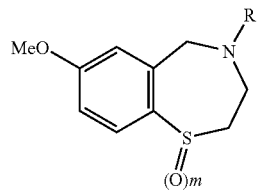

wherein R=CO$(CH_2)_n XR'_2$, SO$_2(CH_2)_n XR'_2$, or SO$_2$NH$(CH_2)_n XR'_2$, and X=N or S, and n=1, 2, or 3, and R'=alkyl or cycloalkyl; and wherein m=1 or 2;

(d)

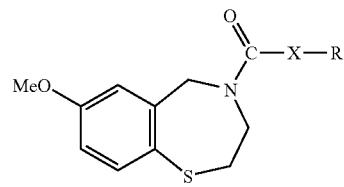

wherein R=aryl, alkyl, —$(CH_2)_n NR'_2$, —$(CH_2)_n SR'$, and n=0, 1, 2, or 3, and R'=alkyl or cycloalkyl; and wherein X=NH or O;

(e)

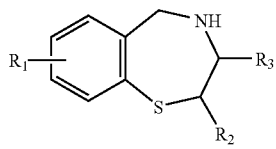

wherein $R_1$=OR', SR', NR', alkyl, or halide, at position 2, 3, 4, or 5 on the phenyl ring, and R'=alkyl, aryl, or H; wherein $R_2$=H, alkyl, or aryl; and wherein $R_3$=H, alkyl, or aryl;

(f)

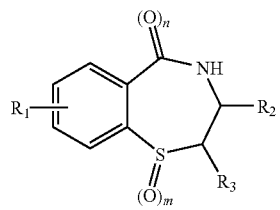

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein m=0, 1, or 2; and wherein n=0 or 1;

(g)

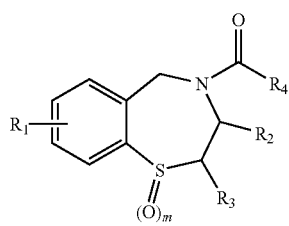

wherein R1=H, OR', SR', NR', alkyl, or halide, at position 2, 3, 4, or 5 on the phenyl ring, and R'=alkyl, aryl, or acyl; wherein R2=H, alkyl, alkenyl, or aryl; wherein R3=H, alkyl, alkenyl, or aryl; wherein R4=H, halide, alkenyl, carboxylic acid, or an alkyl containing O, S, or N; and wherein m=0, 1, or 2; and (h) any oxidized form of compounds (a)-(g) above. In one embodiment of the present invention, the 1,4-benzothiazepine derivative is selected from the group consisting of S4, S7, S-20, S-24, S-25, S-26, S-27, and S36. Preferably, the 1,4-benzothiazepine derivative is S36. The present invention also provides uses of these 1,4-benzothiazepine derivatives in methods for treating or preventing at least one cardiac condition (e.g., a cardiac arrhythmia (e.g., tachycardia; atrial arrhythmia, including atrial tachyarrhythmia and atrial fibrillation (both sustained and non-sustained); ventricular arrhythmia, including ventricular fibrillation; and exercise-induced cardiac arrhythmia), heart failure, or exercise-induced sudden cardiac death) in a subject.

The present invention also provides novel assays for regular or high-through-put screening of other biologically-active small molecules that enhance binding of FKBP12.6 and RyR2. In particular, the present invention provides a method for identifying an agent that enhances binding of RyR2 and FKBP12.6, comprising the steps of: (a) obtaining or generating a source of RyR2; (b) exposing the RyR2 to FKBP12.6, in the presence of a candidate agent; and (c) determining if the agent enhances the binding of RyR2 and FKBP12.6. In one embodiment, the RyR2 is PKA-phosphorylated. In another embodiment, the RyR2 is PKA-hyperphosphorylated. In yet another embodiment, the RyR2 is unphosphorylated.

In the method of the present invention, the RyR2 is immobilized to a solid phase, such as a plate or beads. To facilitate detection of RyR2-FKBP12.6 binding, the FKBP12.6 may be radio-labeled (e.g., with $^{32}S$). Furthermore, enhanced binding of RyR2 and FKBP12.6 may be detected using an FKBP12.6-binding agent. In one embodiment, the FKBP12.6-binding agent is an anti-FKBP12.6 antibody. The present invention also provides an agent identified by this method, as well as uses of this agent in methods for limiting or preventing a decrease in the level of RyR2-bound FKBP12.6 in a subject; in methods for treating or preventing heart failure, atrial fibrillation, or exercise-induced cardiac arrhythmia in a subject; and in methods for preventing exercise-induced sudden cardiac death in a subject.

Additionally, the present invention provides a method for identifying an agent for enhancing the binding of RyR2 and FKBP12.6, comprising the steps of: (a) obtaining or generating a source of FKBP12.6; (b) exposing the FKBP12.6 to RyR2, in the presence of a candidate agent; and (c) determining if the agent enhances the binding of RyR2 and FKBP12.6. In one embodiment, the RyR2 is PKA-phosphorylated. In another embodiment, the RyR2 is PKA-hyperphosphorylated. In yet another embodiment, the RyR2 is unphosphorylated.

In the method of the present invention, the FKBP12.6 is immobilized to a solid phase, such as a plate or beads. To facilitate detection of RyR2-FKBP12.6 binding, the RyR2 may be radio-labeled (e.g., with $^{32}P$). Furthermore, enhanced binding of RyR2 and FKBP12.6 may be detected using an RyR2-binding agent. In one embodiment, the RyR2-binding agent is an anti-RyR2 antibody. The present invention also provides an agent identified by this method, as well as uses of this agent in methods for limiting or preventing a decrease in the level of RyR2-bound FKBP12.6 in a subject; in methods for treating or preventing heart failure, atrial fibrillation, or exercise-induced cardiac arrhythmia in a subject; and in methods for preventing exercise-induced sudden cardiac death in a subject.

By way of example, and as shown in Example 12 below, a highly-efficient assay for high-throughput screening for small molecules may be developed by immobilizing FKBP12.6 (e.g., wild-type FKBP12.6 or a fusion protein, such as GST-FKBP12.6) onto a 96-well plate coated with glutathione, using standard procedures. PKA-phosphorylated ryanodine receptor type 2 (RyR2) may be loaded onto the FKBP12.6-coated plate, and incubated with JTV-519 analogues and other 1,4-benzothiazepene derivatives at various concentrations (10-100 nM) for 30 min. Thereafter, the plate may be washed to remove the unbound RyR2, and then incubated with anti-RyR2 antibody (e.g., for 30 min). The plate may be washed again to remove unbound anti-RyR2 antibody, and then treated with florescent-labeled secondary antibody. The plate may be read by an automatic fluorescent plate reader for binding activity.

Alternatively, RyR2 may be PKA-phosphorylated in the presence of $^{32}P$-ATP. Radioactive PKA-phosphorylated RyR2 may be loaded onto an FKBP12.6-coated, 96-well plate, in the presence of JTV-519 analogues and other 1,4-benzothiazepene derivatives at various concentrations (10-100 nM) for 30 min. The plate may be washed to remove the unbound radiolabeled RyR2, and then read by an automatic plate reader. PKA-phosphorylated RyR2 also may be coated to the plate, and incubated with $^{32}S$-labeled FKBP12.6 in the presence of the analogues and derivatives.

The present invention is described in the following Examples, which are set forth to aid in the understanding of the invention, and should not be construed to limit in any way the scope of the invention as defined in the claims which follow thereafter.

EXAMPLES

Example 1

FKBP12.6-Deficient Mice

FKBP12.6-deficient mice were generated, as previously described (Wehrens et al., FKBP12.6 deficiency and defective calcium release channel (ryanodine receptor) function linked to exercise-induced sudden cardiac death. *Cell*, 113: 829-40, 2003). Briefly, mouse genomic λ-phage clones for the murine orthologue of the human FK506 binding protein 12.6 (FKBP12.6) were isolated from a DBA/1lacJ library, using a full-length murine cDNA probe. The targeting vector was designed to delete exons 3 and 4, which contain the entire coding sequences for murine FKBP12.6 (Bennett et al., Identification and characterization of the murine FK506 binding protein (FKBP) 12.6 gene. *Mamm. Genome*, 9:1069-71, 1998), by replacing 3.5 kb of murine genomic DNA with a PGK-neo selectable marker. A 5.0-kb 5' fragment and a 1.9-kb 3' fragment were cloned into pJNS2, a backbone vector with PGK-neo and PGK-TK cassettes. The DBA/lacJ embryonic stem (ES) cells were grown and transfected, using established protocols. Targeted ES cells were first screened by Southern analysis, and 5 positive ES cell lines were analyzed by PCR to confirm homologous recombination. Male chimeras were bred to DBA/1lacJ females, and germline offspring identified by brown coat color. Germline offspring were genotyped using 5' Southern analysis. Positive FKBP12.6+/− males and females were intercrossed, and offspring resulted in FKBP12.6$^{-/-}$ mice at approximately 25% frequency. FKBP12.6$^{-/-}$ mice were fertile.

All studies performed with FKBP12.6$^{-/-}$ mice used age- and sex-matched FKBP12.6$^{+/+}$ mice as controls. No differences were observed between FKBP12.6$^{-/-}$ mice raised on the following backgrounds: DBA/C57BL6 mixed, pure DBA, and pure C57BL6.

Example 2

Telemetry Recording and Exercise Testing in Mice

FKBP12.6$^{+/+}$ and FKBP12.6$^{-/-}$ mice were maintained and studied according to protocols approved by the Institutional Animal Care and Use Committee of Columbia University. Mice were anaesthetized using 2.5% isoflurane inhalation anesthesia. ECG radiotelemetry recordings of ambulatory animals were obtained >7 days after intraperitoneal implantation (Data Sciences International, St. Paul, Minn.) (Wehrens et al., FKBP12.6 deficiency and defective calcium release channel (ryanodine receptor) function linked to exercise-induced sudden cardiac death. Cell, 113:829-40, 2003). For stress tests, mice were exercised on an inclined treadmill until exhaustion, and then intraperitoneally injected with epinephrine (0.5-2.0 mg/kg) (Wehrens et al., FKBP12.6 deficiency and defective calcium release channel (ryanodine receptor) function linked to exercise-induced sudden cardiac death. Cell, 113:829-40, 2003). Resting heart rates of ambulatory animals were averaged over 4 h.

Example 3

Expression of Wild-Type and RyR2-S2809D Mutants

Mutagenesis of the PKA target site on RyR2 (RyR2-S2809D) was performed, as previously described (Wehrens et al., FKBP12.6 deficiency and defective calcium release channel (ryanodine receptor) function linked to exercise-induced sudden cardiac death. Cell, 113:829-40, 2003). HEK293 cells were co-transfected with 20 µg of RyR2 wild-type (WT) or mutant cDNA, and with 5 µg of FKBP12.6 cDNA, using Ca$^{2+}$ phosphate precipitation. Vesicles containing RyR2 channels were prepared, as previously described (Wehrens et al., FKBP12.6 deficiency and defective calcium release channel (ryanodine receptor) function linked to exercise-induced sudden cardiac death. Cell, 113:829-40, 2003).

Example 4

RyR2 PKA Phosphorylation and FKBP12.6 Binding

Cardiac SR membranes were prepared, as previously described (Marx et al., PKA phosphorylation dissociates FKBP12.6 from the calcium release channel (ryanodine receptor): defective regulation in failing hearts. Cell, 101: 365-76, 2000; Kaftan et al., Effects of rapamycin on ryanodine receptor/Ca$^{2+}$-release channels from cardiac muscle. Circ. Res., 78:990-97, 1996). $^{35}$S-labelled FKBP12.6 was generated using the TNT™ Quick Coupled Transcription/ Translation system from Promega (Madison, Wis.). [$^{3}$H] ryanodine binding was used to quantify RyR2 levels. 100 µg of microsomes were diluted in 100 µl of 10-mM imidazole buffer (pH 6.8), incubated with 250-nM (final concentration) [$^{35}$S]-FKBP12.6 at 37° C. for 60 min, then quenched with 500 µl of ice-cold imidazole buffer. Samples were centrifuged at 100,000 g for 10 min, and washed three times in imidazole buffer. The amount of bound [$^{35}$S]-FKBP12.6 was determined by liquid scintillation counting of the pellet.

Example 5

Immunoblots

Immunoblotting of microsomes (50 µg) was performed as described, with anti-FKBP12/12.6 (1:1,000), anti-RyR-5029 (1:3,000) (Jayaraman et al., FK506 binding protein associated with the calcium release channel (ryanodine receptor). J. Biol. Chem., 267:9474-77, 1992), or anti-phosphoRyR2-P2809 (1:5,000) for 1 h at room temperature (Reiken et al., Beta-blockers restore calcium release channel function and improve cardiac muscle performance in human heart failure. Circulation, 107:2459-66, 2003). The P2809-phospho-epitope-specific anti-RyR2 antibody is an affinity-purified polyclonal rabbit antibody, custom-made by Zymed Laboratories (San Francisco, Calif.) using the peptide, CRTRRI-(pS)-QTSQ, which corresponds to RyR2 PKA-phosphorylated at Ser$^{2809}$. After incubation with HRP-labeled anti-rabbit IgG (1:5,000 dilution; Transduction Laboratories, Lexington, Ky.), the blots were developed using ECL (Amersham Pharmacia, Piscataway, N.J.). The antibodies may also be used in the following ratios: 1:4,000 (anti-rabbit IgG); and 1:5,000 (anti-RyR2-5029 and anti-FKBP12.6).

Example 6

Single-Channel Recordings

Single-channel recordings of native RyR2 from rodent (mouse or rat) hearts, or recombinant RyR2, were acquired under voltage-clamp conditions at 0 mV, as previously described (Marx et al., PKA phosphorylation dissociates FKBP12.6 from the calcium release channel (ryanodine receptor): defective regulation in failing hearts. Cell, 101: 365-76, 2000). Symmetric solutions used for channel recordings were: trans compartment—HEPES, 250 mmol/L; Ba(OH)$_2$, 53 mmol/L (in some experiments, Ba(OH)$_2$ was replaced by Ca(OH)$_2$); pH 7.35; and cis compartment—HEPES, 250 mmol/L; Tris-base, 125 mmol/L; EGTA, 1.0 mmol/L; and CaCl$_2$, 0.5 mmol/L; pH 7.35. Unless otherwise indicated, single-channels recordings were made in the presence of 150-nM [Ca$^{2+}$] and 1.0-mM [Mg$^{2+}$] in the cis compartment. Ryanodine (5 mM) was applied to the cis compartment to confirm identity of all channels. Data were analyzed from digitized current recordings using Fetchan software (Axon Instruments, Union City, Calif.). All data are expressed as mean±SE. The unpaired Student's t-test was used for statistical comparison of mean values between experiments. A value of p<0.05 was considered statistically significant.

The effects of JTV-519 on RyR2 channels are set forth in FIGS. 1-3 and Table 1 (below). As demonstrated in FIG. 3, the single-channel studies showed increased open probability of RyR2 following PKA phosphorylation (D), as compared to PKA phosphorylation in the presence of the specific PKA inhibitor, $PKI_{5-24}$ (C). Single-channel function was normalized in PKA-phosphorylated RyR2 incubated with FKBP12.6 in the presence of JTV-519 (E). Amplitude histograms (right) revealed increased activity and subconductance openings in PKA-phosphorylated RyR2, but not following treatment with JTV-519 and FKBP12.6. FIG. 3F shows that incubation of PKA-phosphorylated RyR2 with FKBP12.6, in the presence of JTV-519, shifted the $Ca^{2+}$-dependence of RyR2 activation towards the right, making it similar to the $Ca^{2+}$-dependence of unphosphorylated channels.

TABLE 1

Ambulatory ECG data before, during exercise, and following exercise and injection with epinephrine.

|  | SCL (ms) | HR (bpm) | PR (ms) | QRS (ms) | QT (ms) | QTc (ms) |
| --- | --- | --- | --- | --- | --- | --- |
| Baseline |  |  |  |  |  |  |
| $FKBP12.6^{+/-}$ | 104 ± 6 | 586 ± 36 | 32 ± 1.5 | 9.9 ± 0.4 | 30 ± 1.0 | 29 ± 0.6 |
| $FKBP12.6^{+/-}$ + JTV-519 | 99 ± 5 | 608 ± 32 | 33 ± 0.6 | 9.3 ± 0.3 | 32 ± 2.7 | 32 ± 1.9 |
| $FKBP12.6^{-/-}$ + JTV-519 | 116 ± 9 | 527 ± 43 | 33 ± 0.4 | 10.0 ± 0.3 | 33 ± 1.3 | 30 ± 1.1 |
| Maximum exercise |  |  |  |  |  |  |
| $FKBP12.6^{+/-}$ | 80 ± 2 | 752 ± 18 | 28 ± 0.7 | 8.7 ± 0.4 | 30 ± 1.7 | 33 ± 1.6 |
| $FKBP12.6^{+/-}$ + JTV-519 | 90 ± 7 | 676 ± 49 | 29 ± 1.8 | 9.6 ± 0.4 | 34 ± 2.0 | 36 ± 0.9 |
| $FKBP12.6^{-/-}$ + JTV-519 | 83 ± 3 | 729 ± 22 | 29 ± 2 | 9.3 ± 0.3 | 30 ± 1.2 | 33 ± 0.9 |
| Post-exercise epinephrine |  |  |  |  |  |  |
| $FKBP12.6^{+/-}$ | 94 ± 4 | 645 ± 28 | 35 ± 2.6 | 9.3 ± 0.4 | 33 ± 1.8 | 34 ± 1.9 |
| $FKBP12.6^{+/-}$ + JTV-519 | 102 ± 4 | 592 ± 21 | 37 ± 2.6 | 9.9 ± 0.6 | 32 ± 2.3 | 32 ± 1.7 |
| $FKBP12.6^{-/-}$ + JTV-519 | 103 ± 4 | 585 ± 20 | 35 ± 3.8 | 11.1 ± 0.5 | 36 ± 1.2 | 36 ± 1.3 |

Summary of ambulatory ECG data in $FKBP12.6^{+/-}$ mice treated with JTV-519 (n = 8) or control (n = 6), and $FKBP12.6^{-/-}$ mice treated with JTV-519 (n = 5).
SCL = sinus cycle length;
HR = heart rate;
ms = millisecond;
bpm = beats per minute;
$FKBP12.6^{+/-}$ = FKBP12.6 heterozygous mice;
$FKBP12.6^{-/-}$ = FKBP12.6 deficient mice Example 7

Rat Model of Heart Failure

Sprague-Dawley (300-400 g) underwent left coronary ligation, via left thoracotomy, to produce myocardial infarction, as previously described (Alvarez et al., Late post-myocardial infarction induces a tetrodotoxin-resistant $Na^+$ current in rat cardiomyocytes. *J. Mol. Cell Cardiol.*, 32:1169-79, 2000). Briefly, rats were anesthetized with a mixture of 150 mg/kg intraperitoneal ketamine and 15 mg/kg chlorpromazine. Respiration was maintained with a ventilation assist device and an endotracheal tube (3 ml air/60 strokes per min). After median-left thoracotomy and pericardium opening, the left main coronary artery was occluded with a 7-0 silk suture at the most proximal point below the left atria appendage. Sham-operated rats (n=5) were treated in the same manner, but without coronary artery ligation.

Six weeks after myocardial infarction, heart failure was confirmed using echocardiography. JTV-519 or vehicle (DMSO) was continuously infused (0.5 mg/kg/h) by means of an implantable osmotic infusion pump (Alzet mini-osmotic pump; Durect Corporation, Cupertino, Calif.). After 4 weeks of continuous treatment, echocardiography and hemodynamic measurements were performed. Animals were sacrificed, and tissue samples were harvested.

Figure 4:
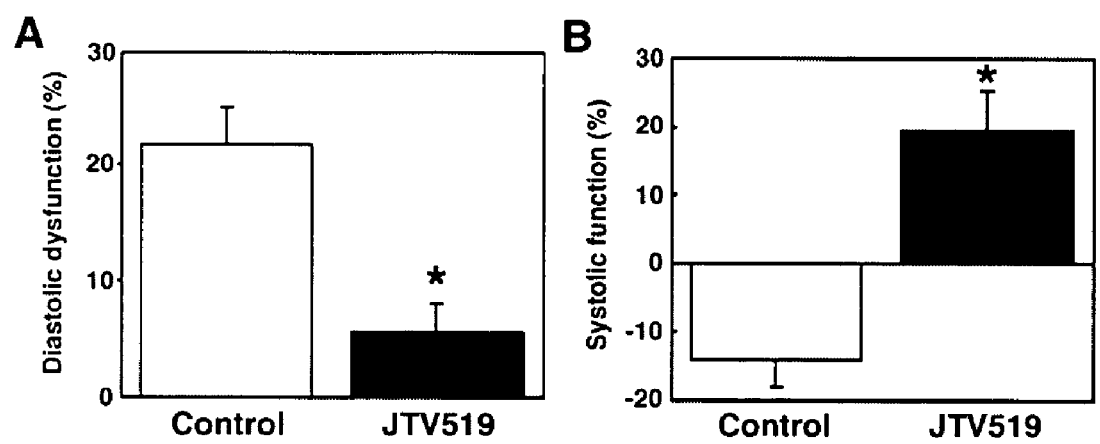
FIG. 4 shows that JTV-519 improves cardiac contractility in a rat model of heart failure. (A) Myocardial diastolic cross-sectional area was determined at mid-papillary levels using echocardiography, before and after a 4-week treatment with JTV-519 or vehicle (control). The relative increase in diastolic dysfunction was inhibited by JTV-519. (B) Although systolic function deteriorated in non-treated animals, JTV-519 significantly increased systolic function in post-myocardial-infarction (post-MI) heart-failure rats.

In accordance with the above techniques, heart failure was induced in rats by ligation of the left anterior descending coronary artery. This resulted in myocardial infarction that developed into dilated cardiomyopathy, with reduced cardiac function, within 4 weeks. Three groups of animals were studied, with 25 in each group: sham-operated (control), heart failure+therapy (JTV-519), and heart failure without therapy (vehicle). A four-week treatment with JTV-519 significantly reduced diastolic and systolic dysfunction, as determined by echocardiography (FIG. 4). Thus, the therapy with JTV-519 significantly improved cardiac function and reduced the progression of heart failure in the rat model of ischemic-induced heart failure.

Figure 5:
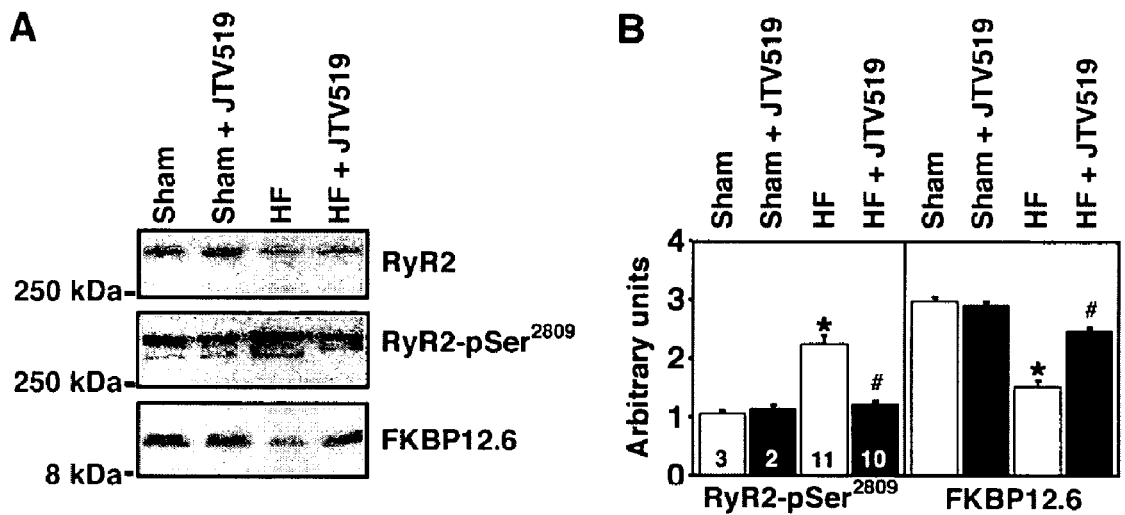
FIG. 5 demonstrates that JTV-519 increases calstabin2 (FKBP12.6) affinity to RyR2 in heart-failure rats. Equivalent amounts of RyR2 were immunoprecipitated using anti-RyR2 antibody (A). Representative immunoblots (A) and bar graphs (B) show the amount of PKA phosphorylation of RyR2 at Ser2809 (B, left) and the amount of calstabin2 (FKBP12.6) (B, right) bound to RyR2 in the different experimental groups. In heart failure, RyR2 is significantly hyperphosphorylated by PKA (B, left), which leads to dissociation of calstabin2 (FKBP12.6) from the channel complex (B, right). Treatment with JTV-519 resulted in normalization of both PKA-phosphorylation status of RyR2, as well as FKBP12.6 binding to RyR2. The number of experiments is indicated in bars. *$P<0.05$, HF vs. sham; #$P<0.05$, HF+JTV-519 vs. HF
Figure 6:
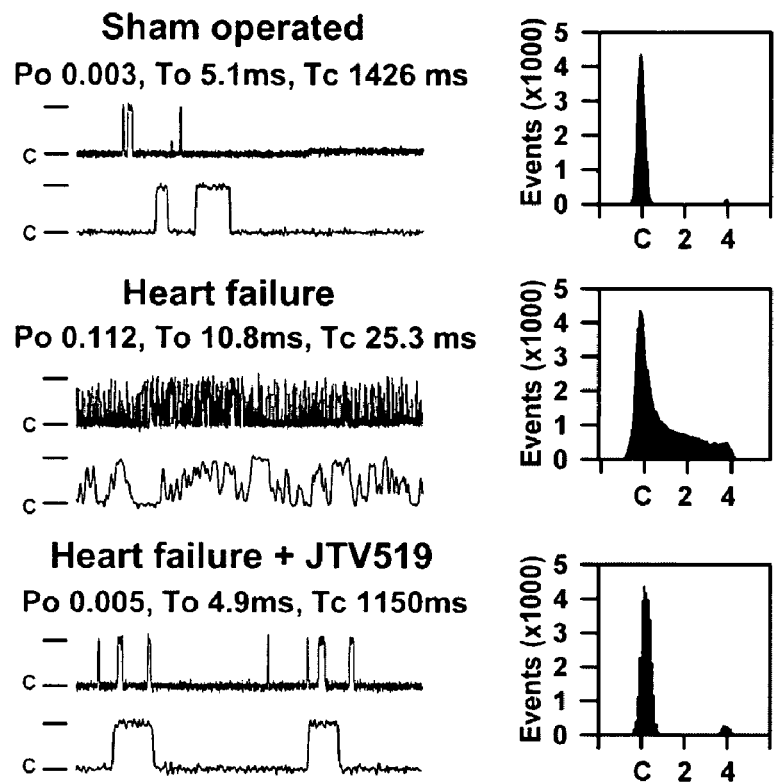
FIG. 6 illustrates that JTV-519 normalizes RyR2-channel gating in failing hearts. RyR2 channels were isolated from sham-operated (sham) or heart-failure (HF) rats. Representative single-channel tracings show that RyR2-channel open probability (Po) was significantly increased in failing hearts (middle), as compared with sham-operated rats (top). Treatment of heart-failure rats with JTV-519 for 4 weeks normalized channel open probability to levels similar to those of sham-operated animals. For each condition, the upper trace represents 5000 ms, and the bottom trace represents 200 ms. Channel openings are upward, the dash indicates the full level of channel opening (4 pA), and 'c' indicates the closed state of the channels. Amplitude histograms (right) revealed increased Po and subconductance openings in RyR2 channels from failing hearts.
Figure 7:
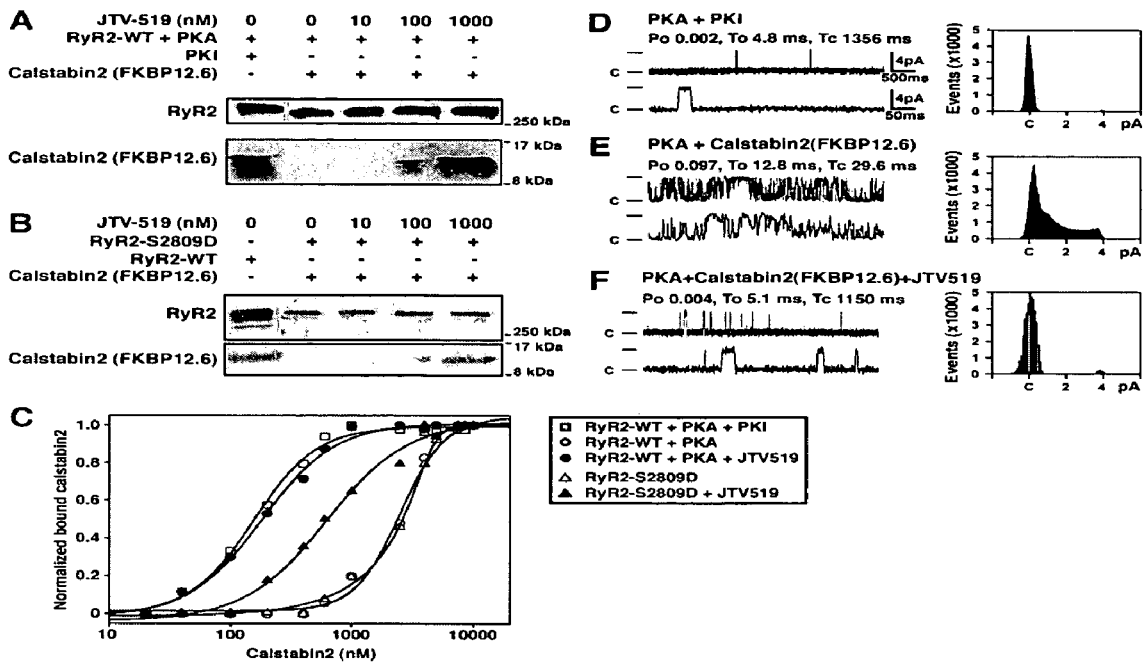
FIG. 7 demonstrates that JTV-519 normalizes RyR2 channel gating by increasing FKBP12.6 (calstabin2) binding to RyR2 channels. (A) Wild-type RyR2 (RyR2-WT) channels were PKA phosphorylated in the absence or presence of the specific PKA inhibitor $PKI_{5-24}$, then incubated with calstabin2 (FKBP12.6) in the presence of JTV-519 at the indicated concentrations. The RyR2 immunoblot shows equal amounts of RyR2 in the samples; the calstabin2 immunoblot shows that JTV-519 enabled partial (100 nM) or complete (1000 nM) rebinding of calstabin2 to PKA-phosphorylated RyR2. (B) RyR2-S2809D, which mimics constitutively-PKA-phosphorylated RyR2, was incubated with calstabin2 in the presence of the indicated concentrations of JTV-519. The RyR2 immunoblot shows equal amounts of RyR2 in the samples; the calstabin2 immunoblot shows that JTV-519 enables partial (100 nM) or complete (1000 nM) rebinding of calstabin2 to RyR2-S2809D. (C) [$^{35}$S]-labeled calstabin2 binding curves show that JTV-519 increases binding affinity of calstabin2 to PKA-phosphorylated RyR2 and RyR2-S2809D mutant channels, to a level comparable to non-phosphorylated RyR2-WT. (D-F) Single-channel studies show that JTV-519 (1 µM) reduces the open probability (Po) of PKA-phosphorylated RyR2-WT by rebinding calstabin2 at 150 nM [$Ca^{2+}$] (n=11 for D; n=12 for E; n=13 for F). Channel openings are upward, the dash indicates the full level of channel opening (4 pA), and 'c' indicates the closed state of the channels. Amplitude histograms (right) reveal increased Po and subconductance openings in PKA-phosphorylated RyR2; this was not observed following treatment with JTV-519 (1 µM) and calstabin2 (FKBP12.6).

Using a mutant RyR2-S2809D channel that mimics constitutively-PKA-phosphorylated RyR2 channels, it was determined that JTV-519 increases the affinity of FKBP12.6 for the RyR2 channel (FIG. 5). Specifically, treatment with JTV-519 enabled FKBP12.6 to bind to the mutant channel, thereby revealing a mechanism by which JTV-519 prevents heart failure. Treatment with JTV-519 also prevented the leak in the RyR2 channels of failing hearts (FIG. 6). Furthermore, JTV-519 restored binding of FKBP12.6 to both PKA-phosphorylated RyR2 and the mutant RyR2-S2809D that mimics constitutively-PKA-phosphorylated RyR2 in a dose-dependent manner (FIG. 7).

Example 8

Canine Model of Atrial Fibrillation a) Animal Protocols

Pacemakers were implanted in female adult mongrel dogs weighing 24-26 kg, using previously-described techniques (Dun et al., Chronic atrial fibrillation does not further decrease outward currents. It increases them. *Am. J. Physiol. Heart Circ. Physiol.*, 285:H1378-84, 2003). Animals were anesthetized with thiopental sodium (17 mg/kg, i.v.), and ventilated with isoflurane (1.5-2%) and $O_2$ (2 l/min). Active fixation leads were implanted in the right atrial appendage and right atrial free wall, tunneled subcutaneously, and connected to an Itrel pulse generator and Thera 8962 pacemaker, respectively (Medtronics, Minneapolis, Minn.). 40% formaldehyde (0.1-0.3 ml) was injected into the His bundle, to achieve complete AV block. The ventricular pacemaker was programmed at a rate of 60 bpm, and held at this rate throughout the pacing protocol. Following recovery, atrial pacing was instituted at a rate of 600-900 bpm, and maintained for 46±3 days, or until the animal was in chronic AF (defined as >5 days of AF in the absence of continued pacing).

Animals were then anesthetized with pentobarbital (30 mg/kg), and their hearts were removed. Atrial tissue was dissected, immediately flash-frozen in liquid nitrogen, and stored at −80° C.

b) Heart Harvest

Human data presented in this study were derived from 5 human hearts from patients with atrial fibrillation in the setting of end-stage heart failure following orthotopic heart transplant under a protocol approved by the Institutional Review Board of the New York Presbyterian Hospital. In addition, data were also obtained from samples taken from 3 normal hearts not suitable for transplantation. At the time of transplantation, hearts were preserved with cold (4° C.), hypocalcemic, hyperkalemic cardioplegia solution at explant.

c) Immunoprecipitation and Back-phosphorylation of RyR2

Cardiac membranes (100 μg), prepared from left atrial (LA) tissue as previously described (Marx, et al., PKA Phosphorylation Dissociates FKBP12.6 from the Calcium Release Channel (Ryanodine Receptor): Defective Regulation in Failing Hearts, *Cell*, 101:365-376, 2000) were suspended in 0.5 ml of RIPA buffer (50 mM Tris-HCL [pH 7.4], 0.9% NaCl, 0.25% Triton 100×, 5 mM NaF, and protease inhibitors), and then incubated with rabbit anti-RyR2 antibody overnight at 4° C. Protein A sepharose beads were added, and allowed to incubate at 4° C. for 1 h. Protein A beads were subsequently washed with 1× kinase buffer (50 mM Tris-HCL, 50 mM piperazine-N,N'-bis[2-ethanesulfonic acid], 8 mM MgCl, and 10 mM EGTA [pH 6.8]), and then resuspended in 1.5× kinase buffer. The reaction was initiated with PKA (5 units), 100 μM MgATP, and [γ²P]ATP (NEN Life Sciences, Boston); it was allowed to incubate for 8 min at room temperature, and was then stopped with 5 μl of 6× loading buffer (4% SDS and 0.25 M DTT). Samples were heated to 95° C., and then size-fractionated on 6% SDS-PAGE. RyR2 radioactivity was quantified using a Molecular Dynamics Phosphoimager, and Imagequant software (Amersham Pharmacia Biotech, Pescataway, N.J.). Values were divided by the amount of immunoprecipitated RyR2 (determined by immunoblotting and densitometry), and expressed as the inverse of the $[\gamma^{32}P]ATP$ signal.

d) Calstabin2 (FKBP12.6) Rebinding with JTV-519

RyR2 was immunoprecipitated from atrial SR (100 μg), and washed with 1× kinase buffer, as described above. The immunoprecipitated RyR2 was phosphorylated with PKA (5 units) and 100 μM MgATP at room temperature, and the reaction was terminated after 8 min by washing with ice-cold RIPA buffer. Recombinant calstabin2 (FKBP12.6; 200 nM) was subsequently incubated with the phosphorylated RyR2 at room temperature, in the presence or absence of the 1,4-benzothiazepine derivative, JTV-519 (1 μM). After washing the reaction with RIPA buffer, the proteins were size-fractionated by 15% SDS PAGE, and immunoblotted for calstabin2 (FKBP12.6).

Summarized below are results obtained by the inventors in connection with the experiments of Example 8:

Regulation of Atrial RyR2

Figure 8:
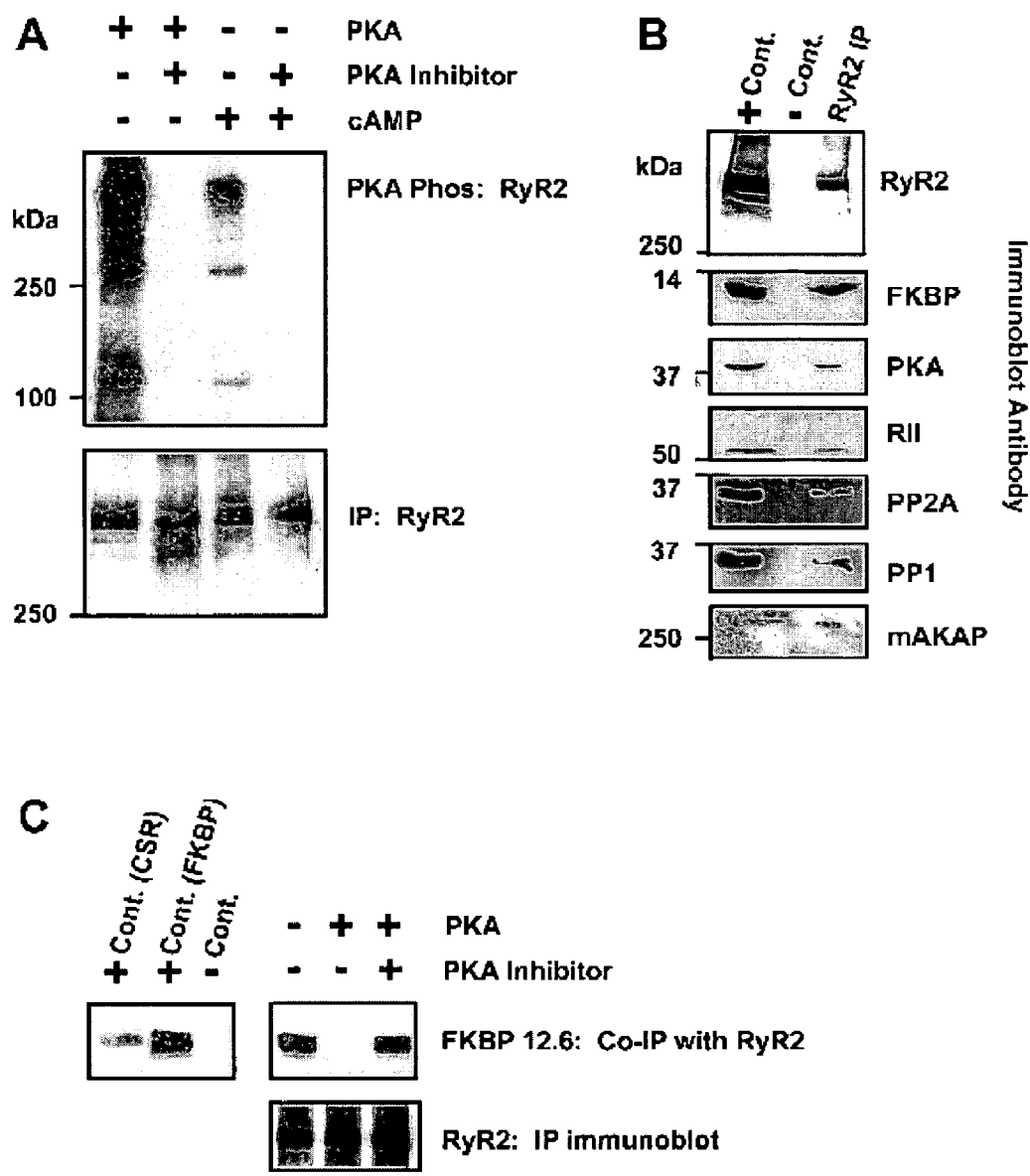
FIG. 8 illustrates the RyR2 macromolecular complex in atrial tissue. (A) RyR2 was immunoprecipitated from atrial sarcoplasmic reticulum (SR), and phosphorylated with PKA or cyclic adenosine monophosphate (cAMP). Addition of PKA inhibitor (PKI) completely blocked the phosphorylation reaction. (B) Components of the RyR2 macromolecular complex were co-immunoprecipitated with RyR2 from atrial SR. The positive control was atrial SR (with 50% of immunoprecipitation (IP) input). The negative control represents samples immunoprecipitated with antibody blocked with the antigenic peptide. (C) Calstabin2 (FKBP12.6) was co-immunoprecipitated with RyR2 from atrial SR. Prior to size-fractionation by SDS PAGE, samples were phosphorylated with PKA in the presence and absence of PKI. PKA phosphorylation caused dissociation of calstabin2 (FKBP12.6) from the channel complex, in a manner inhibited by PKI. +Cont. (CSR)= atrial SR; +Cont. (FKBP)=recombinant FKBP; –Cont. =IP performed with antibody pre-absorbed with antigenic peptide.

Atrial RyR2 was PKA phosphorylated (FIG. 8A), in accordance with the above techniques. PKA phosphorylation of atrial RyR2 reduced the amount of calstabin2 (FKBP12.6) in the RyR2 macromolecular complex, as determined by co-immunoprecipitation (FIG. 8C). The atrial RyR2 macromolecular complex comprised calstabin2 (FKBP12.6), the catalytic subunit of PKA, the PKA regulatory subunit (R11), PP2A, PP1, and mAKAP (FIG. 8B), as previously reported for ventricular RyR2 (Marx et al., PKA phosphorylation dissociates FKBP12.6 from the calcium release channel (ryanodine receptor): defective regulation in failing hearts. *Cell*, 101:365-76, 2000).

PKA Hyperphosphorylation of the Ryanodine Receptor in Atrial Fibrillation

Figure 9:
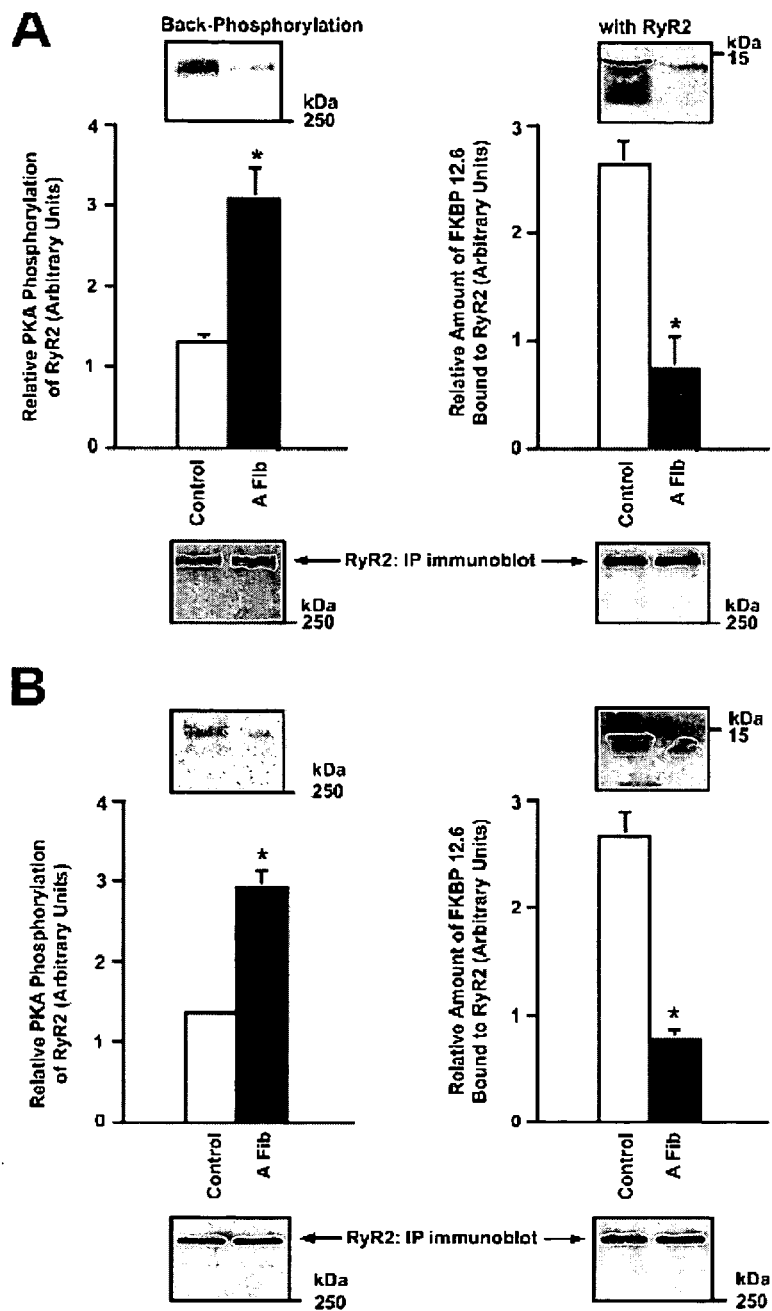
FIG. 9 shows PKA-hyperphosphorylation of RyR2 in atrial fibrillation (AF). (A) Immunoprecipitated (IP) RyR2 from control animals (Control; n=6) and dogs with atrial fibrillation (A Fib; n=6) was phosphorylated with PKA. For back-phosphorylation experiments, immunoblotting for RyR2 was performed in parallel, in order to determine the amount of RyR2 protein that was immunoprecipitated in each sample. The bar graph on the left represents a quantification of the back-phosphorylation studies. Values represent the relative degrees of PKA phosphorylation of RyR2, adjusted for the amount of immunoprecipitated protein. Dogs with AF showed a 130% increase in PKA phosphorylation, as compared with controls (n=6 for AF; n=6 for control; P=0.001). Calstabin2 (FKBP12.6) was co-immunoprecipitated with RyR2. For co-immunoprecipitation experiments, an immunoblot for RyR2 was performed in parallel, in order to determine the amount of RyR2 protein that was immunoprecipitated from each sample. The bar graph on the right represents a quantification of the co-immunoprecipitation experiments. Values represent the amount of calstabin2 (FKBP12.6) co-immunoprecipitated with RyR2, adjusted for the amount of immunoprecipitated protein. Calstabin2 (FKBP12.6) binding to RyR2 showed a 72% decrease in AF dogs, as compared with controls (n=6 for controls; n=7 for AF; P<0.0005). (B) An identical series of experiments was performed using human atrial tissue from patients with atrial fibrillation in the setting of heart failure (A Fib; n=5) and atrial tissue from patients with normal hearts (Control; n=3). The bar graph on the left represents a quantification of the back-phosphorylation studies. Humans with AF showed a 112% increase in PKA phosphorylation, as compared with controls (n=5 for A Fib; n=3 for Control; P=0.002). The bar graph on the right represents results of calstabin2 (FKBP12.6) co-immunoprecipitation experiments. Humans with AF showed a 70% decrease in the amount of calstabin2 (FKBP12.6) bound to RyR2 (n=5 for A Fib; n=3 for Controls; P<0.0001).

PKA phosphorylation of immunoprecipitated RyR2 was increased by 130% in atrial tissue from dogs with sustained atrial fibrillation (AF), as compared with controls (n=6 for AF, n=6 for control, P<0.001; FIG. 9A). Calstabin2 (FKBP12.6) binding to RyR2 was decreased by 72% in atrial tissue from dogs with sustained AF, relative to controls (n=7 for AF, n=6 for control, P<0.0005; FIG. 9A).

Similarly, PKA phosphorylation of immunoprecipitated RyR2 was increased by 112% in atrial tissue from humans with chronic atrial fibrillation, in the setting of heart failure, as compared with controls (n=5 for AF, n=3 for control, P=0.002; FIG. 9B). Calstabin2 (FKBP12.6) binding to RyR2 was decreased by 70% (n=5 for AF, n=3 for control, P<0.0001; FIG. 9B).

For all back-phosphorylation and co-immunoprecipitation experiments, the total amount of RyR2 loaded was confirmed by a parallel immunoblot of immunoprecipitated RyR2 with an anti-RyR2-5029 antibody (FIGS. 9A and 9B).

Cardiac Ryanodine Receptor Channel Function

Figure 10:
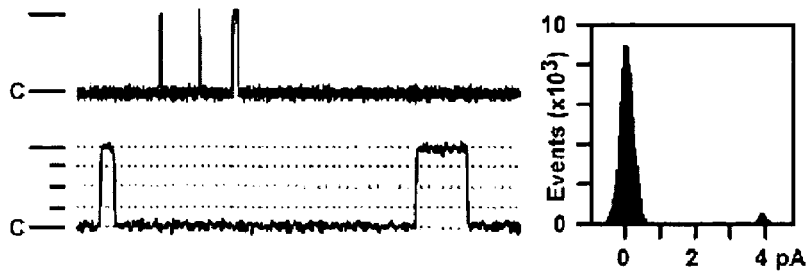
FIG. 10 illustrates altered RyR2-channel function in AF. (A) Top traces show representative RyR2 channels from left atria of controls; lower traces are AF channels. To the right of the traces are the corresponding current amplitude histograms. (B) Bar graphs show quantification of open probability (Po) and frequency of opening (Fo) for control dogs (Cont.) and dogs with chronic atrial fibrillation (A Fib). 17 channels from 5 A Fib dogs, and 11 channels from 5 control dogs, were studied. Channels from the control dogs did not demonstrate increased activity. In contrast, 15 of 17 channels (88%) from A Fib dogs showed significantly increased open probability (AF: 0.39±0.07; control: 0.009±0.002; P<0.001) and gating frequency (AF: 21.9±4.6 s$^{-1}$; control: 1.6±0.6 s$^{-1}$; P<0.002).
Figure 10:
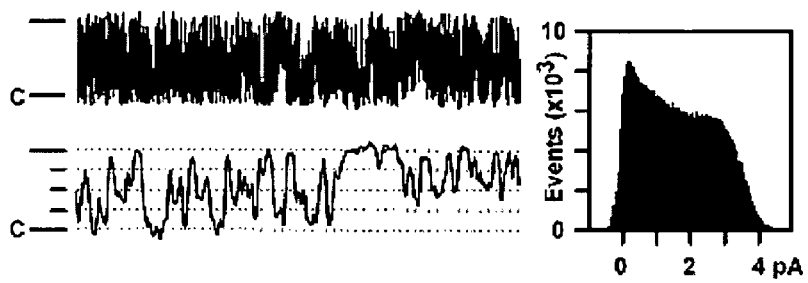
Figure 10:
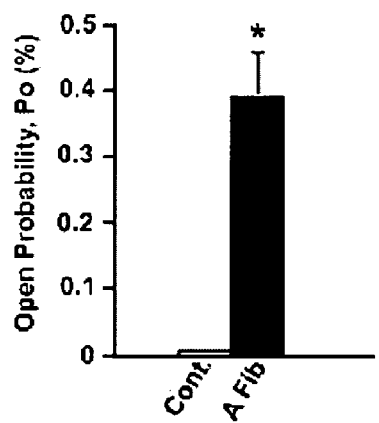
Figure 10:
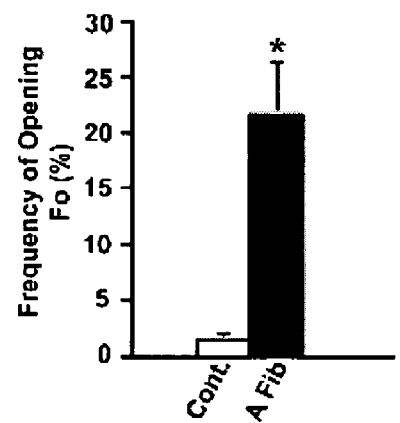

To determine the physiologic significance of the RyR2 PKA hyper-phosphorylation that was observed in AF dogs, RyR2 single-channel measurements were taken under voltage-clamp conditions, at 0 mV in planar lipid bilayers, using symmetrical ionic conditions. Atrial RyR2 single-channel properties were studied in 17 channels from 5 AF dogs, and in 11 channels from 5 control dogs. No channels from control dogs demonstrated increased activity, whereas 15 of 17 channels (88%) from AF dogs showed significantly increased open probability ($P_o$; AF: 0.412±0.07; control: 0.008±0.002; P<0.001) and gating frequency ($F_o$; AF: 21.9±4.6; control: 1.6±0.6 $s^{-1}$; P<0.002 (FIGS. 10A and 10B).

Calstabin2 (FKBP12.6) Rebinding in Presence of JTV-519

Treatment with JTV-519 (1 mM), allowed recombinant calstabin2 (FKBP12.6) to bind to PKA-phosphorylated RyR2 that had been isolated from normal canine myocardium. In the absence of JTV-519, calstabin2 (FKBP12.6) was unable to associate with PKA-phosphorylated RyR2 in these experiments (FIG. 11B).

The physiologic significance of FKBP-12.6 rebinding in the presence of JTV-519 was demonstrated by RyR2 single-channel measurements in planar lipid bilayers. In the presence of recombinant calstabin2 (FKBP12.6) alone, isolated channels demonstrated markedly-abnormal behavior, with increased open probability (Po) and the presence of subconductance states. These abnormalities in channel function were not seen when a specific PKA inhibitor (PKI) was added, indicating that the observed abnormalities in channel function were specific to RyR2 phosphorylation by PKA.

Figure 11:
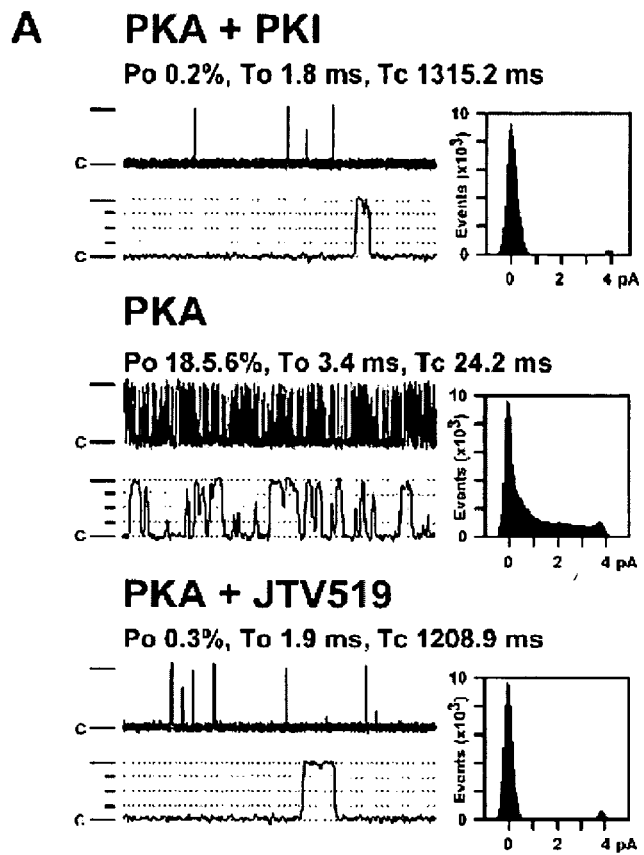
FIG. 11 demonstrates that treatment with JTV-519 restores normal RyR2 function in AF. (A) Representative traces of single RyR2 channels from dog hearts, at a cytosolic Ca$^{2+}$ concentration of 150 nM (as occurs during diastole) and in the presence of 0.25 mM calstabin2 (FKBP12.6), demonstrate significantly increased open probability (Po) and gating frequency after PKA phosphorylation (control: Po=0.3±0.2%, n=6; PKA: Po=14.8±3.2%, n=7; P<0.001). As seen at a higher time resolution in the lower trace, and in the all-point histogram, PKA phosphorylation of RyR2 results in partial openings (subconductance states) that are observed when calstabin2 (FKBP12.6) is dissociated from RyR2. JTV-519 (1.0 mM) restored channel activity of PKA-phosphorylated RyR2 (Po=0.8±0.3%; n=6; P<0.001), as compared with PKA-treated RyR2; JTV-519 also resulted in a discrete current amplitude distribution in the histogram, as seen in unphosphorylated control channels. The upper and lower traces represent 5000 msec and 200 msec, respectively; the closed state is indicated by 'c'; full channel openings are shown as upward deflections to 4 pA level, as indicated by the bars; the dotted lines in the lower traces indicate 1 pA steps of partial openings. (B) Recombinant calstabin2 (FKBP12.6) was incubated with PKA-phosphorylated RyR2, in the presence or absence of the 1,4-benzothiazepine derivative, JTV-519. Immunoblotting with anti-calstabin2 antibody revealed that JTV-519 allowed recombinant calstabin2 (FKBP12.6) to bind to PKA-phosphorylated RyR2. In the absence of JTV-519, calstabin2 binding did not occur.
Figure 11:
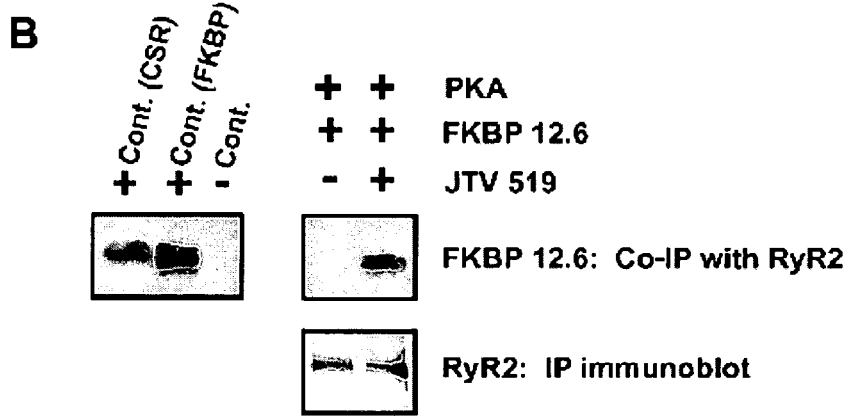

When PKA-phosphorylated channels were treated with JTV-519, in the presence of recombinant calstabin2 (FKBP12.6), single-channel measurements were similar to those observed in the presence of PKI (FIG. 11A).

Example 9

Synthesis of 1,4-Benzothiazepine Intermediate and JTV-519

For the in vivo experiments, the inventors required a gram quantity of JTV-519. However, initial attempts to prepare this compound via the reported 1,4-benzothiazepine intermediate, 7-methoxy-2,3,4,5-tetrahydro-1,4-benzothiazepine (compound 6 in Scheme 1, below), were unsuccessful. The thio group of this intermediate is easily oxidized by air to a disulfide compound, which makes the synthesis of cyclized product (5) impossible. To overcome this problem, the inventors developed a novel process that starts with the readily-available and inexpensive 2-nitro-5-methoxybenzoic acid (1). This process is depicted in Scheme 1 below.

Reduction of the nitro group of compound (1), using $H_2$ with Pd/C as a catalyst, gave 2-amino-5-methoxybenzoic acid (2) in quantitative yield. Compound (2) was diazotized with $NaNO_2$, and then treated with $Na_2S_2$ to provide the stable disulfide compound (3) with 80% yield. Without further purification, the stable disulfide (3) was treated with $SOCl_2$, and then reacted with 2-chloroethylamine, in the presence of $Et_3N$, to give an amide (4) in 90% yield. Compound (4) was converted to cyclized compound (5) via a one-pot procedure by reflux with trimethylphosphine and $Et_3N$ in THF. The cyclized amide (5) was then reduced with $LiAlH_4$ to yield 7-methoxy-2,3,4,5-tetrahydro-1,4-benzothiazepine (6).

Scheme 1

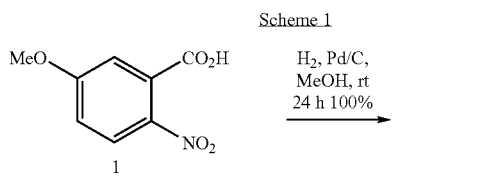

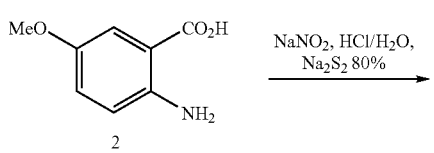

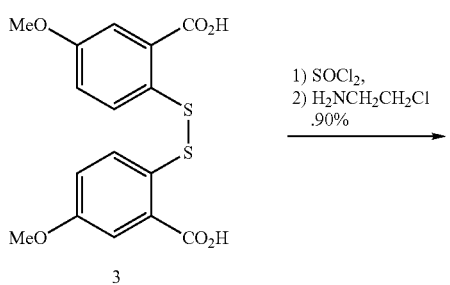

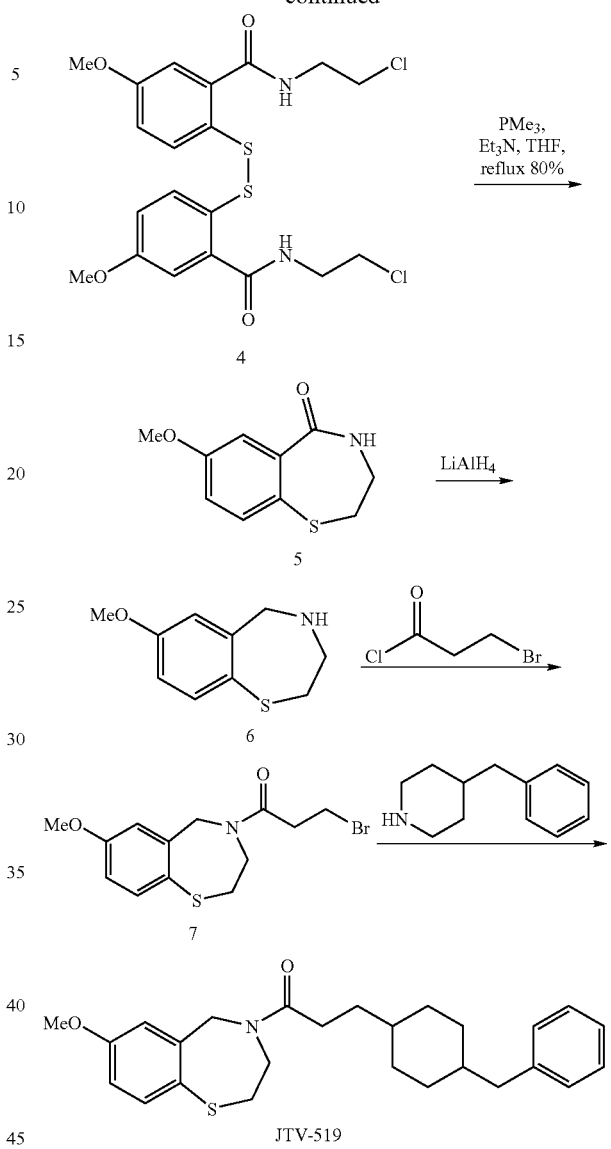

JTV-519 was prepared by reacting compound (6) with 3-bromopropionic chloride, and then reacting the resulting product with 4-benzyl piperidine. The structure of JTV-519 was established by $^1H$ NMR.

Example 10

Synthesis of Radio-Labeled JTV-519

The inventors' novel process for synthesizing radio-labeled JTV-519 is depicted in Scheme 2 below. To prepare radio-labeled JTV-519, JTV-519 was demethylated at the phenyl ring using $BBr_3$, to give phenol compound (21). The phenol compound (21) was re-methylated with a radio-labeled methylating agent (3H-dimethyl sulfate) in the presence of a base (NaH) to provide $^3H$-labeled JTV-519 (Scheme 2).

Scheme 2

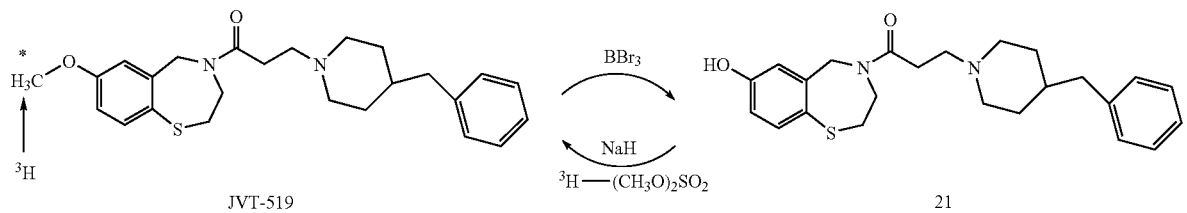

Example 11

Novel 1,4-Benzothiazepine Derivatives and Methods for their Synthesis

The inventors also developed novel 1,4-benzothiazepine derivatives for use in treating and preventing cardiac arrhythmias. In particular, the inventors produced compounds having the following general structure:

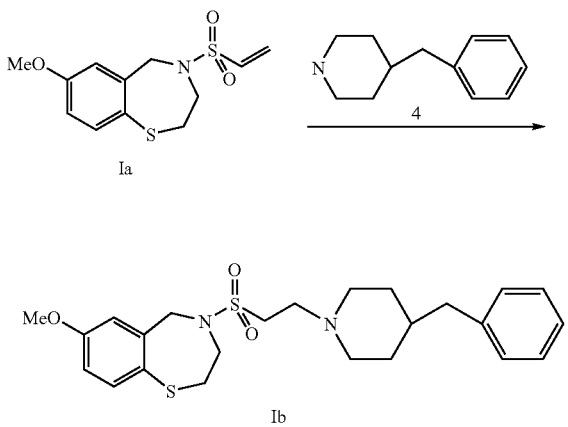

wherein R=aryl, alkenyl, alkyl, —(CH$_2$)$_n$NR'$_2$, or —(CH$_2$)$_n$SR', and n=0, 1, 2, or 3; and wherein R'=alkyl or cycloalkyl. Novel compounds of this general structure were prepared by reacting 7-methoxy-2,3,4,5-tetrahydro-1,4-benzothiazepine with alkylsulfonyl chloride or arylsulfonyl chloride, in the presence of a base such as Et$_3$N. Additional reactions (e.g., addition of 4-benzyl piperidine) may follow, to extend the side chain as desired. A representative synthesis of this general process is depicted in Scheme 3 below.

As Scheme 3 demonstrates, 2-chloroethanesulfonyl chloride (180 mg; 1.1 mM) and Et$_3$N (140 mg; 1.1 mM) were added to 7-methoxy-2,3,4,5-tetrahydro-1,4-benzothiazepine (1) (194 mg; 1 mM) in CH$_2$Cl$_2$ (20 ml), at 0° C. The mixture was stirred at 0° C. for 2 h, and washed with H$_2$O and saturated NaHCO$_3$ solution. Removal of the solvent gave crude product (Ia), which was purified by chromatography on silica gel (petroleum ether:ethyl acetate=3:1). The yield from this synthesis was 280 mg, or 95%. The structure was confirmed by NMR.

Scheme 3 further shows that the side chain of compound (Ia) was extended by reacting compound (Ia) (28 mg; 0.1 mM) with 4-benzyl piperidine (21 mg; 0.13 mM) in CH$_2$Cl$_2$. After the reaction went to completion (by TLC), the excess amine was removed by a base scavenger (3-(2-succinic anhydride)propylfunctionalized silica gel, 0.5 g). $^1$HNMR and HPLC showed that the purity of product (Ib) was >98%.

Scheme 3

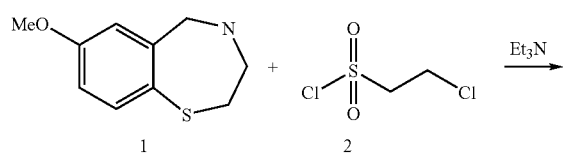

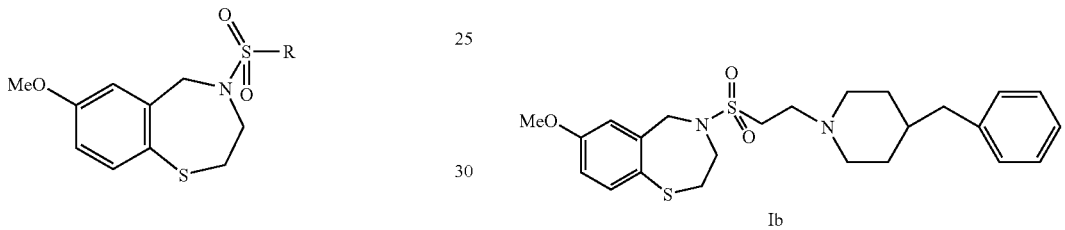

Additionally, the inventors produced compounds having the following general structure:

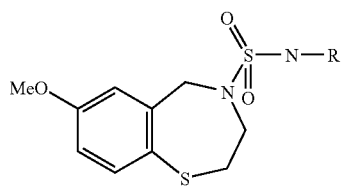

wherein R=aryl, alkyl, —(CH$_2$)$_n$NR'$_2$, or —(CH$_2$)$_n$SR', and n=0, 1, 2, or 3; and wherein R'=alkyl or cycloalkyl. Novel compounds of this general structure were prepared by a one-pot reaction of 7-methoxy-2,3,4,5-tetrahydro-1,4-benzothiazepine (1) with sulfuryl chloride, in the presence of a base (Et$_3$N), followed by a primary or secondary amine. A representative synthesis of this general process is depicted in Scheme 4 below.

As Scheme 4 demonstrates, sulfuryl chloride (15.0 mg; 0.111 mM) and Et$_3$N (28.0 mg; 0.22 mM) were added to 7-methoxy-2,3,4,5-tetrahydro-1,4-benzothiazepine (1) (19.4 mg; 0.1 mM) in CH$_2$Cl$_2$ (20 ml), at 0° C. After stirring the mixture for 2 h at 0° C., 1-piperonylpiperazine (27 mg; 0.12 mM) was added. The mixture was stirred for another 2 h, and then washed with H$_2$O and a saturated NaHCO$_3$ solution. The excess amine was removed by addition of a base scavenger (3-(2-succinic anhydride)propylfunctionalized silica gel, 0.2 g). The yield from this synthesis was 36 mg, or 77%.

Scheme 4

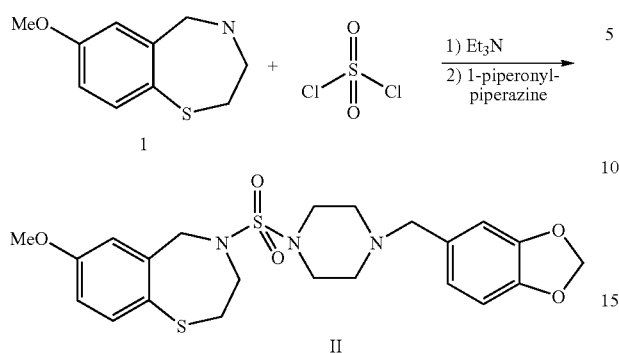

The inventors also produced compounds having the following general structure:

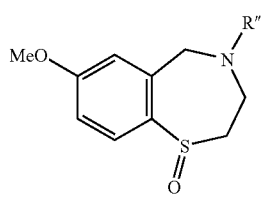

wherein R"=CO(CH$_2$)$_n$XR'"$_2$, SO$_2$(CH$_2$)$_n$XR'"$_2$, or SO$_2$NH(CH$_2$)$_n$XR'"$_2$, and X=N or S, and n=1, 2, or 3. Novel compounds of this general structure were prepared by oxidation of JTV-519, or one of the novel 1,4-benzothiazepine derivatives described above, with hydrogen peroxide. A representative synthesis of this general process is depicted in Scheme 5 below.

As Scheme 5 shows, compound (Ib) (21 mg; 0.05 mM) in MeOH (5 ml) was added to H$_2$O$_2$ (0.1 ml, excess). The mixture was stirred for 2 days, and the product III was purified by chromatography on silica gel (CH$_2$Cl$_2$:MeOH=10:1). The yield from this synthesis was 19 mg, or 91%.

Scheme 5

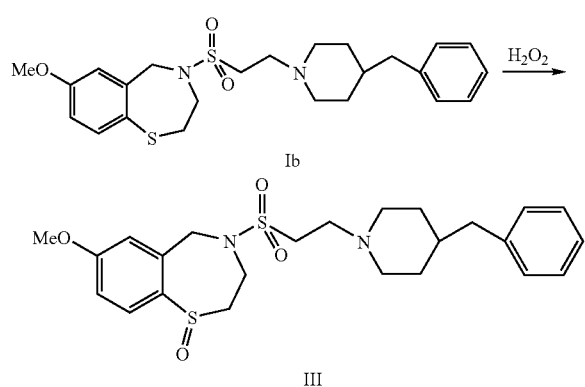

Finally, the inventors produced compounds having the following general structure:

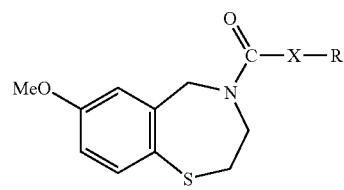

wherein R=aryl, alkyl, —(CH$_2$)$_n$NR'$_2$, —(CH$_2$)$_n$SR', and n=0, 1, 2, or 3, and R'=alkyl, cycloalkyl; and wherein X=NH or O. Novel compounds of this general structure were prepared by reacting 7-methoxy-2,3,4,5-tetrahydro-1,4-benzothiazepine (1) with triphosgene, in the presence of a base (Et$_3$N), followed by addition of a primary or secondary amine or an alcohol. A representative synthesis of this general process is depicted in Scheme 6 below.

Scheme 6

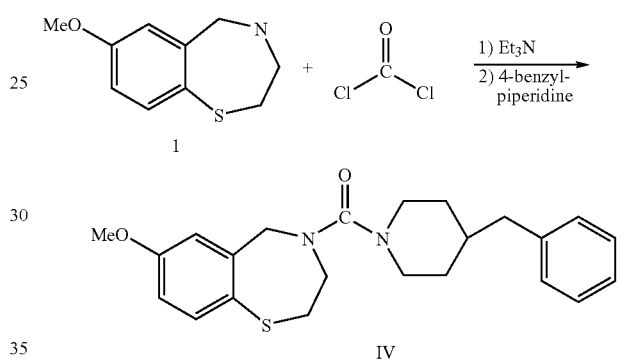

Example 12

Assay for High-Throughput Screening

The inventors have developed assays for screening biologically-active small molecules. These assays are based on rebinding of FKBP12 protein to RyR.

A highly-efficient assay for high-throughput screening for small molecules may be developed by immobilization of FKBP12.6 (GST-fusion protein) onto a 96-well plate coated with glutathione. PKA-phosphorylated ryanodine receptor type 2 (RyR2) is loaded onto the FKBP12.6-coated plate, and incubated with JTV-519 analogues at various concentrations (10-100 nM) for 30 min. Thereafter, the plate is washed to remove the unbound RyR2, and then incubated with anti-RyR2 antibody for 30 min. The plate is again washed to remove unbound anti-RyR2 antibody, and then treated with florescent-labeled secondary antibody. The plate is read by an automatic fluorescent plate reader for binding activity.

In an alternative assay, RyR2 is PKA-phosphorylated in the presence of $^{32}$P-ATP. Radioactive PKA-phosphorylated RyR2 is loaded onto an FKBP12.6-coated, 96-well plate, in the presence of JTV-519 analogues at various concentrations (10-100 nM) for 30 min. The plate is washed to remove the unbound radiolabeled RyR2, and then read by an automatic plate reader.

Example 13

Novel 1,4-Benzothiazepine Derivatives Allow Rebinding of FKBP12.6 TO RYR2

Figure 12:
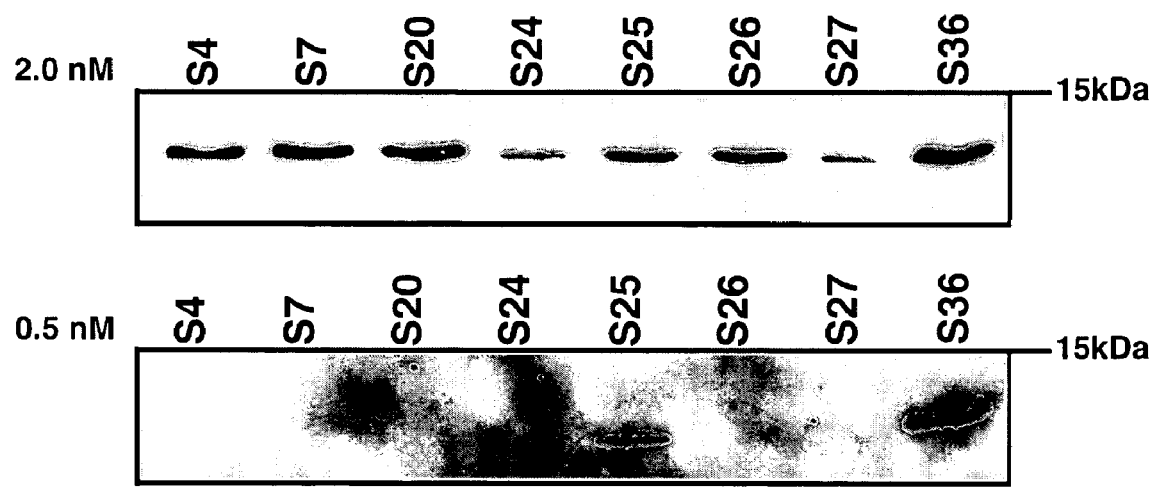
FIG. 12 shows that novel 1,4-benzothiazepine derivatives induce binding of calstabin2 (FKBP12.6) to PKA-phosphorylated cardiac ryanodine receptor (RyR2) at 0.5 nM. The structures of the derivatives are set forth in Appendix A. upper panel=2.0 nM of each compounds; lower panel=0.5 nM of each compound

Cardiac sarcoplasmic reticulum (SR) was phosphorylated with PKA for 30 min, at room temperature, resulting in complete dissociation of FKBP12.6 from the RyR2 complex. The SR (50 mg) was then incubated for 30 min, at room temperature, with 250 nM FKBP12.6 and the test compounds. Samples were centrifuged at 100,000 g for 10 min, and the pellets were washed 3 times with 10 mM imidazole buffer. After washing, proteins were separated by 15% PAGE. Immunoblots were developed using an anti-FKBP antibody. The results of this study are set forth in FIG. 12.

Example 14

Telemetry Recording and Exercise/EKG Testing in Mice

Studies were performed with FKBP12.6$^{+/-}$ mice (intervention group), age- and sex-matched FKBP12.6$^{-/-}$ mice (positive control), and wild-type FKBP12.6$^{+/+}$ mice (negative control). The absence of (FKBP12.6$^{-/-}$), or decrease in (FKBP12.6$^{+/-}$), FKBP12.6 protein was demonstrated by immunoblotting in cardiac tissue.

Continuous subcutaneous drug infusion of JTV-519 (at a plasma target concentration of 1.0 μM) or the derivative, S36 (at plasma target concentrations of 1.0 μM or 0.02 μM), into FKBP12.6$^{+/-}$ or FKBP12.6$^{-/-}$ mice occurred through a mini-osmotic pump, at a rate of 1.0 μl per hour, for 7 days prior to exercise testing (Alzet Durect Co., Cupertino, Calif.). Mice were anaesthetized using an intraperitoneal injection of ketamine (50 μg/kg) and xylazine (10 μg/kg), and radio EKG transmitters were implanted. ECG radio telemetry recordings of ambulatory animals were obtained 1 week following intraperitoneal implantation (Data Sciences International, St. Paul, Minn.). Standard criteria were used to measure ECG parameters.

Figure 13:
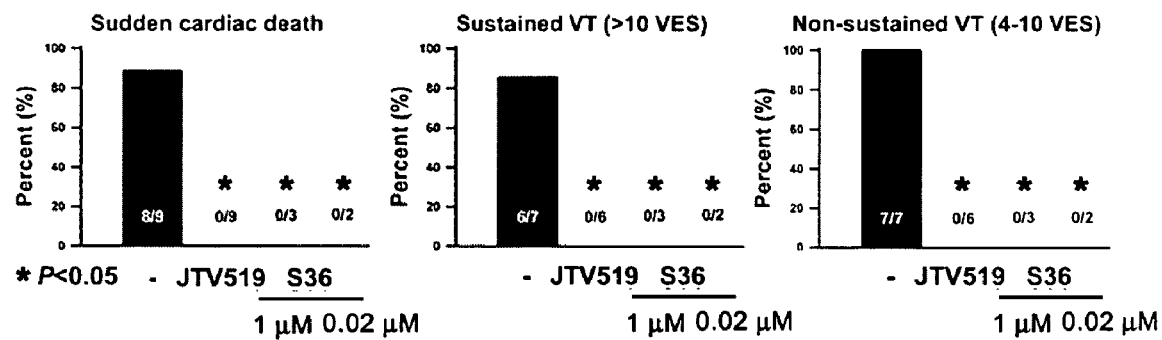
FIG. 13 shows that the 1,4-benzothiazepine derivative, S36 (depicted in Appendix A), prevents cardiac arrhythmias in mice at 200 nM. The bar graphs illustrate arrhythmic events or sudden cardiac death during exercise testing in FKBP12.6$^{+/-}$ mice—with or without drug treatment, as indicated. The left graph illustrates sudden cardiac death; the middle graph illustrates sustained VT; and the right graph illustrates non-sustained VT. Numbers refer to the total number of animals used in each group.

For stress tests, mice were exercised on an inclined treadmill, in a stepwise fashion, until exhaustion, and then intraperitoneally injected with epinephrine (0.2 mg/kg) for maximal sympathetic stimulation. Resting heart rates of ambulatory animals were then averaged over 4 h. Recovery after exercise testing, and monitoring of post-exercise events, were performed overnight. Sinus-cycle length (SCL), and PR, QRS, and QT intervals, were measured, and the rate-corrected QT interval (QTc) was calculated using the Mitchell formula. Plasma drug levels were confirmed by HPLC. Results are summarized in FIG. 13.

Example 15

JTV-519 Improves Cardiac Contractility in a Rat Model of Heart Failure

Figure 14:
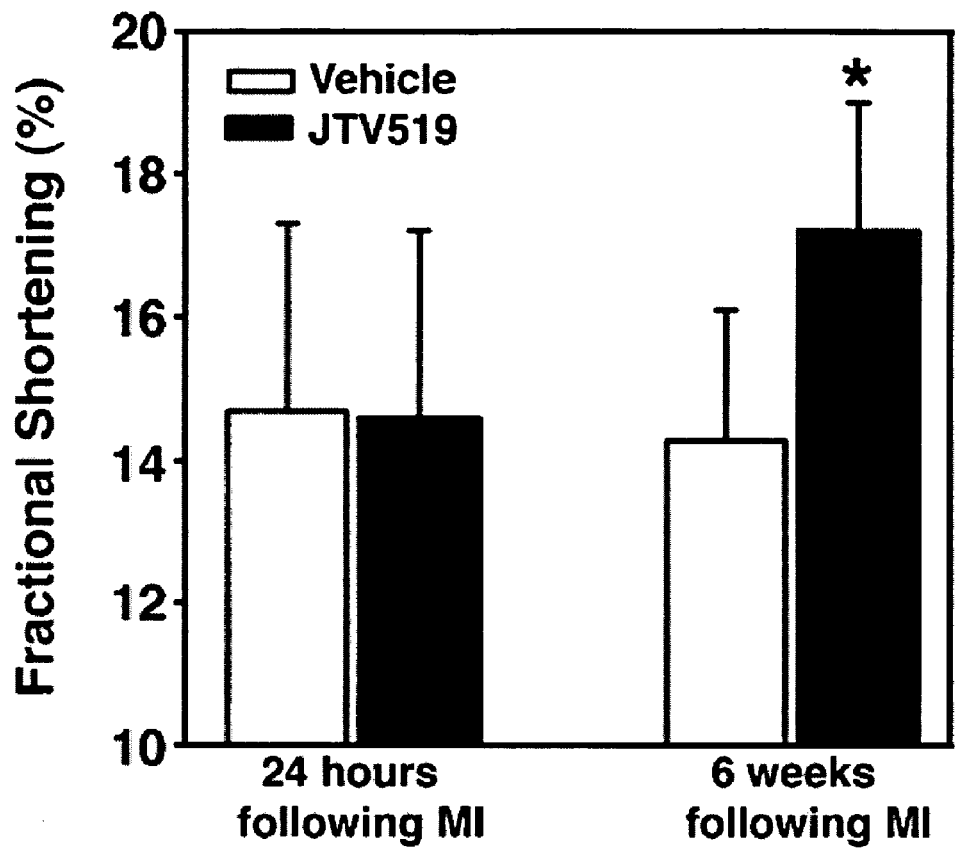
FIG. 14 demonstrates that JTV-519 improves cardiac contractility in a rat model of heart failure.
Figure 15:
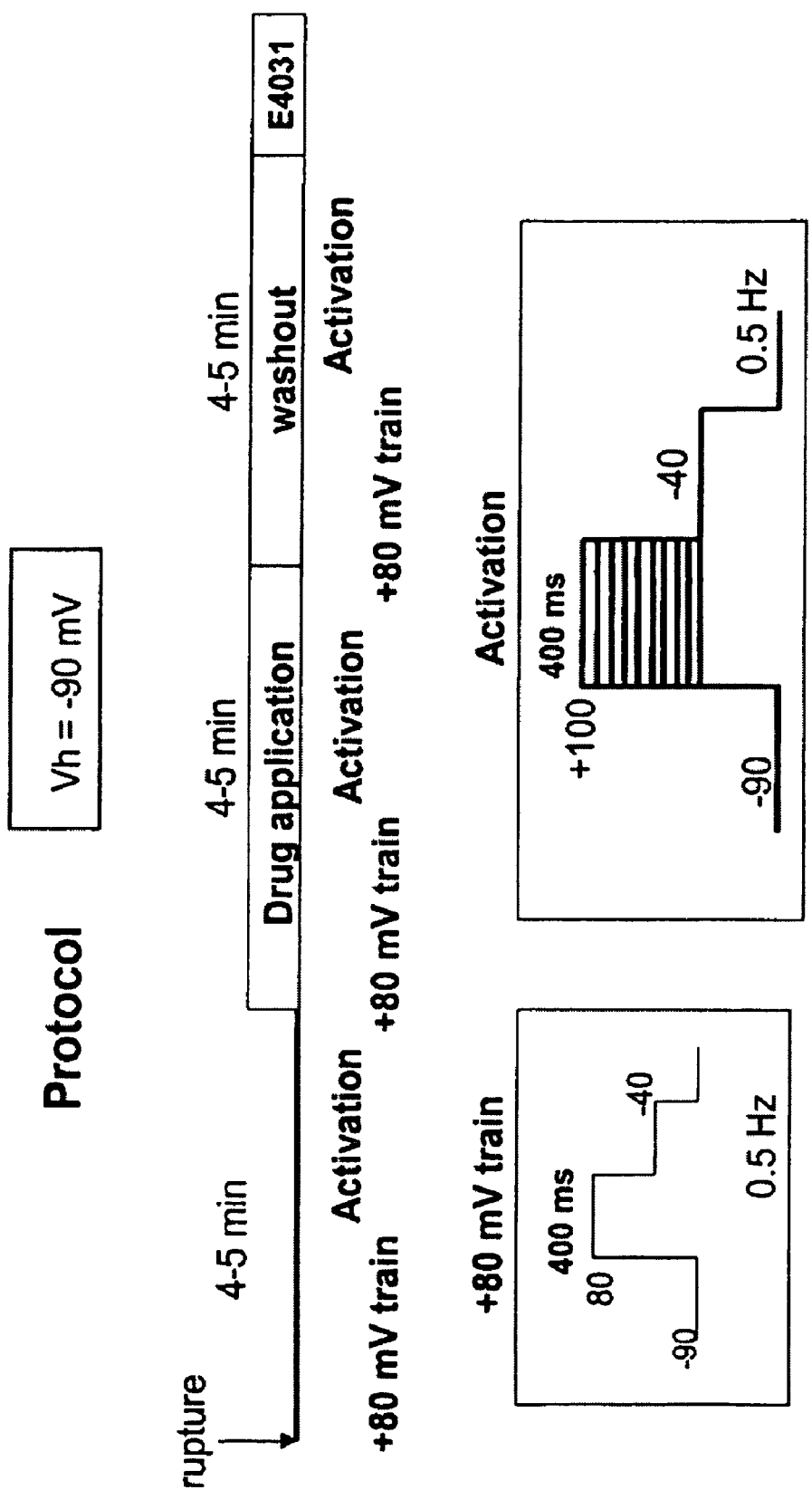
FIG. 15 demonstrates the experimental protocol used to test effects of the inventors' novel JTV-519-related compounds (disclosed herein) on hERG-channel current. Whole-cell patch-clamp experiments were carried out with physiological solutions at room temperature, in CHO cells transfected with hERG channel. Voltage-clamp protocols are shown in the lower panels. In vehicle, 0.1% DMSO in the external solution was applied with the same time-protocol as that shown in the upper panel.
Figure 16:
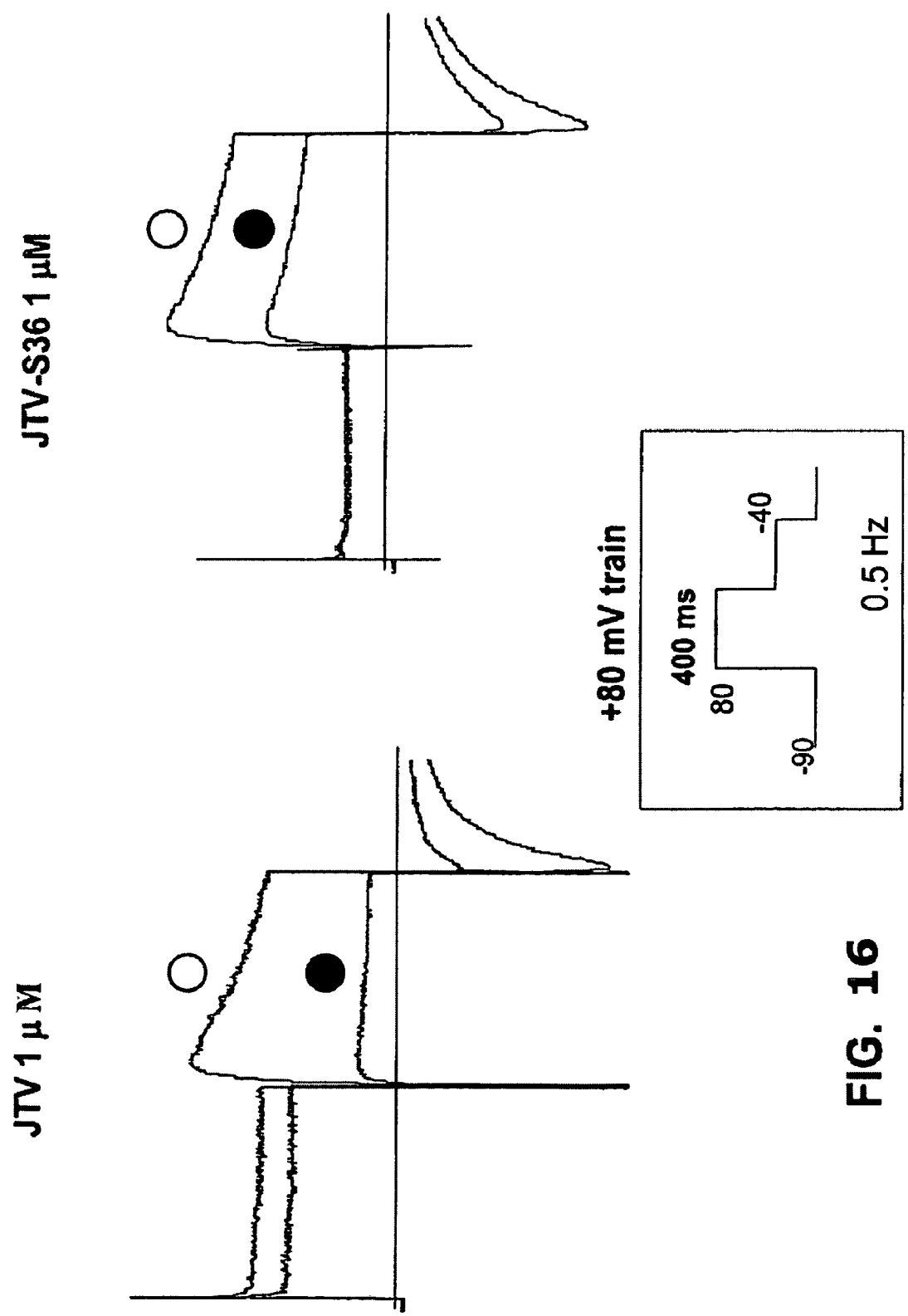
FIG. 16 illustrates the effects of JTV-519 and the inventors' novel JTV-519-related compound, S36 (disclosed herein), on hERG-channel currents elicited by 80-mV depolarization. Representative hERG-channel currents (I(Kr)) were recorded from CHO cells before (open circle) and after (closed circle) application of 1 μM JTV-519 (left panel) or 1 μM JTV-S36 (right panel). The voltage-clamp protocol is shown below the current traces. Currents were elicited during 400-msec depolarization to +80 mV, from a holding potential of −90 mV. It should be noted that, upon the 400-msec depolarization (which mimics the human action potential duration (APD)), hERG channels pass very little outward current, because they rapidly inactivate. Tail currents marked by circles in current traces were elicited by return of the membrane potential to −40 mV, in the recovery from inactivation through the open state. Because the tail current is a major contributor to control of the APD, effects of the drugs were evaluated by tail currents at −40 mV: JTV-519=83% block; JTV-S36=39% block.
Figure 17:
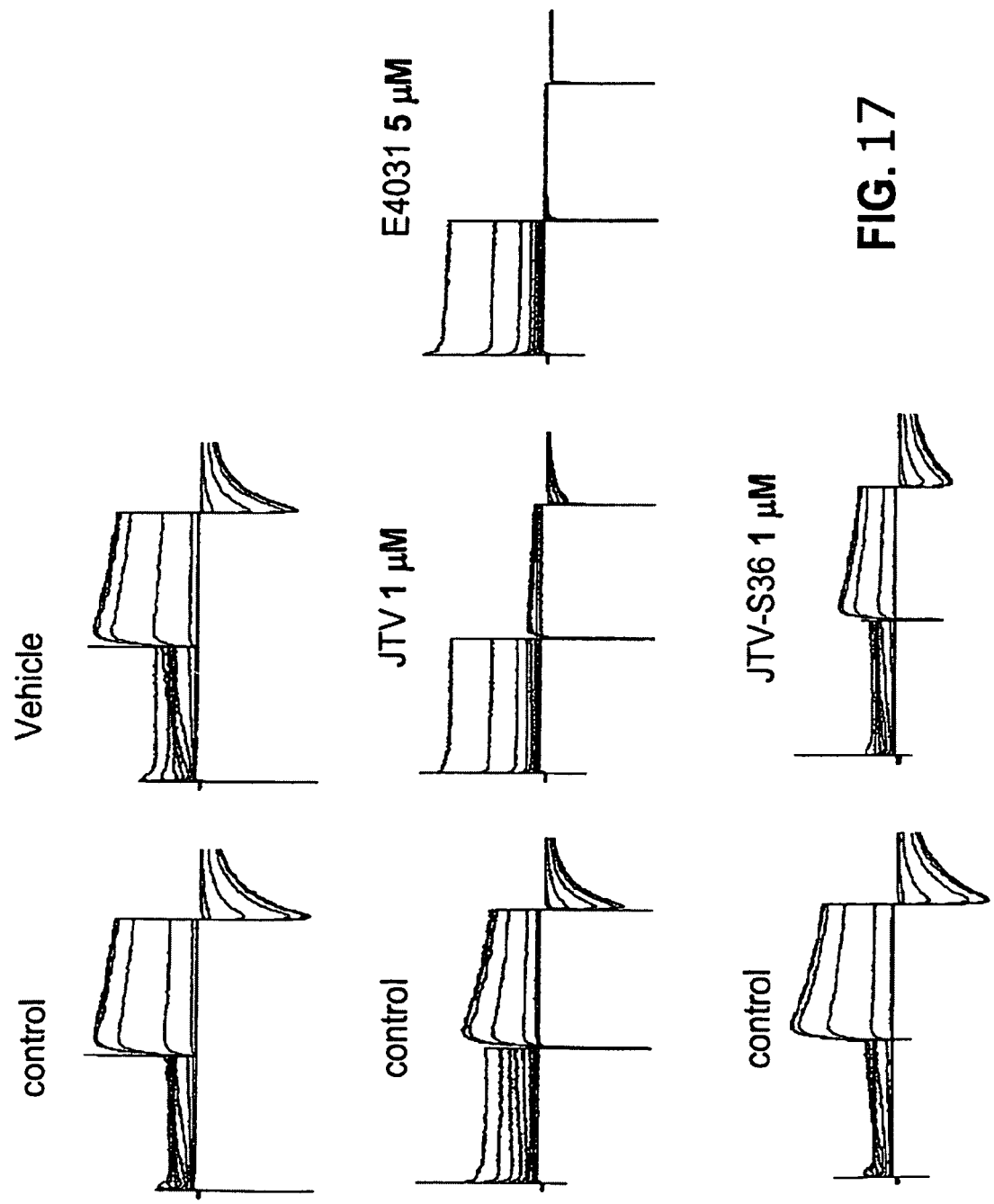
FIG. 17 shows effects of JTV-519, E4031, and the inventors' novel JTV-519-related compound, S36 (disclosed herein), on activation of hERG-channel currents (traces). Representative hERG-channel I-V relationships are shown before (control, left panels) and after (central panels) application of 0.1% DMSO (vehicle; upper central panel), 1 μM JTV-519 (middle central panel), and 1 μM JTV-S36 (lower central panel). The right panel shows that 5 μM E4031 (a class III anti-arrhythmic drug known to block hERG channels) completely blocked hERG-channel currents. (Note the tail currents at −40 mV). The voltage-clamp protocol is set forth in FIG. 15, as an I-V relationship.
Figure 18:
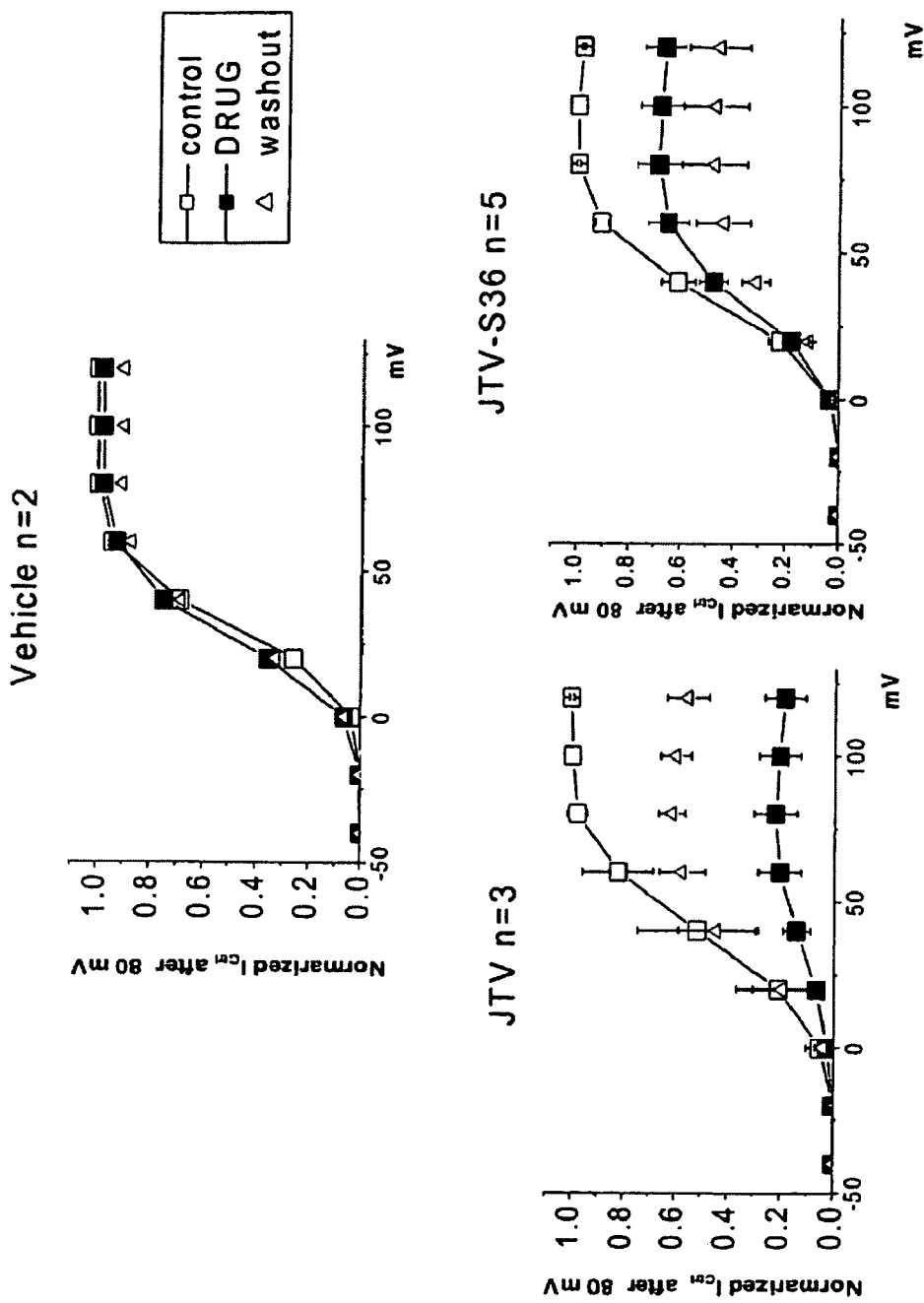
FIG. 18 demonstrates effects of JTV-519 and the inventors' novel JTV-519-related compound, S36 (disclosed herein), on activation of hERG-channel currents. The hERG-channel I-V relationships are shown for peak tail currents (activation) before (open squares) and after (closed squares) application of 0.1% DMSO (vehicle; upper panel), 1μM 15 JTV-519 (lower left panel), and 1μM JTV-S36 (lower right panel). Washout of the drugs is depicted with open triangles. The voltage-clamp protocol is set forth in FIG. 4, as an I-V relationship. It should be noted that JTV-S36 did not block hERG currents at negative potentials (0 mV; 20 mV depolarization) showing voltage-dependent block of I(Kr).

Rats were subjected to myocardial infarction (MI) by ligation of the left coronary artery. Treatment with JTV-519 (n=x) or vehicle (n=x), using implantable osmotic pumps (Alzet, Durect Corporation, Cupertino, Calif.), was initiated directly following MI. Myocardial systolic (Ds) and diastolic (Dd) diameters were determined at mid-papillary levels, using echocardiography 24 h and 6 weeks following MI; fractional shortening was then calculated. As shown in FIG. 14, treatment with JTV-519 significantly improved cardiac function in rats with heart failure.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for increasing binding of FKBP12.6 to RyR2 in a subject, or limiting a decrease in the level of RyR2-bound FKBP12.6 in a subject, comprising administering an effective amount of an agent to the subject, wherein the agent has the formula:

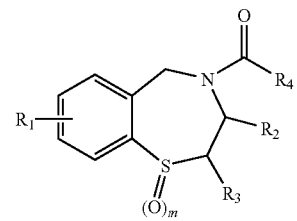

wherein
- $R_1$=OR' at position 7 on the benzothiazepine ring;
- R'=alkyl;
- $R_2$=H;
- $R_3$=H;
- $R_4$=halide, carboxylic acid, or an alkyl-O— or —S-alkyl-S—; and
- m=0, 1, or 2.

2. The method of claim 1, wherein the subject is a human.

3. The method of claim 1, wherein the subject has a cardiac condition selected from the group consisting of cardiac arrhythmia, tachycardia, ventricular arrhythmia, ventricular fibrillation, ventricular tachycardia, sustained ventricular tachycardia, non-sustained ventricular tachycardia, catecholaminergic polymorphic ventricular tachycardia (CPVT), heart failure, sudden cardiac death and exercise-induced sudden cardiac death.

4. The method of claim 1, wherein the effective amount of the agent is one or more of:
   (a) from about 5 mg/kg/day to about 20 mg/kg/day,
   (b) an amount resulting in a plasma concentration of from about 0.02 μM to about 1 μM in the subject, or
   (c) an amount resulting in a plasma concentration of from about 300 ng/ml to about 1000 ng/ml in the subject.

5. The method of claim 1, wherein the agent is

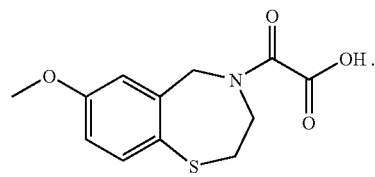

6. A method for reducing the risk of sudden cardiac death, sustained ventricular tachycardia and non-sustained ventricular tachycardia in a subject, comprising administering an effective amount of an agent to the subject, wherein the agent has the formula:

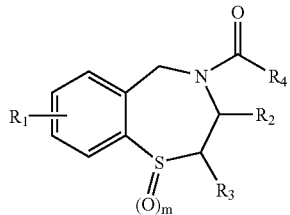

wherein
$R_1$=OR' at position 7 on the benzothiazepine ring;
R' =alkyl;
$R_2$=H;
$R_3$=H;
$R_4$=halide, carboxylic acid, or an alkyl-O— or —S-alkyl-S—; and
m=0, 1, or 2.

7. The method of claim 6, wherein the agent is administered to a subject that has or is at risk of developing a condition selected from the group consisting of cardiac arrhythmia, tachycardia, ventricular arrhythmia, ventricular fibrillation, ventricular tachycardia, sustained ventricular tachycardia, non-sustained ventricular tachycardia, catecholaminergic polymorphic ventricular tachycardia (CPVT), heart failure, sudden cardiac death and exercise-induced sudden cardiac death.

8. The method of claim 6, wherein the effective amount of the agent is one or more of:
(a) from about 5 mg/kg/day to about 20 mg/kg/day,
(b) an amount resulting in a plasma concentration of from about 0.02 μM to about 1.0 μM in the subject, or
(c) an amount resulting in a plasma concentration of from about 300 ng/ml to about 1000 ng/ml in the subject.

9. The method of claim 6, wherein the agent is

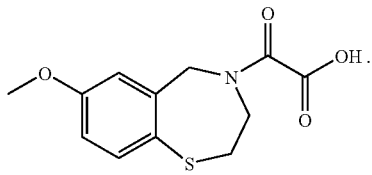

10. The method of claim 6, wherein the subject is a human.
11. The method of claim 1, wherein $R_4$=carboxylic acid and m=0 or 1.
12. The method of claim 1, wherein m=0 or 1.
13. The method of claim 12, wherein $R_4$=carboxylic acid and R'=methyl.
14. The method of claim 13, wherein m=0; and $R_4$=carboxylic acid.
15. The method of claim 6, wherein $R_4$=carboxylic acid and m=0 or 1.
16. The method of claim 6, wherein m=0 or 1.
17. The method of claim 16, wherein $R_4$=carboxylic acid and R'=methyl.
18. The method of claim 17, wherein m=0; and $R_4$=carboxylic acid.

19. A method for treating cardiac arrhythmia in a subject, comprising administering an effective amount of an agent to the subject, wherein the agent has the formula:

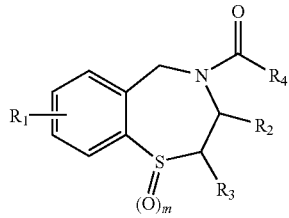

wherein
$R_1$=OR' at position 7 on the benzothiazepine ring;
R' =alkyl;
$R_2$=H;
$R_3$=H;
$R_4$=halide, carboxylic acid, or an alkyl-O— or —S-alkyl-S—; and
m=0, 1, or 2.

20. The method of claim 19, wherein the effective amount of the agent is one or more of:
(a) from about 5 mg/kg/day to about 20 mg/kg/day,
(b) an amount resulting in a plasma concentration of from about 0.02 μM to about 1 μM in the subject, or
(c) an amount resulting in a plasma concentration of from about 300 ng/ml to about 1000 ng/ml in the subject.

21. The method of claim 19, wherein the agent is

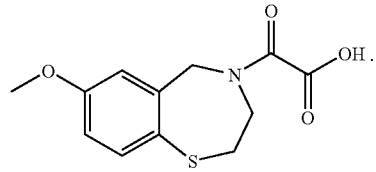

22. The method of claim 19, wherein the subject is a human.
23. The method of claim 19, wherein $R_4$=carboxylic acid and m=0 or 1.
24. The method of claim 19, wherein m=0 or 1.
25. The method of claim 24, wherein $R_4$=carboxylic acid and R'=methyl.
26. The method of claim 25, wherein m=0; and $R_4$=carboxylic acid.
27. The method of claim 5, wherein the subject is a human.
28. The method of claim 5, wherein the subject has a cardiac condition selected from the group consisting of cardiac arrhythmia, tachycardia, ventricular arrhythmia, ventricular fibrillation, ventricular tachycardia, sustained ventricular tachycardia, non-sustained ventricular tachycardia, catecholaminergic polymorphic ventricular tachycardia (CPVT), heart failure, sudden cardiac death and exercise-induced sudden cardiac death.
29. The method of claim 5, wherein the effective amount of the agent is one or more of:
(a) from about 5 mg/kg/day to about 20 mg/kg/day,
(b) an amount resulting in a plasma concentration of from about 0.02 μM to about 1.0 μM in the subject, or
(c) an amount resulting in a plasma concentration of from about 300 ng/ml to about 1000 ng/ml in the subject.

* * * * *

UNITED STATES PATENT AND TRADEMARK OFFICE
CERTIFICATE OF CORRECTION

PATENT NO. : 7,718,644 B2  Page 1 of 1
APPLICATION NO. : 10/809089
DATED : May 18, 2010
INVENTOR(S) : Marks et al.

It is certified that error appears in the above-identified patent and that said Letters Patent is hereby corrected as shown below:

Columns 14-15:
Delete the text beginning at line 59 through column 15, line 42, and insert this deleted text in column 16, after line 34 and before the heading "DETAILED DESCRIPTION OF THE INVENTION".

Column 76:
Line 26 (claim 20, line 5), change "1 µM" to -- 1.0 µM --.

Signed and Sealed this

Fourteenth Day of December, 2010

David J. Kappos
*Director of the United States Patent and Trademark Office*